United States Patent
Miyagi et al.

(10) Patent No.: US 9,657,313 B2
(45) Date of Patent: May 23, 2017

(54) ISOPRENE OLIGOMER, POLYISOPRENE, PROCESSES FOR PRODUCING THESE MATERIALS, RUBBER COMPOSITION, AND PNEUMATIC TIRE

(71) Applicants: SUMITOMO RUBBER INDUSTRIES, LTD., Kobe-shi, Hyogo (JP); YAMAGATA UNIVERSITY, Yamagata-shi, Yamagata (JP)

(72) Inventors: Yukino Miyagi, Kobe (JP); Naoya Ichikawa, Kobe (JP); Norimasa Ohya, Yamagata (JP)

(73) Assignees: SUMITOMO RUBBER INDUSTRIES, LTD., Kobe-Shi (JP); YAMAGATA UNIVERSITY, Yamagata-Shi (JP)

( * ) Notice: Subject to any disclaimer, the term of this patent is extended or adjusted under 35 U.S.C. 154(b) by 0 days.

(21) Appl. No.: 15/133,084

(22) Filed: Apr. 19, 2016

(65) Prior Publication Data
US 2016/0222418 A1 Aug. 4, 2016

Related U.S. Application Data

(62) Division of application No. 13/809,616, filed as application No. PCT/JP2011/064774 on Jun. 28, 2011, now Pat. No. 9,371,342.

(30) Foreign Application Priority Data

Jul. 14, 2010 (JP) ................................. 2010-160120
Dec. 13, 2010 (JP) ................................. 2010-277384

(51) Int. Cl.
C08F 136/08 (2006.01)
C12P 5/00 (2006.01)
(Continued)

(52) U.S. Cl.
CPC ............... *C12P 5/007* (2013.01); *B60C 1/00* (2013.01); *B60C 1/0016* (2013.04); *B60C 1/0025* (2013.04); *B60C 13/001* (2013.04); *C07C 21/04* (2013.01); *C07C 33/02* (2013.01); *C07C 47/21* (2013.01); *C07C 57/03* (2013.01); *C07C 255/07* (2013.01); *C07C 255/23* (2013.01); *C07F 9/098* (2013.01); *C07F 9/143* (2013.01); *C08F 36/08* (2013.01); *C08L 9/00* (2013.01); *C12N 9/1085* (2013.01); *C12P 7/00* (2013.01); *C12P 7/04* (2013.01); *C12P 7/24* (2013.01); *C12P 7/40* (2013.01); *C12P 7/62* (2013.01); *C12P 9/00* (2013.01); *C12P 13/00* (2013.01);
(Continued)

(58) Field of Classification Search
USPC .......................................... 526/72, 201, 274
See application file for complete search history.

(56) References Cited

U.S. PATENT DOCUMENTS 4,886,904 A * 12/1989 Tanaka .................... C07C 29/10
560/249
5,004,735 A 4/1991 Okamoto et al.
(Continued)

FOREIGN PATENT DOCUMENTS

CN 101160328 A 4/2008
CN 101688191 A 3/2010
(Continued)

OTHER PUBLICATIONS

English Machine Translation of JP-10-316715-A published Dec. 2, 1998.
English Machine Translation of JP-2003-238603-A published Aug. 27, 2003.
International Search Report for PCT/JP2011/064774 dated Oct. 11, 2011.

*Primary Examiner* — Pancham Bakshi
(74) *Attorney, Agent, or Firm* — Birch, Stewart, Kolasch & Birch, LLP

(57) ABSTRACT

The invention relates to an isoprene oligomer that contains a trans structural moiety and a cis structural moiety, which can be represented by the following formula (1), wherein at least 1 atom or group in the trans structural moiety is replaced by another atom or group. The invention also relates to a polyisoprene, which is biosynthesized using the isoprene oligomer and isopentenyl diphosphate. Further, this invention provides a rubber composition comprising the isoprene oligomer and/or the polyisoprene, and a pneumatic tire, including tire components (e.g., treads and sidewalls) formed from the rubber composition.

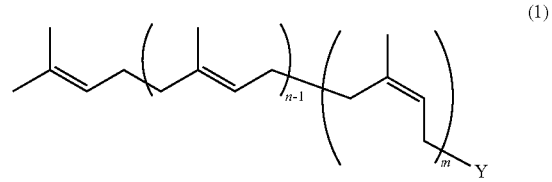

(1)

wherein n represents an integer from 1 to 10; m represents an integer from 1 to 30; and Y represents a hydroxy group, a formyl group, a carboxy group, an ester group, a carbonyl group, or a group represented by the following formula (2):

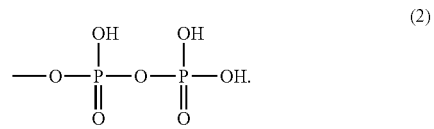

(2)

8 Claims, No Drawings

(51) Int. Cl.
*B60C 1/00* (2006.01)
*C07F 9/09* (2006.01)
*C08F 36/08* (2006.01)
*C08L 9/00* (2006.01)
*C12N 9/10* (2006.01)
*B60C 13/00* (2006.01)
*C12P 7/00* (2006.01)
*C12P 7/04* (2006.01)
*C12P 7/24* (2006.01)
*C12P 7/40* (2006.01)
*C12P 7/62* (2006.01)
*C12P 9/00* (2006.01)
*C12P 13/00* (2006.01)
*C12P 13/02* (2006.01)
*C07C 21/04* (2006.01)
*C07C 33/02* (2006.01)
*C07C 47/21* (2006.01)
*C07C 57/03* (2006.01)
*C07C 255/07* (2006.01)
*C07C 255/23* (2006.01)
*C07F 9/143* (2006.01)

(52) U.S. Cl.
CPC ............. *C12P 13/002* (2013.01); *C12P 13/02*
(2013.01); *Y02P 20/52* (2015.11)

(56) References Cited

U.S. PATENT DOCUMENTS

| | | |
|---|---|---|
| 5,245,060 A | 9/1993 | Hamamura et al. |
| 5,756,475 A | 5/1998 | Inomata et al. |
| 2009/0292043 A1 | 11/2009 | Kurazumi et al. |
| 2010/0138954 A1 | 6/2010 | Sallaud et al. |
| 2010/0218272 A1 | 8/2010 | Nakazawa et al. |
| 2011/0201771 A1* | 8/2011 | Puskas .................. C08F 36/04 526/193 |

FOREIGN PATENT DOCUMENTS

| | | |
|---|---|---|
| EP | 1 050 582 A2 | 11/2000 |
| EP | 1 083 201 A2 | 3/2001 |
| EP | 2 093 222 A1 | 8/2009 |
| JP | 2-25415 A | 1/1990 |
| JP | 4-283548 A | 10/1992 |
| JP | 9-268162 A | 10/1997 |
| JP | 10-316715 A | 12/1998 |
| JP | 2000-1573 A | 1/2000 |
| JP | 2000-1575 A | 1/2000 |
| JP | 2000-316586 A | 11/2000 |
| JP | 2003-238603 A | 8/2003 |
| JP | 2010-193770 A | 9/2010 |

* cited by examiner

```
                         SEQUENCE LISTING

<160> NUMBER OF SEQ ID NOS: 42

<210> SEQ ID NO 1
<211> LENGTH: 750
<212> TYPE: DNA
<213> ORGANISM: Micrococcus luteus B-P26

<400> SEQUENCE: 1
atgtttccaa ttaagaagcg aaaagcaata aaaaataata acattaatgc ggcacaaatt      60
ccgaaacata ttgcaatcat tatggacgga aatggccgat gggcaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaaaa ttggtctcgt     240
```

```
cctaaagatg aggttaatta cttgatgaaa ctaccgggtg attttttaaa cacattttta    300
ccggaactca ttgaaaaaaa tgttaaagtt gaaacgattg ctttattga tgatttaccg    360 gaccatacaa aaaaagcagt gttagaagcg aaagagaaaa cgaaacataa tacaggttta    420
acgctcgtgt ttgcactgaa ttatggtggg cgtaaagaaa ttatttcagc agtgcagtta    480
atcgcagagc gttacaaatc tggtgaaatt tctttagatg aaattagtga aactcatttt    540
aatgaatatt tatttacagc aaatatgcct gatcctgagt tgttaatcag aacttccggt    600
gaagaacgtt taagtaactt tttaatttgg caatgttcat atagtgagtt tgtatttata    660
gatgaattct ggccggattt taatgaagaa agtttagcac aatgtatatc aatatatcag    720
aatcgtcatc gacgttttgg tggattataa                                    750
```

<210> SEQ ID NO 2
<211> LENGTH: 249
<212> TYPE: PRT
<213> ORGANISM: Micrococcus luteus B-P26

<400> SEQUENCE: 2

```
Met Phe Pro Ile Lys Lys Arg Lys Ala Ile Lys Asn Asn Ile Asn
1               5                   10                  15

Ala Ala Gln Ile Pro Lys His Ile Ala Ile Ile Met Asp Gly Asn
                20                  25                  30

Arg Trp Ala Lys Gln Lys Lys Met Pro Arg Ile Lys Gly His Tyr Glu
            35                  40                  45

Gly Met Gln Thr Val Lys Lys Ile Thr Arg Tyr Ala Ser Asp Leu Gly
        50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Leu Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Glu Arg Leu Ser Asn Phe Leu
        195                 200                 205

Ile Trp Gln Cys Ser Tyr Ser Glu Phe Val Phe Ile Asp Glu Phe Trp
210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245
```

<210> SEQ ID NO 3
<211> LENGTH: 750
<212> TYPE: DNA
<213> ORGANISM: Artificial Sequnece
<220> FEATURE:
<223> OTHER INFORMATION: Nucleotide sequence of variant enzyme N31A

<400> SEQUENCE: 3

```
atgtttccaa ttaagaagcg aaaagcaata aaaataata acattaatgc ggcacaaatt      60
ccgaaacata ttgcaatcat tatggacgga gcaggccgat gggcaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaaaa ttggtctcgt     240
cctaaagatg aggttaatta cttgatgaaa ctaccgggtg attttttaaa cacattttta     300
ccggaactca ttgaaaaaaa tgttaaagtt gaaacgattg gctttattga tgatttaccg     360
gaccatacaa aaaagcagt gttagaagcg aaagagaaaa cgaaacataa tacaggttta     420
acgctcgtgt ttgcactgaa ttatggtggg cgtaaagaaa ttatttcagc agtgcagtta     480
atcgcagagc gttacaaatc tggtgaaatt tctttagatg aaattagtga aactcatttt     540
aatgaatatt tatttacagc aaatatgcct gatcctgagt tgttaatcag aacttccggt     600
gaagaacgtt taagtaactt tttaatttgg caatgttcat atagtgagtt tgtatttata     660
gatgaattct ggccggattt taatgaagaa agtttagcac aatgtatatc aatatatcag     720
aatcgtcatc gacgttttgg tggattataa                                      750
```

<210> SEQ ID NO 4
<211> LENGTH: 249
<212> TYPE: PRT
<213> ORGANISM: Artificial Sequnece
<220> FEATURE:
<223> OTHER INFORMATION: Amino acid sequence of variant enzyme N31A

<400> SEQUENCE: 4

```
Met Phe Pro Ile Lys Lys Arg Lys Ala Ile Lys Asn Asn Asn Ile Asn
1               5                   10                  15

Ala Ala Gln Ile Pro Lys His Ile Ala Ile Ile Met Asp Gly Ala Gly
            20                  25                  30

Arg Trp Ala Lys Gln Lys Lys Met Pro Arg Ile Lys Gly His Tyr Glu
        35                  40                  45

Gly Met Gln Thr Val Lys Lys Ile Thr Arg Tyr Ala Ser Asp Leu Gly
    50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Leu Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
    130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Glu Arg Leu Ser Asn Phe Leu
        195                 200                 205
```

```
Ile Trp Gln Cys Ser Tyr Ser Glu Phe Val Phe Ile Asp Glu Phe Trp
        210                 215                 220

Pro Asp Phe Asn Glu Glu Ser Leu Ala Gln Cys Ile Ser Ile Tyr Gln
225                 230                 235                 240

Asn Arg His Arg Phe Gly Gly Leu
            245

<210> SEQ ID NO 5
<211> LENGTH: 750
<212> TYPE: DNA
<213> ORGANISM: Artificial Sequnece
<220> FEATURE:
<223> OTHER INFORMATION: Nucleotide sequence of variant enzyme N77A

<400> SEQUENCE: 5
atgtttccaa ttaagaagcg aaaagcaata aaaaataata acattaatgc ggcacaaatt      60
ccgaaacata ttgcaatcat tatggacgga atggccgatg ggcaaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaagc atggtctcgt     240
cctaaagatg aggttaatta cttgatgaaa ctaccgggtg attttttaaa cactttttta     300
ccggaactca ttgaaaaaaa tgttaaagtt gaaacgattg ctttattga tgatttaccg      360 gaccatacaa aaaagcagt gttagaagcg aagagaaaa cgaaacataa tacaggttta      420
acgctcgtgt ttgcactgaa ttatggtggg cgtaaagaaa ttatttcagc agtgcagtta     480
atcgcagagc gttacaaatc tggtgaaatt tctttagatg aaattagtga aactcatttt     540
aatgaatatt tatttacagc aaatatgcct gatcctgagt tgttaatcag aacttccggt     600
gaagaacgtt taagtaactt tttaatttgg caatgttcat atagtgagtt tgtatttata     660
gatgaattct ggccggattt taatgaagaa agtttagcac aatgtatatc aatatatcag     720
aatcgtcatc gacgttttgg tggattataa                                       750

<210> SEQ ID NO 6
<211> LENGTH: 249
<212> TYPE: PRT
<213> ORGANISM: Artificial Sequnece
<220> FEATURE:
<223> OTHER INFORMATION: Amino acid sequence of variant enzyme N77A

<400> SEQUENCE: 6

Met Phe Pro Ile Lys Lys Arg Lys Ala Ile Lys Asn Asn Ile Asn
1               5                   10                  15

Ala Ala Gln Ile Pro Lys His Ile Ala Ile Ile Met Asp Gly Asn Gly
                20                  25                  30

Arg Trp Ala Lys Gln Lys Lys Met Pro Arg Ile Lys Gly His Tyr Glu
            35                  40                  45

Gly Met Gln Thr Val Lys Lys Ile Thr Arg Tyr Ala Ser Asp Leu Gly
        50                  55                  60

Val Lys Tyr Leu Thr Leu Tyr Ala Phe Ser Thr Glu Ala Trp Ser Arg
65                  70                  75                  80

Pro Lys Asp Glu Val Asn Tyr Leu Met Lys Leu Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125
```

Glu Ala Lys Glu Lys Thr Lys His Asn Thr Gly Leu Thr Leu Val Phe
            130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Glu Arg Leu Ser Asn Phe Leu
        195                 200                 205

Ile Trp Gln Cys Ser Tyr Ser Glu Phe Val Phe Ile Asp Glu Phe Trp
    210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245

<210> SEQ ID NO 7
<211> LENGTH: 750
<212> TYPE: DNA
<213> ORGANISM: Artificial Sequnece
<220> FEATURE:
<223> OTHER INFORMATION: Nucleotide sequence of variant enzyme L91N

<400> SEQUENCE: 7

```
atgtttccaa ttaagaagcg aaaagcaata aaaataata acattaatgc ggcacaaatt      60
ccgaaacata ttgcaatcat tatggacgga atggccgat gggcaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaaaa ttggtctcgt     240
cctaaagatg aggttaatta cttgatgaaa acccgggtg atttttttaaa cacatttta     300
ccggaactca ttgaaaaaaa tgttaaagtt gaaacgattg ctttattga tgatttaccg     360
gaccatacaa aaaagcagt gttagaagcg aagagaaaa cgaaacataa tacaggttta     420
acgctcgtgt ttgcactgaa ttatggtggg cgtaaagaaa ttattcagc agtgcagtta     480
atcgcagagc gttacaaatc tggtgaaatt tctttagatg aaattagtga aactcatttt     540
aatgaatatt tatttacagc aaatatgcct gatcctgagt tgttaatcag aacttccggt     600
gaagaacgtt taagtaactt tttaattggg caatgttcat atagtgagtt tgtattata      660
gatgaattct ggccggattt taatgaagaa agtttagcac aatgtatatc aatatatcag     720
aatcgtcatc gacgttttgg tggattataa                                     750
```

<210> SEQ ID NO 8
<211> LENGTH: 249
<212> TYPE: PRT
<213> ORGANISM: Artificial Sequnece
<220> FEATURE:
<223> OTHER INFORMATION: Amino acid sequence of variant enzyme L91N

<400> SEQUENCE: 8

Met Phe Pro Ile Lys Lys Arg Lys Ala Ile Lys Asn Asn Ile Asn
1               5                   10                  15

Ala Ala Gln Ile Pro Lys His Ile Ala Ile Met Asp Gly Asn Gly
            20                  25                  30

Arg Trp Ala Lys Gln Lys Lys Met Pro Arg Ile Lys Gly His Tyr Glu
        35                  40                  45

Gly Met Gln Thr Val Lys Lys Ile Thr Arg Tyr Ala Ser Asp Leu Gly
    50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Asn Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
    130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Arg Leu Ser Asn Phe Leu
    195                 200                 205

Ile Trp Gln Cys Ser Tyr Ser Glu Phe Val Phe Ile Asp Glu Phe Trp
210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245

<210> SEQ ID NO 9
<211> LENGTH: 750
<212> TYPE: DNA
<213> ORGANISM: Artificial Sequnece
<220> FEATURE:
<223> OTHER INFORMATION: Nucleotide sequence of variant enzyme L91D

<400> SEQUENCE: 9
atgtttccaa ttaagaagcg aaaagcaata aaaaataata acattaatgc ggcacaaatt      60
ccgaaacata ttgcaatcat tatggacgga atggccgat gggcaaaaca gaaaaaaatg     120
ccgcgcataa aaggacatta tgaaggcatg cagaccgtaa agaaaatcac aagatatgct    180
agtgatttag gtgtaaagta cttaacgctg tacgcatttt caactgaaaa ttggtctcgt    240
cctaaagatg aggttaatta cttgatgaaa gatccgggtg attttttaaa cacatttta    300
ccggaactca ttgaaaaaaa tgttaaagtt gaaacgattg ctttattga tgatttaccg    360
gaccatacaa aaaagcagt gttagaagcg aaagagaaaa cgaaacataa tacaggttta    420
acgctcgtgt ttgcactgaa ttatggtggg cgtaaagaaa ttatttcagc agtgcagtta    480
atcgcagagc gttacaaatc tggtgaaatt tctttagatg aaattagtga aactcatttt    540
aatgaatatt tatttacagc aaatatgcct gatcctgagt tgttaatcag aacttccggt    600
gaagaacgtt taagtaactt tttaatttgg caatgttcat atagtgagtt tgtatttata    660
gatgaattct ggccggattt taatgaagaa agtttagcac aatgtatatc aatatatcag    720
aatcgtcatc gacgttttgg tggattataa                                     750

<210> SEQ ID NO 10
<211> LENGTH: 249

<212> TYPE: PRT
<213> ORGANISM: Artificial Sequnece
<220> FEATURE:
<223> OTHER INFORMATION: Amino acid sequence of variant enzyme L91D

<400> SEQUENCE: 10

```
Met Phe Pro Ile Lys Lys Arg Lys Ala Ile Lys Asn Asn Ile Asn
1               5                   10                  15

Ala Ala Gln Ile Pro Lys His Ile Ala Ile Met Asp Gly Asn Gly
                20                  25                  30

Arg Trp Ala Lys Gln Lys Lys Met Pro Arg Ile Lys Gly His Tyr Glu
            35                  40                  45

Gly Met Gln Thr Val Lys Lys Ile Thr Arg Tyr Ala Ser Asp Leu Gly
    50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Asp Pro Gly Asp Phe Leu
                85                  90                  95

Asn Thr Phe Leu Pro Glu Leu Ile Glu Lys Asn Val Lys Val Glu Thr
                100                 105                 110

Ile Gly Phe Ile Asp Asp Leu Pro Asp His Thr Lys Lys Ala Val Leu
            115                 120                 125

Glu Ala Lys Glu Lys Thr Lys His Asn Thr Gly Leu Thr Leu Val Phe
130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Arg Leu Ser Asn Phe Leu
            195                 200                 205

Ile Trp Gln Cys Ser Tyr Ser Glu Phe Val Phe Ile Asp Glu Phe Trp
210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245
```

<210> SEQ ID NO 11
<211> LENGTH: 750
<212> TYPE: DNA
<213> ORGANISM: Artificial Sequnece
<220> FEATURE:
<223> OTHER INFORMATION: Nucleotide sequence of variant enzyme N31Q

<400> SEQUENCE: 11

```
atgtttccaa ttaagaagcg aaaagcaata aaaaataata acattaatgc ggcacaaatt      60
ccgaaacata ttgcaatcat tatggacgga caaggccgat gggcaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaaaa ttggtctcgt     240
cctaaagatg aggttaatta cttgatgaaa ctaccgggtg attttttaaa cacattttta     300
ccggaactca ttgaaaaaaa tgttaaagtt gaaacgattg gctttattga tgatttaccg     360
gaccatacaa aaaagcagt gttagaagcg aaagagaaaa cgaaacataa tacaggttta     420
```

```
acgctcgtgt ttgcactgaa ttatggtggg cgtaaagaaa ttatttcagc agtgcagtta    480
atcgcagagc gttacaaatc tggtgaaatt tctttagatg aaattagtga aactcatttt    540
aatgaatatt tatttacagc aaatatgcct gatcctgagt tgttaatcag aacttccggt    600
gaagaacgtt taagtaactt tttaatttgg caatgttcat atagtgagtt tgtatttata    660
gatgaattct ggccggattt taatgaagaa agtttagcac aatgtatatc aatatatcag    720
aatcgtcatc gacgttttgg tggattataa                                     750
```

<210> SEQ ID NO 12
<211> LENGTH: 249
<212> TYPE: PRT
<213> ORGANISM: Artificial Sequnece
<220> FEATURE:
<223> OTHER INFORMATION: Amino acid sequence of variant enzyme N31Q

<400> SEQUENCE: 12

```
Met Phe Pro Ile Lys Lys Arg Lys Ala Ile Lys Asn Asn Ile Asn
1               5                   10                  15

Ala Ala Gln Ile Pro Lys His Ile Ala Ile Met Asp Gly Gln Gly
                20                  25                  30

Arg Trp Ala Lys Gln Lys Lys Met Pro Arg Ile Lys Gly His Tyr Glu
                35                  40                  45

Gly Met Gln Thr Val Lys Lys Ile Thr Arg Tyr Ala Ser Asp Leu Gly
            50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Leu Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Glu Arg Leu Ser Asn Phe Leu
        195                 200                 205

Ile Trp Gln Cys Ser Tyr Ser Glu Phe Val Phe Ile Asp Glu Phe Trp
    210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245
```

<210> SEQ ID NO 13
<211> LENGTH: 750
<212> TYPE: DNA
<213> ORGANISM: Artificial Sequnece
<220> FEATURE:
<223> OTHER INFORMATION: Nucleotide sequence of variant enzyme N77Q

<400> SEQUENCE: 13

```
atgtttccaa ttaagaagcg aaaagcaata aaaaataata acattaatgc ggcacaaatt      60
ccgaaacata ttgcaatcat tatggacgga atggccgat gggcaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaaca atggtctcgt     240
cctaaagatg aggttaatta cttgatgaaa ctaccgggtg attttttaaa cacattttta     300
ccggaactca ttgaaaaaaa tgttaaagtt gaaacgattg gctttattga tgatttaccg     360
gaccatacaa aaaagcagt gttagaagcg aaagagaaaa cgaaacataa tacaggttta     420
acgctcgtgt ttgcactgaa ttatggtggg cgtaaagaaa ttatttcagc agtgcagtta     480
atcgcagagc gttacaaatc tggtgaaatt tctttagatg aaattagtga aactcatttt     540
aatgaatatt tatttacagc aaatatgcct gatcctgagt tgttaatcag aacttccggt     600
gaagaacgtt taagtaactt tttaatttgg caatgttcat atagtgagtt tgtatttata     660
gatgaattct ggccggattt taatgaagaa agtttagcac aatgtatatc aatatatcag     720
aatcgtcatc gacgttttgg tggattataa                                     750
```

<210> SEQ ID NO 14
<211> LENGTH: 249
<212> TYPE: PRT
<213> ORGANISM: Artificial Sequnece
<220> FEATURE:
<223> OTHER INFORMATION: Amino acid sequence of variant enzyme N77Q

<400> SEQUENCE: 14

```
Met Phe Pro Ile Lys Lys Arg Lys Ala Ile Lys Asn Asn Asn Ile Asn
1               5                   10                  15

Ala Ala Gln Ile Pro Lys His Ile Ala Ile Met Asp Gly Asn Gly
            20                  25                  30

Arg Trp Ala Lys Gln Lys Lys Met Pro Arg Ile Lys Gly His Tyr Glu
        35                  40                  45

Gly Met Gln Thr Val Lys Lys Ile Thr Arg Tyr Ala Ser Asp Leu Gly
    50                  55                  60

Val Lys Tyr Leu Thr Leu Tyr Ala Phe Ser Thr Glu Gln Trp Ser Arg
65                  70                  75                  80

Pro Lys Asp Glu Val Asn Tyr Leu Met Lys Leu Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
    130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Glu Arg Leu Ser Asn Phe Leu
        195                 200                 205

Ile Trp Gln Cys Ser Tyr Ser Glu Phe Val Phe Ile Asp Glu Phe Trp
    210                 215                 220
```

Pro Asp Phe Asn Glu Glu Ser Leu Ala Gln Cys Ile Ser Ile Tyr Gln
225                 230                 235                 240

Asn Arg His Arg Arg Phe Gly Gly Leu
            245

<210> SEQ ID NO 15
<211> LENGTH: 750
<212> TYPE: DNA
<213> ORGANISM: Artificial Sequnece
<220> FEATURE:
<223> OTHER INFORMATION: Nucleotide sequence of variant enzyme L91G

<400> SEQUENCE: 15

```
atgtttccaa ttaagaagcg aaaagcaata aaaaataata acattaatgc ggcacaaatt    60
ccgaaacata ttgcaatcat tatggacgga atggccgat gggcaaaaca gaaaaaaatg   120
ccgcgcataa aaggacatta tgaaggcatg cagaccgtaa agaaaatcac aagatatgct   180
agtgatttag gtgtaaagta cttaacgctg tacgcatttt caactgaaaa ttggtctcgt   240
cctaaagatg aggttaatta cttgatgaaa ggaccgggtg attttttaaa cacattttta   300
ccggaactca ttgaaaaaaa tgttaaagtt gaaacgattg ctttattga tgatttaccg   360
gaccatacaa aaaagcagt gttagaagcg aaagagaaaa cgaaacataa tacaggttta   420
acgctcgtgt ttgcactgaa ttatggtggg cgtaaagaaa ttatttcagc agtgcagtta   480
atcgcagagc gttacaaatc tggtgaaatt tctttagatg aaattagtga aactcatttt   540
aatgaatatt tatttacagc aaatatgcct gatcctgagt tgttaatcag aacttccggt   600
gaagaacgtt taagtaactt tttaatttgg caatgttcat atagtgagtt tgtatttata   660
gatgaattct ggccggattt taatgaagaa agtttagcac aatgtatatc aatatatcag   720
aatcgtcatc gacgttttgg tggattataa                                    750
```

<210> SEQ ID NO 16
<211> LENGTH: 249
<212> TYPE: PRT
<213> ORGANISM: Artificial Sequnece
<220> FEATURE:
<223> OTHER INFORMATION: Amino acid sequence of variant enzyme L91G

<400> SEQUENCE: 16

Met Phe Pro Ile Lys Lys Arg Lys Ala Ile Lys Asn Asn Ile Asn
1               5                   10                  15

Ala Ala Gln Ile Pro Lys His Ile Ala Ile Ile Met Asp Gly Asn Gly
            20                  25                  30

Arg Trp Ala Lys Gln Lys Lys Met Pro Arg Ile Lys Gly His Tyr Glu
        35                  40                  45

Gly Met Gln Thr Val Lys Lys Ile Thr Arg Tyr Ala Ser Asp Leu Gly
    50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Gly Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
    130                 135                 140

```
Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Arg Leu Ser Asn Phe Leu
        195                 200                 205

Ile Trp Gln Cys Ser Tyr Ser Glu Phe Val Phe Ile Asp Glu Phe Trp
    210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245
```

<210> SEQ ID NO 17
<211> LENGTH: 750
<212> TYPE: DNA
<213> ORGANISM: Artificial Sequnece
<220> FEATURE:
<223> OTHER INFORMATION: Nucleotide sequence of variant enzyme L91K

<400> SEQUENCE: 17

```
atgtttccaa ttaagaagcg aaaagcaata aaaataata acattaatgc ggcacaaatt      60
ccgaaacata ttgcaatcat tatggacgga atggccgat gggcaaaaca gaaaaaaatg    120
ccgcgcataa aaggacatta tgaaggcatg cagaccgtaa agaaaatcac aagatatgct    180
agtgatttag gtgtaaagta cttaacgctg tacgcatttt caactgaaaa ttggtctcgt    240
cctaaagatg aggttaatta cttgatgaaa aaaccgggtg attttttaaa cacattttta    300
ccggaactca ttgaaaaaaa tgttaaagtt gaaacgattg ctttattga tgatttaccg    360
gaccatacaa aaaagcagt gttagaagcg aagagaaaa cgaaactaaa tacaggttta    420
acgctcgtgt ttgcactgaa ttatggtggg cgtaaagaaa ttatttcagc agtgcagtta    480
atcgcagagc gttacaaatc tggtgaaatt tctttagatg aaattagtga actcattttt    540
aatgaatatt tatttacagc aaatatgcct gatcctgagt tgttaatcag aacttccggt    600
gaagaacgtt taagtaactt tttaatttgg caatgttcat atagtgagtt tgtatttata    660
gatgaattct ggccggattt taatgaagaa agtttagcac aatgtatatc aatatatcag    720
aatcgtcatc gacgttttgg tggattataa                                      750
```

<210> SEQ ID NO 18
<211> LENGTH: 249
<212> TYPE: PRT
<213> ORGANISM: Artificial Sequnece
<220> FEATURE:
<223> OTHER INFORMATION: Amino acid sequence of variant enzyme L91K

<400> SEQUENCE: 18

```
Met Phe Pro Ile Lys Lys Arg Lys Ala Ile Lys Asn Asn Asn Ile Asn
1               5                   10                  15

Ala Ala Gln Ile Pro Lys His Ile Ala Ile Ile Met Asp Gly Asn Gly
            20                  25                  30

Arg Trp Ala Lys Gln Lys Lys Met Pro Arg Ile Lys Gly His Tyr Glu
        35                  40                  45

Gly Met Gln Thr Val Lys Lys Ile Thr Arg Tyr Ala Ser Asp Leu Gly
    50                  55                  60
```

Val Lys Tyr Leu Thr Leu Tyr Ala Phe Ser Thr Glu Asn Trp Ser Arg
 65                  70                  75                  80

Pro Lys Asp Glu Val Asn Tyr Leu Met Lys Lys Pro Gly Asp Phe Leu
                 85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
    130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Arg Leu Ser Asn Phe Leu
        195                 200                 205

Ile Trp Gln Cys Ser Tyr Ser Glu Phe Val Phe Ile Asp Glu Phe Trp
    210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245

<210> SEQ ID NO 19
<211> LENGTH: 750
<212> TYPE: DNA
<213> ORGANISM: Artificial Sequnece
<220> FEATURE:
<223> OTHER INFORMATION: Nucleotide sequence of variant enzyme F95A

<400> SEQUENCE: 19
atgtttccaa ttaagaagcg aaaagcaata aaaaataata acattaatgc ggcacaaatt      60
ccgaaacata ttgcaatcat tatggacgga aatggccgat gggcaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaaaa ttggtctcgt     240
cctaaagatg aggttaatta cttgatgaaa ctaccgggtg atgcattaaa cacattttta     300
ccggaactca ttgaaaaaaa tgttaaagtt gaaacgattg gctttattga tgatttaccg     360
gaccatacaa aaaagcagt gttagaagcg aaagagaaaa cgaaacataa tacaggttta     420
acgctcgtgt ttgcactgaa ttatggtggg cgtaaagaaa ttatttcagc agtgcagtta     480
atcgcagagc gttacaaatc tggtgaaatt tctttagatg aaattagtga aactcatttt     540
aatgaatatt tatttacagc aaatatgcct gatcctgagt tgttaatcag aacttccggt     600
gaagaacgtt taagtaactt tttaatttgg caatgttcat atagtgagtt tgtatttata     660
gatgaattct ggccggattt taatgaagaa agtttagcac aatgtatatc aatatatcag     720
aatcgtcatc gacgttttgg tggattataa                                       750

<210> SEQ ID NO 20
<211> LENGTH: 249
<212> TYPE: PRT
<213> ORGANISM: Artificial Sequnece
<220> FEATURE:
<223> OTHER INFORMATION: Amino acid sequence of variant enzyme F95A

<400> SEQUENCE: 20

```
Met Phe Pro Ile Lys Lys Arg Lys Ala Ile Lys Asn Asn Asn Ile Asn
 1               5                  10                  15
Ala Ala Gln Ile Pro Lys His Ile Ala Ile Met Asp Gly Asn Gly
             20                  25                  30
Arg Trp Ala Lys Gln Lys Lys Met Pro Arg Ile Lys Gly His Tyr Glu
             35                  40                  45
Gly Met Gln Thr Val Lys Lys Ile Thr Arg Tyr Ala Ser Asp Leu Gly
 50                  55                  60
Val Lys Tyr Leu Thr Leu Tyr Ala Phe Ser Thr Glu Asn Trp Ser Arg
 65                  70                  75                  80
Pro Lys Asp Glu Val Asn Tyr Leu Met Lys Leu Pro Gly Asp Ala Leu
             85                  90                  95
Asn Thr Phe Leu Pro Glu Leu Ile Glu Lys Asn Val Lys Val Glu Thr
             100                 105                 110
Ile Gly Phe Ile Asp Asp Leu Pro Asp His Thr Lys Lys Ala Val Leu
             115                 120                 125
Glu Ala Lys Glu Lys Thr Lys His Asn Thr Gly Leu Thr Leu Val Phe
 130                 135                 140
Ala Leu Asn Tyr Gly Gly Arg Lys Glu Ile Ile Ser Ala Val Gln Leu
145                 150                 155                 160
Ile Ala Glu Arg Tyr Lys Ser Gly Glu Ile Ser Leu Asp Glu Ile Ser
                165                 170                 175
Glu Thr His Phe Asn Glu Tyr Leu Phe Thr Ala Asn Met Pro Asp Pro
            180                 185                 190
Glu Leu Leu Ile Arg Thr Ser Gly Glu Arg Leu Ser Asn Phe Leu
            195                 200                 205
Ile Trp Gln Cys Ser Tyr Ser Glu Phe Val Phe Ile Asp Glu Phe Trp
210                 215                 220
Pro Asp Phe Asn Glu Glu Ser Leu Ala Gln Cys Ile Ser Ile Tyr Gln
225                 230                 235                 240
Asn Arg His Arg Arg Phe Gly Gly Leu
            245
```

<210> SEQ ID NO 21
<211> LENGTH: 750
<212> TYPE: DNA
<213> ORGANISM: Artificial Sequnece
<220> FEATURE:
<223> OTHER INFORMATION: Nucleotide sequence of variant enzyme F95W

<400> SEQUENCE: 21

```
atgtttccaa ttaagaagcg aaaagcaata aaaaataata acattaatgc ggcacaaatt      60
ccgaaacata ttgcaatcat tatggacgga atggccgat gggcaaaaca gaaaaaaatg     120
ccgcgcataa aaggacatta tgaaggcatg cagaccgtaa agaaaatcac aagatatgct    180
agtgatttag gtgtaaagta cttaacgctg tacgcatttt caactgaaaa ttggtctcgt    240
cctaaagatg aggttaatta cttgatgaaa ctaccgggtg attggttaaa cacattttta    300
ccggaactca ttgaaaaaaa tgttaaagtt gaacgattg gctttattga tgatttaccg    360
gaccatacaa aaaagcagt gttagaagcg aaagagaaaa cgaaacataa tacaggttta    420
acgctcgtgt ttgcactgaa ttatggtggg cgtaaagaaa ttatttcagc agtgcagtta    480
atcgcagagc gttacaaatc tggtgaaatt tctttagatg aaattagtga aactcatttt    540
```

```
aatgaatatt tatttacagc aaatatgcct gatcctgagt tgttaatcag aacttccggt    600
gaagaacgtt taagtaactt tttaatttgg caatgttcat atagtgagtt tgtatttata    660
gatgaattct ggccggattt taatgaagaa agtttagcac aatgtatatc aatatatcag    720
aatcgtcatc gacgttttgg tggattataa                                     750
```

<210> SEQ ID NO 22
<211> LENGTH: 249
<212> TYPE: PRT
<213> ORGANISM: Artificial Sequnece
<220> FEATURE:
<223> OTHER INFORMATION: Amino acid sequence of variant enzyme F95W

<400> SEQUENCE: 22

```
Met Phe Pro Ile Lys Lys Arg Lys Ala Ile Lys Asn Asn Ile Asn
1               5                   10                  15

Ala Ala Gln Ile Pro Lys His Ile Ala Ile Met Asp Gly Asn Gly
                20                  25                  30

Arg Trp Ala Lys Gln Lys Lys Met Pro Arg Ile Lys Gly His Tyr Glu
                35                  40                  45

Gly Met Gln Thr Val Lys Lys Ile Thr Arg Tyr Ala Ser Asp Leu Gly
50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Leu Pro Gly Asp Trp Leu
                85                  90                  95

Asn Thr Phe Leu Pro Glu Leu Ile Glu Lys Asn Val Lys Val Glu Thr
                100                 105                 110

Ile Gly Phe Ile Asp Asp Leu Pro Asp His Thr Lys Lys Ala Val Leu
            115                 120                 125

Glu Ala Lys Glu Lys Thr Lys His Asn Thr Gly Leu Thr Leu Val Phe
130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
                180                 185                 190

Glu Leu Leu Ile Arg Thr Ser Gly Glu Arg Leu Ser Asn Phe Leu
            195                 200                 205

Ile Trp Gln Cys Ser Tyr Ser Glu Phe Val Phe Ile Asp Glu Phe Trp
    210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245
```

<210> SEQ ID NO 23
<211> LENGTH: 24
<212> TYPE: DNA
<213> ORGANISM: Artificial Sequnece
<220> FEATURE:
<223> OTHER INFORMATION: Sense primer for preparation of variant enzyme N31A

<400> SEQUENCE: 23

```
gacggagcag gccgatgggc aaaa                                            24
```

<210> SEQ ID NO 24
<211> LENGTH: 25
<212> TYPE: DNA
<213> ORGANISM: Artificial Sequnece
<220> FEATURE:
<223> OTHER INFORMATION: Antisense primer for preparation of variant
      enzyme N31A

<400> SEQUENCE: 24
catcggcctg ctccgtccat aatga                                           25

<210> SEQ ID NO 25
<211> LENGTH: 25
<212> TYPE: DNA
<213> ORGANISM: Artificial Sequnece
<220> FEATURE:
<223> OTHER INFORMATION: Sense primer for preparation of variant enzyme
      N77A

<400> SEQUENCE: 25
actgaagcat ggtctcgtcc taaag                                           25

<210> SEQ ID NO 26
<211> LENGTH: 25
<212> TYPE: DNA
<213> ORGANISM: Artificial Sequnece
<220> FEATURE:
<223> OTHER INFORMATION: Antisense primer for preparation of variant
      enzyme N77A

<400> SEQUENCE: 26
gagaccatgc ttcagttgaa aatgc                                           25

<210> SEQ ID NO 27
<211> LENGTH: 26
<212> TYPE: DNA
<213> ORGANISM: Artificial Sequnece
<220> FEATURE:
<223> OTHER INFORMATION: Sense primer for preparation of variant enzyme
 L91N

<400> SEQUENCE: 27
gatgaaaaac ccgggtgatt ttttaa                                          26

<210> SEQ ID NO 28
<211> LENGTH: 26
<212> TYPE: DNA
<213> ORGANISM: Artificial Sequnece
<220> FEATURE:
<223> OTHER INFORMATION: Antisense primer for preparation of variant
      enzyme L91N

<400> SEQUENCE: 28
cacccgggtt tttcatcaag taatta                                          26

<210> SEQ ID NO 29
<211> LENGTH: 26
<212> TYPE: DNA
<213> ORGANISM: Artificial Sequnece
<220> FEATURE:
<223> OTHER INFORMATION: Sense primer for preparation of variant enzyme
      L91D

<400> SEQUENCE: 29
gatgaaagat ccgggtgatt ttttaa                                          26

<210> SEQ ID NO 30
<211> LENGTH: 26
<212> TYPE: DNA
<213> ORGANISM: Artificial Sequnece
<220> FEATURE:
<223> OTHER INFORMATION: Antisense primer for preparation of variant enzyme L91D

<400> SEQUENCE: 30
cacccggatc tttcatcaag taatta                                    26

<210> SEQ ID NO 31
<211> LENGTH: 24
<212> TYPE: DNA
<213> ORGANISM: Artificial Sequnece
<220> FEATURE:
<223> OTHER INFORMATION: Sense primer for preparation of variant enzyme N31Q

<400> SEQUENCE: 31
gacggacaag gccgatgggc aaaa                                      24

<210> SEQ ID NO 32
<211> LENGTH: 24
<212> TYPE: DNA
<213> ORGANISM: Artificial Sequnece
<220> FEATURE:
<223> OTHER INFORMATION: Antiense primer for preparation of variant enzyme N31Q

<400> SEQUENCE: 32
ccatcggcct tgtccgtcca taat                                      24

<210> SEQ ID NO 33
<211> LENGTH: 25
<212> TYPE: DNA
<213> ORGANISM: Artificial Sequnece
<220> FEATURE:
<223> OTHER INFORMATION: Sense primer for preparation of variant enzyme N77Q

<400> SEQUENCE: 33
actgaacaat ggtctcgtcc taaag                                     25

<210> SEQ ID NO 34
<211> LENGTH: 26
<212> TYPE: DNA
<213> ORGANISM: Artificial Sequnece
<220> FEATURE:
<223> OTHER INFORMATION: Antisense primer for preparation of variant enzyme N77Q

<400> SEQUENCE: 34
cgagaccatg cttcagttga aaatgc                                    26

<210> SEQ ID NO 35
<211> LENGTH: 26
<212> TYPE: DNA
<213> ORGANISM: Artificial Sequnece
<220> FEATURE:
<223> OTHER INFORMATION: Sense primer for preparation of variant enzyme L91G

<400> SEQUENCE: 35
gatgaaagga ccgggtgatt ttttaa                                    26

<210> SEQ ID NO 36

```
<211> LENGTH: 27
<212> TYPE: DNA
<213> ORGANISM: Artificial Sequnece
<220> FEATURE:
<223> OTHER INFORMATION: Antisense primer for preparation of variant
      enzyme L91G

<400> SEQUENCE: 36
acccggtcct ttcatcaagt aattaac                                      27

<210> SEQ ID NO 37
<211> LENGTH: 26
<212> TYPE: DNA
<213> ORGANISM: Artificial Sequnece
<220> FEATURE:
<223> OTHER INFORMATION: Sense primer for preparation of variant enzyme
      L91K

<400> SEQUENCE: 37
gatgaaaaaa ccgggtgatt tttttaa                                      26

<210> SEQ ID NO 38
<211> LENGTH: 26
<212> TYPE: DNA
<213> ORGANISM: Artificial Sequnece
<220> FEATURE:
<223> OTHER INFORMATION: Antisense primer for preparation of variant
      enzyme L91K

<400> SEQUENCE: 38
acccggtttt ttcatcaagt aattaa                                       26

<210> SEQ ID NO 39
<211> LENGTH: 26
<212> TYPE: DNA
<213> ORGANISM: Artificial Sequnece
<220> FEATURE:
<223> OTHER INFORMATION: Sense primer for preparation of variant enzyme
      F95A

<400> SEQUENCE: 39
gggtgatgcg ttaaacacat ttttac                                       26

<210> SEQ ID NO 40
<211> LENGTH: 26
<212> TYPE: DNA
<213> ORGANISM: Artificial Sequnece
<220> FEATURE:
<223> OTHER INFORMATION: Antisense primer for preparation of variant
      enzyme F95A

<400> SEQUENCE: 40
gtttaatgca tcacccggta gtttca                                       26

<210> SEQ ID NO 41
<211> LENGTH: 26
<212> TYPE: DNA
<213> ORGANISM: Artificial Sequnece
<220> FEATURE:
<223> OTHER INFORMATION: Sense primer for preparation of variant enzyme
      F95W

<400> SEQUENCE: 41
gggtgattgg ttaaacacat ttttac                                       26

<210> SEQ ID NO 42
<211> LENGTH: 26
```

```
<212> TYPE: DNA
<213> ORGANISM: Artificial Sequnece
<220> FEATURE:
<223> OTHER INFORMATION: Antisense primer for preparation of variant
      enzyme F95W

<400> SEQUENCE: 42
gtttaaccaa tcacccggta gtttca                                          26
```

ISOPRENE OLIGOMER, POLYISOPRENE, PROCESSES FOR PRODUCING THESE MATERIALS, RUBBER COMPOSITION, AND PNEUMATIC TIRE

This application is a Divisional of copending application Ser. No. 13/809,616, filed on Jan. 11, 2013, which was filed as PCT International Application No. PCT/JP2011/064774 on Jun. 28, 2011, which claims the benefit under 35 U.S.C. §119(a) to Patent Application No. 2010-160120, filed in Japan on Jul. 14, 2010 and Patent Application No. 2010-277384, filed in Japan on Dec. 13, 2010, all of which are hereby expressly incorporated by reference into the present application.

TECHNICAL FIELD

The present invention relates to an isoprene oligomer and a polyisoprene; processes for producing these materials; a rubber composition including the isoprene oligomer and/or the polyisoprene; and a pneumatic tire formed from the rubber composition.

BACKGROUND ART

Conventionally, in order to impart novel properties, in addition to the original properties of rubber, to rubber products, filler and the like of various materials or shapes are introduced into rubber compositions according to the uses to achieve the desired properties. For automobile tires, for example, in order to improve properties such as abrasion resistance, low-heat-build-up properties, or wet grip performance, filler (e.g., silica, carbon black) is introduced into the organic rubber fraction.

When filler or the like is mixed with the rubber fraction in such a rubber composition, for the purpose of enhancing the affinity between the two to improve low-heat-build-up properties, wet grip performance, etc., a modified rubber (modified diene polymer) has been used in which a functional group having affinity for the filler is introduced in rubber molecules in the rubber fraction as a result of, for example, a treatment involving reacting rubber molecules with, for example, a compound containing both a nitrogen atom-containing group and a chlorosulfenyl group (see, for example, Patent Literatures 1 and 2).

It is however known that, depending on methods for introduction, a predetermined functional group is difficult to introduce to a predetermined position in the rubber molecule and is consequently introduced to, particularly, a random position in the main chain constituting the rubber molecule. Use of such rubber molecules containing a predetermined functional group introduced in the main chain is less likely to produce the desired effects due to the random bonds between the rubber molecules and filler. In addition, the functional group-introduced sites have deteriorated rubber properties, which disadvantageously results in deterioration in the properties of the whole rubber.

CITATION LIST

Patent Literature

Patent Literature 1: JP 2000-001573 A
Patent Literature 2: JP 2000-001575 A

SUMMARY OF INVENTION

Technical Problem

An object of the present invention is to solve the problems described above and to provide an isoprene oligomer and a polyisoprene which have been modified substantially only at a terminal site of the molecule. Another object of the present invention is to provide a rubber composition including the isoprene oligomer and/or the polyisoprene, and pneumatic tires including various tire components (e.g., treads and sidewalls) formed from the rubber composition.

Solution to Problem

The present invention relates to an isoprene oligomer including a trans structural moiety and a cis structural moiety, which is represented by the following formula (1), wherein at least 1 atom or group in the trans structural moiety is replaced by another atom or group:

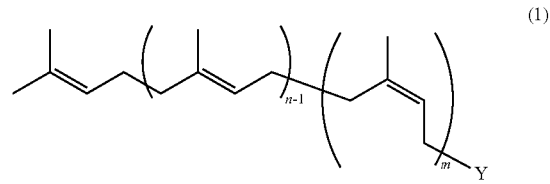

wherein n represents an integer from 1 to 10; m represents an integer from 1 to 30; and Y represents a hydroxy group, a formyl group, a carboxy group, an ester group, a carbonyl group, or a group represented by the following formula (2):

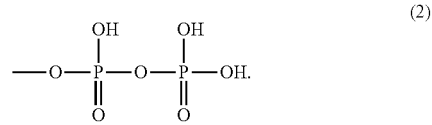

It is preferable that at least 1 atom or group in moiety II in the following formula (1-1) should be replaced, and no atom or group in moiety III should be replaced:

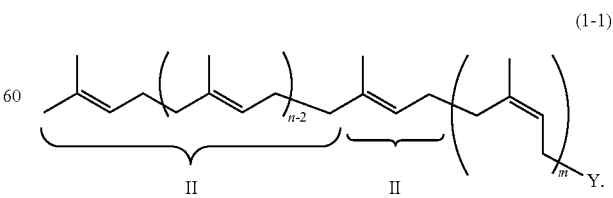

It is preferable that the trans structural moiety should be represented by any of the following formulas (a) to (s):

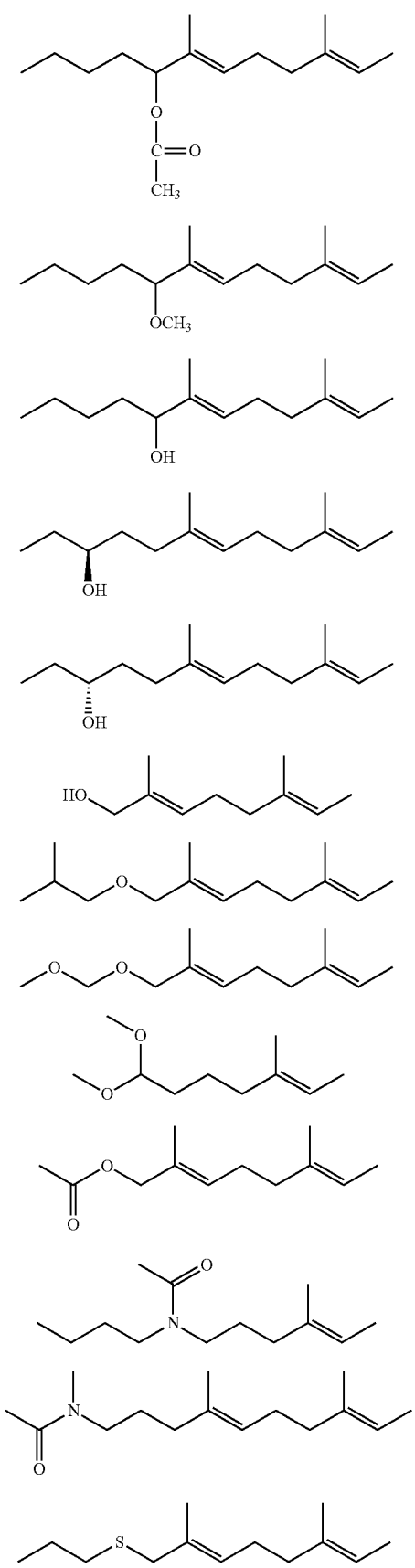

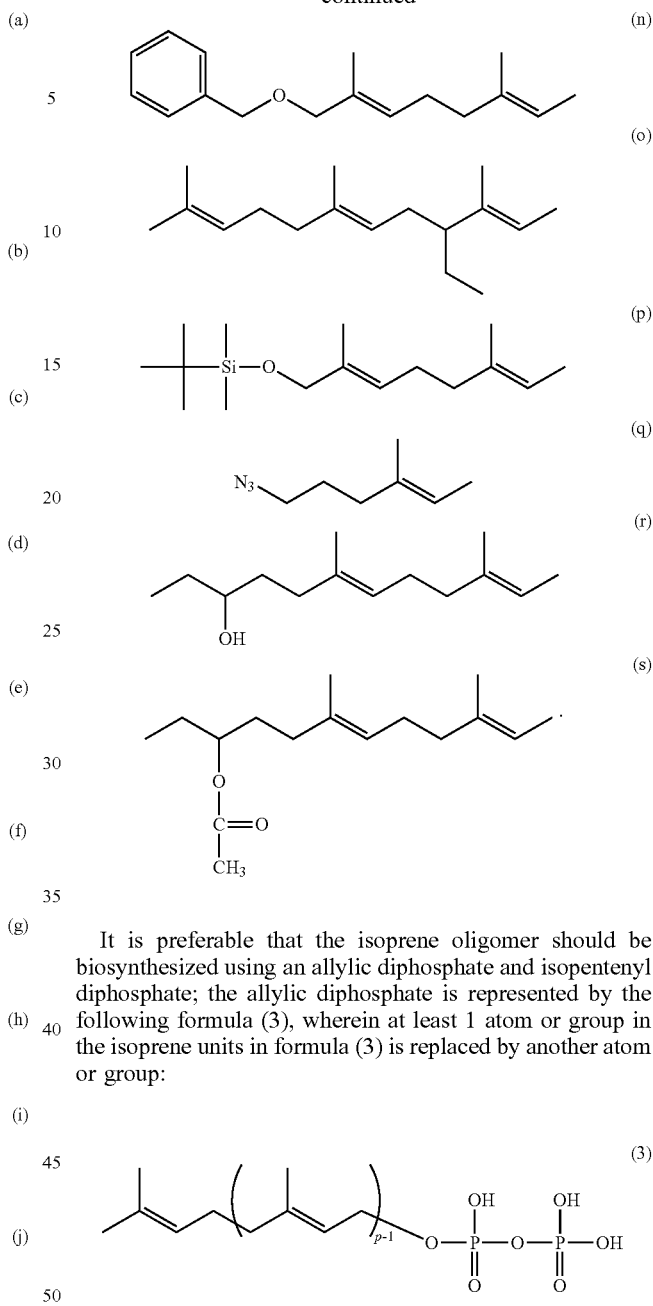

It is preferable that the isoprene oligomer should be biosynthesized using an allylic diphosphate and isopentenyl diphosphate; the allylic diphosphate is represented by the following formula (3), wherein at least 1 atom or group in the isoprene units in formula (3) is replaced by another atom or group:

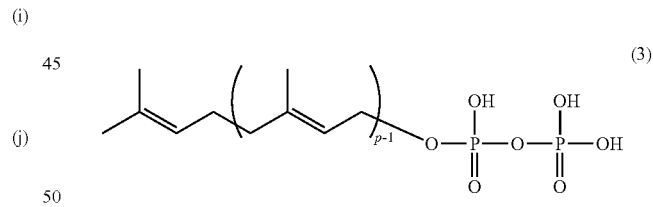

wherein p represents an integer from 1 to 10.

It is preferable that the biosynthesis should be carried out using an enzyme that shows prenyltransferase activity.

It is preferable that the enzyme that shows prenyltransferase activity should be any of the following proteins:

[1] a protein having an amino acid sequence represented by any of the following SEQ ID NOs: 2, 4, 6, 8, 10, 12, 14, 16, 18, 20, and 22;

[2] a protein having an amino sequence that is derived from the amino acid sequence represented by any of the following SEQ ID NOs: 2, 4, 6, 8, 10, 12, 14, 16, 18, 20, and 22 by substitution, deletion, insertion, or addition of 1 or more amino acids, and possessing the ability to catalyze a reaction between an allylic diphosphate and isopentenyl diphosphate, wherein the allylic diphosphate can be represented by the following formula (3), wherein at least 1 atom or group in the isoprene units in formula (3) is replaced by another atom or group;

[3] a protein having an amino acid sequence that shows 45% or higher sequence identity to the amino acid sequence represented by any of the following SEQ ID NOs: 2, 4, 6, 8, 10, 12, 14, 16, 18, 20, and 22 and possessing the ability to catalyze a reaction between an allylic diphosphate and isopentenyl diphosphate, wherein the allylic diphosphate can be represented by the following formula (3), wherein at least 1 atom or group in the isoprene units in formula (3) is replaced by another atom or group:

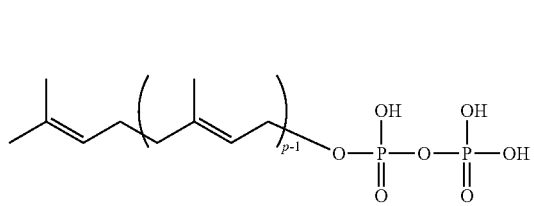

(3)

wherein p represents an integer from 1 to 10.

The present invention also relates to a process for producing the isoprene oligomer, which involves the biosynthesis of isoprene oligomer by using an allylic diphosphate and isopentenyl diphosphate, wherein the allylic diphosphate can be represented by the following formula (3), wherein at least 1 atom or group in the isoprene units in formula (3) is replaced by another atom or group:

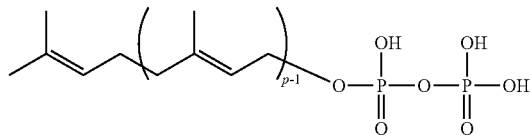

(3)

wherein p represents an integer from 1 to 10.

It is preferable that the biosynthesis should be carried out using an enzyme showing prenyltransferase activity.

The present invention further relates to a polyisoprene including a trans structural moiety and a cis structural moiety, which is represented by the following formula (4), wherein at least 1 atom or group in the trans structural moiety is replaced by another atom or group:

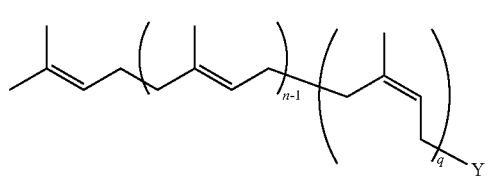

(4)

wherein n represents an integer from 1 to 10; q represents an integer from 30 to 40 000; and Y represents a hydroxy group, a formyl group, a carboxy group, an ester group, a carbonyl group, or a group represented by the following formula (2):

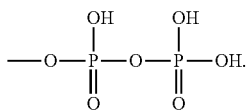

(2)

It is preferable that at least 1 atom or group in moiety VI in the following formula (4-1) should be replaced, and no atom or group in moiety VII should be replaced:

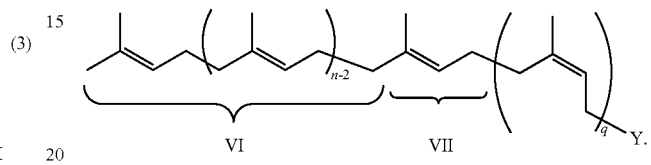

(4-1)

It is preferable that the polyisoprene should be biosynthesized using the isoprene oligomer and isopentenyl diphosphate.

The present invention further relates to a process for producing the polyisoprene, which involves the biosynthesis of the polyisoprene by using the isoprene oligomer and isopentenyl diphosphate.

The present invention further relates to a rubber composition including at least 1 of the isoprene oligomers and the polyisoprene.

The present invention further relates to a pneumatic tire formed from the rubber composition.

Advantageous Effects of Invention

The isoprene oligomer of the present invention is an isoprene oligomer containing a trans structural moiety and a cis structural moiety represented by the formula (1), wherein at least one atom or group contained in the trans structural moiety is replaced by another atom or group. Moreover, the polyisoprene of the present invention is a polyisoprene containing a trans structural moiety and a cis structural moiety represented by the formula (4), wherein at least one atom or group contained in the trans structural moiety is replaced by another atom or group. Thus, the isoprene oligomer of the present invention and the polyisoprene of the present invention have been modified substantially only at a terminal site of the molecule (rubber molecule) and therefore are excellent in affinity for filler such as silica while the original properties of the molecules (rubber molecules) are not impaired. Accordingly, a rubber composition containing the isoprene oligomer of the present invention and/or the polyisoprene of the present invention is obtained as a rubber composition in which rubber molecules are combined with filler in a level higher than ever. Thus, the present invention can provide a rubber composition excellent in, for example, low-heat-build-up properties, and wet grip performance. Use of the rubber composition in various tire components (e.g., treads and sidewalls) can provide pneumatic tires excellent in, for example, low-heat-build-up properties, and wet grip performance.

DESCRIPTION OF EMBODIMENTS

In the process of artificially biosynthesizing a rubber molecule (polyisoprene), an enzyme such as prenyltransferase is allowed to act on a mixture of an initiating substrate such as farnesyl diphosphate (FPP) and monomer such as isopentenyl diphosphate to produce an isoprene oligomer having approximately 8 isoprene units addition-polymerized to the initiating substrate. It is known that the isoprene oligomer is then further mixed with a latex component containing an enzyme for addition-polymerizing isopentenyl diphosphate to produce a polyisoprene having a large number of isopentenyl diphosphate units linked to the oligomer.

As described above, the addition polymerization mediated by natural enzymes is indispensable to various steps for sequentially linking the monomers starting from the initiating substrate to form a rubber molecule.

For this reason, the biosynthesis of a rubber molecule (polyisoprene) requires using an initiating substrate and monomer whose reaction can be catalyzed by the enzyme used, which results in limitations to the structures of the initiating substrate and monomer used as raw materials for the rubber molecule (polyisoprene). Particularly, the initiating substrate is limited to naturally occurring dimethylallyl diphosphate, geranyl diphosphate, farnesyl diphosphate, geranylgeranyl diphosphate, and the like due to restrictions attributed to the enzyme for producing the oligomer.

As a result, the artificially biosynthesized rubber molecule (polyisoprene) is also limited in the degree of freedom of its structure. Thus, free molecular design for imparting functionality that is absent in natural rubber is made difficult.

Conventionally, in order to obtain, for example, a rubber molecule (polyisoprene) in which a functional group or the like is introduced, a functional group having affinity for filler is introduced into a rubber molecule, for example, by a treatment including reacting a rubber molecule (polyisoprene) biosynthesized in advance with, for example, a compound containing both a nitrogen atom-containing group and a chlorosulfenyl group, similarly as in the case of using synthetic rubber as a raw material.

In contrast, the present invention is based on the findings that an isoprene oligomer or polyisoprene having a terminal site to which functionality has been imparted can be produced by using partially structurally modified farnesyl diphosphate or the like as an initiating substrate for the isoprene oligomer or polyisoprene production.

In particular, the present invention is based on the findings that by maintaining the structure of moiety I in the following formula (I) in the naturally occurring initiating substrate farnesyl diphosphate or the like, even when a desired structure is introduced in a moiety other than moiety I, it is possible to produce isoprene oligomers in the presence of the naturally occurring oligomer-producing enzyme prenyltransferase or any enzyme obtained by partial mutation thereof. This is probably, albeit not absolutely clear, because prenyltransferase is adsorbed on the structure of moiety I in the formula (I) of the initiating substrate and is relatively insensitive to the structures of other moieties.

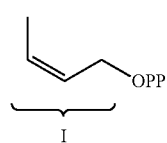

(I)

On the basis of these findings, an isoprene oligomer or polyisoprene having a terminal site having desired properties can be provided. In other words, isoprene oligomers or polyisoprenes having various functions can be provided without impairing the properties of isoprene oligomer or polyisoprene itself.

(Isoprene Oligomer)

The isoprene oligomer of the present invention is an isoprene oligomer containing a trans structural moiety and a cis structural moiety represented by the formula (1) shown below, wherein at least one atom or group contained in the trans structural moiety is replaced by another atom or group. In this context, the trans structural moiety means a moiety of repeated isoprene units with a trans structure (moiety A in the formula (1) shown below). Also, the cis structural moiety means a moiety of repeated isoprene units with a cis structure (moiety $(\ )_m$ (moiety B) in the formula (1) shown below). In the present specification, the group represented by the formula (2) shown below has three hydroxy groups bonded to a phosphorus atom, and some (or one) or all of these hydroxy groups are dissociated in an aqueous solution (for example, a group represented by the formula (5) shown below is then formed). In the present specification, the group represented by the formula (2) also conceptually encompasses such groups in which some (or one) or all of the hydroxy groups have been dissociated.

In the present specification, the modification of a terminal site of the molecule (rubber molecule) refers to the introduction of a desired functional group into a predetermined site in the trans structural moiety present at an end of the molecule (rubber molecule), or the introduction of a different structure into a predetermined site in the trans structural moiety present at an end of the molecule (rubber molecule).

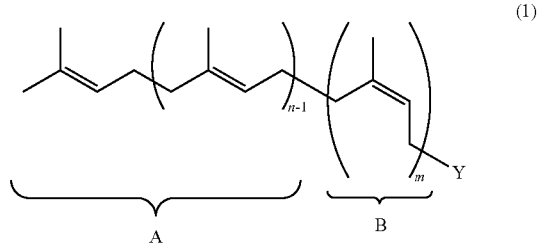

(1)

wherein n represents an integer of 1 to 10; m represents an integer of 1 to 30; and Y represents a hydroxy group, a formyl group, a carboxy group, an ester group, a carbonyl group, or a group represented by the following formula (2).

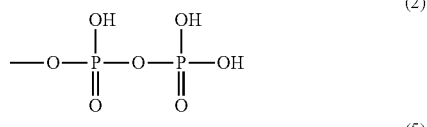

(2)

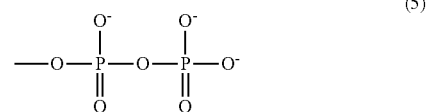

(5)

The isoprene oligomer of the present invention is structurally similar to natural rubber and is highly compatible with rubber molecules. Moreover, the isoprene oligomer of the present invention has been modified substantially only at a terminal site of the molecule. Specifically, the isoprene oligomer of the present invention contains a hydroxy group, a formyl group, a carboxy group, an ester group, a carbonyl group, or a group represented by the formula (2), positioned at the end of the cis structural moiety, and at least one atom or group contained in the trans structural moiety is replaced by another atom or group. Thus, the isoprene oligomer of the present invention strongly interacts with filler such as silica while the original properties of isoprene oligomer are not impaired. Since the isoprene oligomer of the present invention is highly compatible with rubber and strongly interacts with filler such as silica, as described above, a rubber composition containing this isoprene oligomer is obtained as a rubber composition in which rubber molecules are combined with filler in a level higher than ever. The resulting rubber composition can have, for example, improved low-heat-build-up properties, wet grip performance, and abrasion resistance.

The isoprene oligomer of the present invention contains a polar group or the like only at the terminal site of the cis structural moiety and a site close to the end of the trans structural moiety. The isoprene oligomer therefore offers high dispersibility of filler such as silica and has a large effect of improving, for example, low-heat-build-up properties, wet grip performance, and abrasion resistance while the original properties of isoprene oligomer are not impaired, compared with isoprene oligomers containing a polar group or the like in the main chain moiety or only at the terminal site of the cis structural moiety.

Furthermore, the isoprene oligomer of the present invention has excellent antimicrobial activity. This is presumably because the isoprene oligomer of the present invention, in which at least one atom or group contained in the trans structural moiety is replaced by another atom or group, structurally differs from usual isoprene oligomers present in the natural world and thus has effects such as the inhibition of enzymes or coenzymes, the inhibition of nucleic acid synthesis, the inhibition of cell membrane synthesis, the inhibition of cytoplasmic membrane synthesis, cell membrane disruption, and cytoplasmic membrane disruption in microbes.

In the formula (1), n represents an integer of 1 to 10 (preferably 1 to 4, more preferably 1 to 3).

In the formula (1), m represents an integer of 1 to 30 (preferably 1 to 10, more preferably 1 to 8).

In the formula (1), Y represents a hydroxy group (—OH), a formyl group (—CHO), a carboxy group (—COOH), an ester group (—COOR), a carbonyl group (—COR), or a group represented by the formula (2).

In the ester group (—COOR) or the carbonyl group (—COR), R represents an alkyl group having 1 to 30 (preferably 1 to 17) carbon atoms. Examples of the alkyl group having 1 to 30 carbon atoms include methyl, ethyl, propyl, butyl, and pentyl groups.

In the formula (1), Y is preferably a hydroxy group or a carboxy group, because the resulting isoprene oligomer has excellent antimicrobial properties and strongly interacts with filler such as silica.

At least one atom or group contained in the trans structural moiety in the formula (1) has been replaced by another atom or group.

Examples of the atom or group (atom or group before replacement) contained in the trans structural moiety include a hydrogen atom, a methyl group, a methylene group, a carbon atom, and a methine group.

Examples of the another atom include nitrogen, oxygen, sulfur, silicon, and carbon atoms. Among them, a nitrogen atom has a strong intermolecular force and causes strong interaction with enzymes or cell membranes. For this reason, a nitrogen atom is preferred in terms of antimicrobial properties.

Examples of the another group include an acetoxy group, alkoxy groups (preferably, alkoxy groups having 1 to 3 carbon atoms, more preferably a methoxy group), a hydroxy group, aryl groups (preferably, a phenyl group), alkyl groups (preferably, alkyl groups having 1 to 5 carbon atoms, more preferably an ethyl group and a tert-butyl group), an acetyl group, N-alkyl-acetamino groups (whose alkyl preferably has 1 to 5 carbon atoms), and an azide group.

Particularly, since a nitrogen atom has a strong intermolecular force and causes strong interaction with enzymes or cell membranes, N-alkyl-acetamino groups (more preferably, N-methyl-acetamino and N-butyl-acetamino groups) and azide group are preferred in terms of antimicrobial properties.

As described above, at least one atom or group contained in the trans structural moiety has been replaced by another atom or group. For this replacement, it is preferable that in the moiety of repeated isoprene units in the trans structural moiety, at least one atom or group contained in moiety II in the formula (1-1) shown below should be replaced while no atom or group contained in moiety III in the formula (1-1) should be replaced. This is based on the findings by the present inventors that by maintaining the structure of moiety I in the formula (I) in the naturally occurring initiating substrate farnesyl diphosphate or the like, even when a desired structure is introduced in a moiety other than moiety I, it is possible to produce isoprene oligomers in the presence of the naturally occurring oligomer-producing enzyme prenyltransferase or any enzyme obtained by partial mutation thereof.

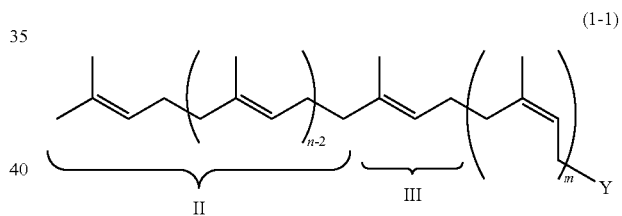

(1-1)

wherein n, m, and Y are as defined for n, m, and Y in the formula (1).

Specific examples of the trans structural moiety in the formula (1) include structures represented by the formulas (a) to (s) shown below. Among them, structures represented by the formulas (c), (d), (e), (f), (k), (l), and (r) are preferred, because the resulting isoprene oligomer has a large effect of improving low-heat-build-up properties, wet grip performance, and abrasion resistance. Also, structures represented by the formulas (g) to (q) are preferred, with structures represented by the formulas (k), (l), and (q) being more preferred, because the resulting isoprene oligomer is excellent in antimicrobial properties.

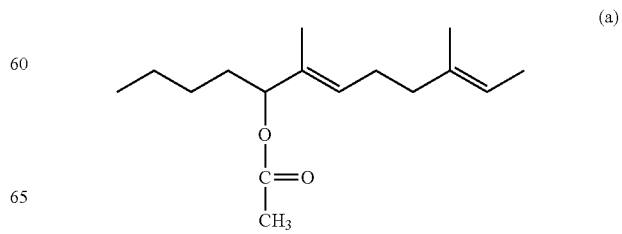

(a)

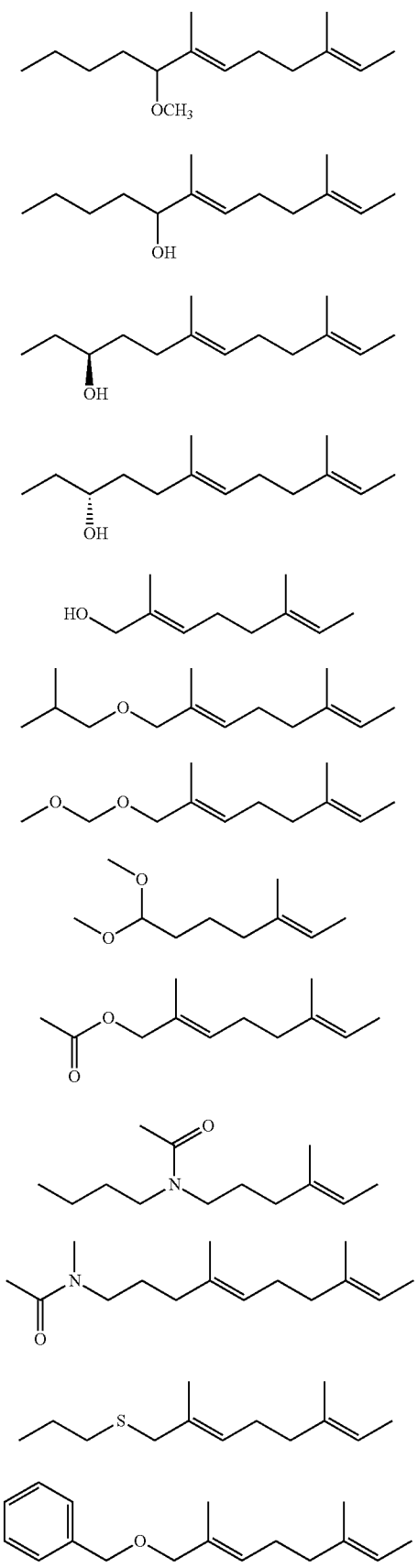
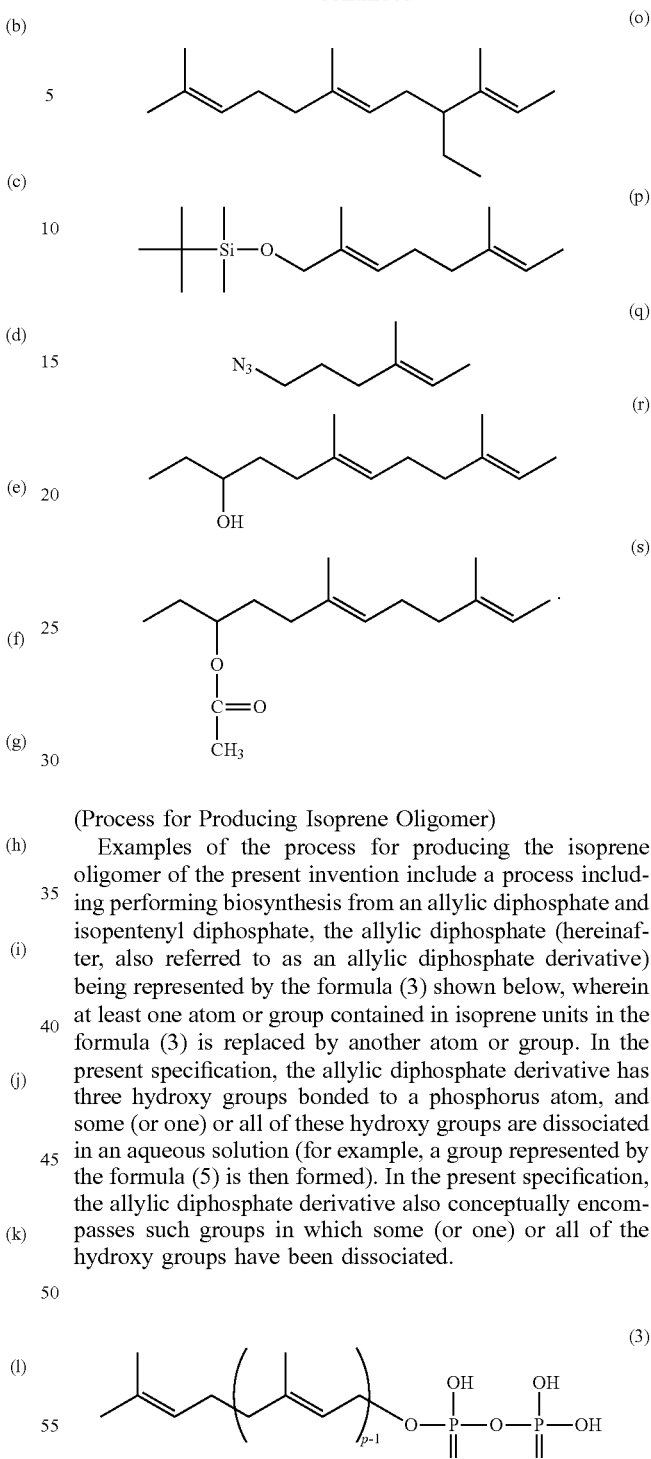

(Process for Producing Isoprene Oligomer)

Examples of the process for producing the isoprene oligomer of the present invention include a process including performing biosynthesis from an allylic diphosphate and isopentenyl diphosphate, the allylic diphosphate (hereinafter, also referred to as an allylic diphosphate derivative) being represented by the formula (3) shown below, wherein at least one atom or group contained in isoprene units in the formula (3) is replaced by another atom or group. In the present specification, the allylic diphosphate derivative has three hydroxy groups bonded to a phosphorus atom, and some (or one) or all of these hydroxy groups are dissociated in an aqueous solution (for example, a group represented by the formula (5) is then formed). In the present specification, the allylic diphosphate derivative also conceptually encompasses such groups in which some (or one) or all of the hydroxy groups have been dissociated.

wherein p represents an integer of 1 to 10.

In the formula (3), p represents an integer of 1 to 10 (preferably 1 to 4, more preferably 1 to 3).

In the present specification, examples of the atom or group (atom or group before replacement) contained in isoprene units in the formula (3) include the same as those exemplified as the atom or group (atom or group before replacement) contained in the trans structural moiety in the formula (1).

In the present specification, examples of the another atom or group for replacing the atom or group contained in isoprene units in the formula (3) include the same as those exemplified as the another atom or the another group described for the formula (1).

For the replacement, it is preferable that the structure of moiety I in the formula (I) should be maintained after the replacement, as described above. Specifically, it is preferable that at least one atom or group contained in moiety IV in the formula (3-1) shown below should be replaced while no atom or group contained in moiety V in the formula (3-1) should be replaced. This allows favorable production of isoprene oligomers using the naturally occurring oligomer-producing enzyme prenyltransferase or any enzyme obtained by partial mutation thereof.

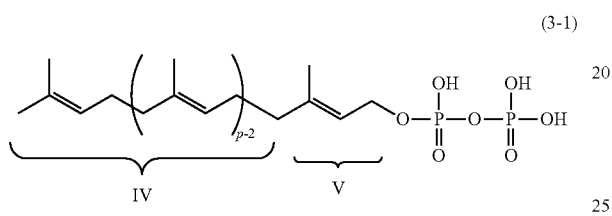

(3-1)

wherein p is as defined for p in the formula (3).

Specific examples of the allylic diphosphate derivative include compounds represented by the following formulas (A) to (S).

(A)

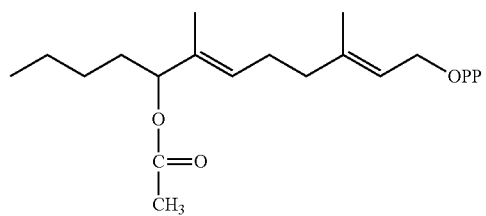

(B)

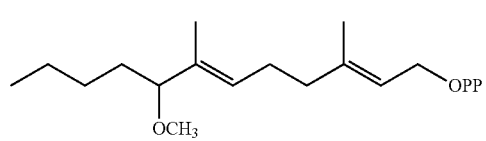

(C)

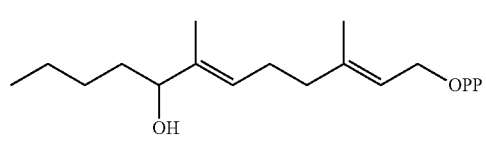

(D)

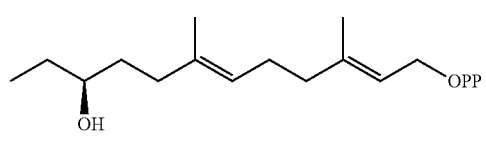

(E)

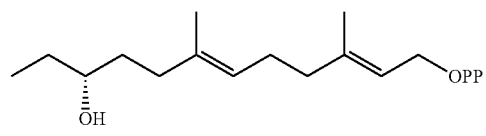

(F)

(G)

(H)

(I)

(J)

(K)

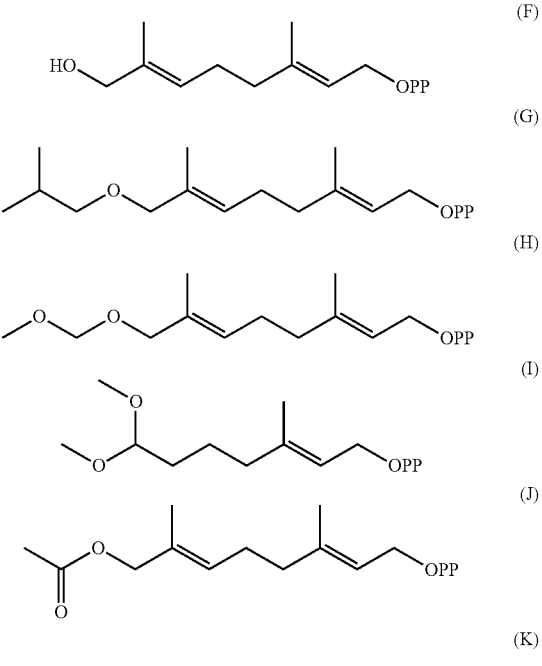

(L)

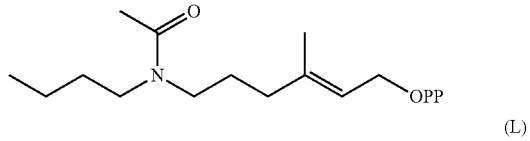

(M)

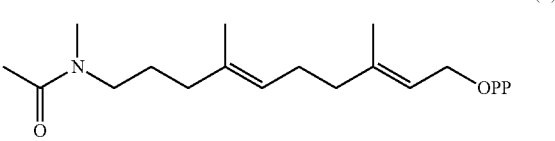

(N)

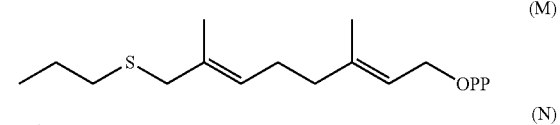

(O)

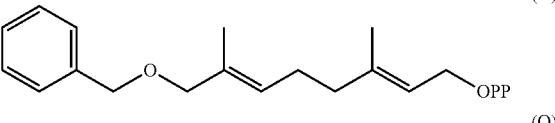

(P)

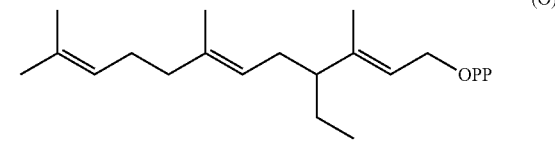

(Q)

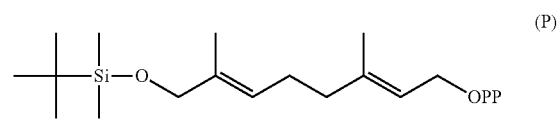

(R)

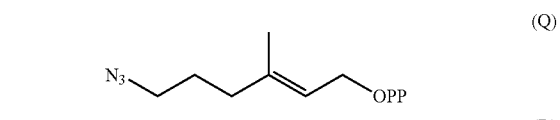

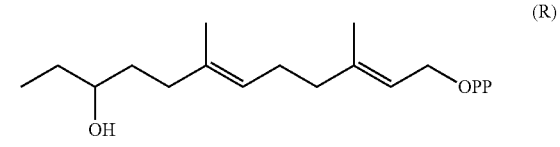

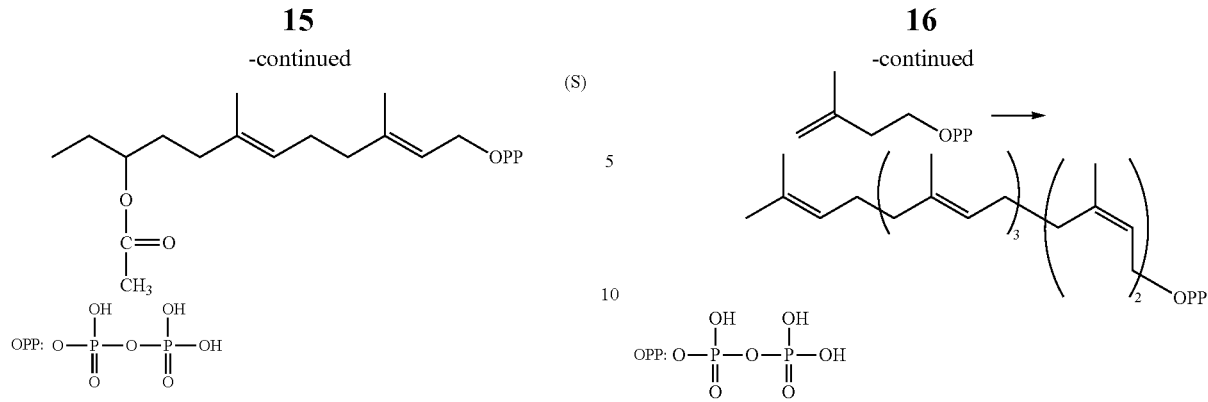

In the present specification, OPP has three hydroxy groups bonded to a phosphorus atom, and some (or one) or all of these hydroxy groups are dissociated in an aqueous solution (for example, a group represented by the formula (5) is then formed). In the present specification, OPP also conceptually encompasses such groups in which some (or one) or all of the hydroxy groups have been dissociated.

Allylic diphosphate derivatives represented by the formulas (A) to (S) and the like can be produced by those skilled in the art with reference to the processes described in Examples, using, for example, dimethylallyl diphosphate, geranyl diphosphate, farnesyl diphosphate, geranylgeranyl diphosphate, geraniol, farnesol, or geranylgeraniol.

Examples of the process for biosynthesizing the isoprene oligomer of the present invention from the allylic diphosphate derivative and isopentenyl diphosphate include a process using an enzyme having prenyltransferase activity. Specifically, the allylic diphosphate derivative and isopentenyl diphosphate may be allowed to react with each other in the presence of an enzyme having prenyltransferase activity.

In the present specification, the enzyme having prenyltransferase activity means an enzyme having activity of catalyzing the condensation reaction between an allylic substrate (allylic diphosphate) and isopentenyl diphosphate to synthesize a new allylic diphosphate in which one isoprene unit is added, and catalyzing a reaction through which isopentenyl diphosphate is sequentially linked in a Z form (newly added isoprene unit has a cis structure) starting from the allylic substrate (allylic diphosphate). Examples thereof include enzymes for catalyzing the following reaction:

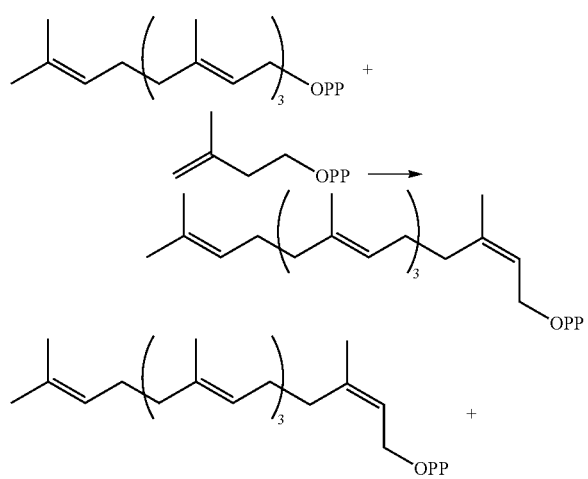

The presence of many such enzymes having prenyltransferase activity has already been confirmed (e.g., Z-nonaprenyl diphosphate synthase (Ishii, K. et al., (1986) Biochem, J., 233, 773) and undecaprenyl diphosphate (UPP) synthase (Takahashi, I. and Ogura, K. (1982) J. Biochem., 92, 1527; and Keenman, M. V. and Allen, C. M. (1974) Arch. Biochem. Biophys., 161, 375)). Since the maximum number of isoprene units (m in the formula (1)) each enzyme can produce is predetermined, the enzyme to be used can be changed according to the number of isoprene units (m in the formula (1)) of interest.

Examples of organisms containing the enzyme having prenyltransferase activity include *Micrococcus luteus* B-P 26, *Escherichia coli, Saccharomyces cerevisiae, Arabidopsis thaliana, Hevea brasiliensis, Periploca sepium, Bacillus Stearothermophilus*, and *Sulfolobus acidocaldarius* (ATCC49426).

The isoprene oligomer of the present invention can be obtained by reacting the allylic diphosphate derivative with isopentenyl diphosphate in the presence of the enzyme having prenyltransferase activity. The phrase "in the presence of the enzyme having prenyltransferase activity" means the presence of a culture of the organism, biological cells separated from the culture, a treated product of the biological cells, the enzyme purified from the culture or the biological cells, a culture of biological cells (transformant) transformed by a genetic engineering approach so as to express the enzyme having prenyltransferase activity (this enzyme also encompasses variant enzymes described later), biological cells separated from the culture, a treated product of the biological cells, the enzyme purified from the culture or the biological cells, or the like.

In this context, the biological cells transformed so as to express the enzyme having prenyltransferase activity refer to a transformant prepared by a genetic engineering approach conventionally known in the art. The preparation method will be described later.

In order to obtain biological cells of the organism, the organism can be cultured in an appropriate medium. The medium for this purpose is not particularly limited as long as the organism can proliferate therein. A usual medium containing usual carbon source, nitrogen source and inorganic ions, and optionally organic nutrient sources can be used.

For example, any carbon sources that can be utilized by the organism can be used. Specific examples of usable carbon sources include: sugars such as glucose, fructose, maltose, and amylose; alcohols such as sorbitol, ethanol, and glycerol; organic acids such as fumaric acid, citric acid, acetic acid, and propionic acid, and salts thereof; carbohydrates such as paraffin; and mixtures thereof.

Examples of usable nitrogen sources include: inorganic ammonium salts such as ammonium sulfate and ammonium chloride; ammonium salts of organic acids such as ammonium fumarate and ammonium citrate; nitrates such as sodium nitrate and potassium nitrate; organic nitrogen compounds such as peptone, yeast extracts, meat extracts, and corn steep liquor; and mixtures thereof.

In addition, nutrient sources used in usual media, such as inorganic salts, trace metal salts, vitamins, and hormones, can be mixed appropriately for use.

The culture conditions are not particularly limited and culture can be performed at pH and temperature appropriately controlled in the ranges of pH 5 to 8 and temperature 20 to 60° C., for approximately 12 to 480 hours under aerobic conditions.

Examples of the culture of the organism include a culture solution obtained by culturing the organism under the culture conditions described above, and a culture filtrate (culture supernatant) obtained by separating the organism (biological cells) from the culture solution by filtration or the like. Also, examples of the biological cells separated from the culture include biological cells (organism) separated from the culture solution by filtration, centrifugation, or the like.

Examples of the treated product of the biological cells include disrupted biological cells obtained by homogenizing the biological cells separated from the culture, and disrupted biological cells obtained by sonicating the biological cells separated from the culture.

The enzyme purified from the culture or the biological cells may be obtained, for example, by a known purification operation, such as salting out, ion-exchange chromatography, affinity chromatography, or gel-filtration chromatography, for the enzyme present in the culture or the biological cells. The purified enzyme is not particularly limited in its purity.

As described above, the isoprene oligomer of the present invention can be obtained by reacting the allylic diphosphate derivative with isopentenyl diphosphate in the presence of the enzyme having prenyltransferase activity. Specifically, for example, the culture of the biological cells, the purified enzyme or the like can be added into a solution containing the allylic diphosphate derivative and isopentenyl diphosphate to perform the reaction. The reaction temperature can be set to, for example, 20 to 60° C.; the reaction time can be set to, for example, 1 to 16 hours; and the pH can be set to, for example, 5 to 8. If necessary, magnesium chloride, a surfactant, 2-mercaptoethanol, and the like may further be added thereto.

The isoprene oligomer of the present invention obtained by the reaction is usually represented by the formula (1) wherein Y is a group represented by the formula (2) or a hydroxy group. This hydroxy group is formed through the hydrolysis of the group represented by the formula (2).

Further, the isoprene oligomer represented by the formula (1) wherein Y is a formyl group can be obtained, for example, by the oxidation of the isoprene oligomer of the formula (1) wherein Y is a group represented by the formula (2).

Further, the isoprene oligomer represented by the formula (1) wherein Y is a carboxy group can be obtained, for example, by the oxidation of the isoprene oligomer of the formula (1) wherein Y is a group represented by the formula (2).

Further, the isoprene oligomer represented by the formula (1) wherein Y is an ester group can be obtained, for example, by the oxidation and esterification of the isoprene oligomer of the formula (1) wherein Y is a group represented by the formula (2).

Further, the isoprene oligomer represented by the formula (1) wherein Y is a carbonyl group can be obtained, for example, by the oxidation and esterification of the isoprene oligomer of the formula (1) wherein Y is a group represented by the formula (2).

The isoprene oligomer of the present invention is obtained by biosynthesis except for the organic synthesis of the allylic diphosphate derivative as an initiating substrate, and can thus take into account the exhaustion of petroleum resources and environmental issues.

(Enzyme Having Prenyltransferase Activity)

Next, the enzyme having prenyltransferase activity will be described.

As an example of the enzyme having prenyltransferase activity derived from the organism, the base sequence and the amino acid sequence of *Micrococcus luteus* B-P 26 (available from Dr. L. Jeffries, Walton Oaks Experimental Station Vitamins, Ltd.)-derived undecaprenyl diphosphate synthase are shown in SEQ ID NOs: 1 and 2, respectively, in the Sequence Listing. The base sequence and the amino acid sequence of *Micrococcus luteus* B-P 26-derived undecaprenyl diphosphate synthase are known in the art and included in the database DDBJ (DNA Data Bank of Japan) (Accession No. AB004319 (base sequence) and Accession No. BAA31993.1 (amino acid sequence)).

The original substrate (initiating substrate) for the enzyme (enzyme having prenyltransferase activity) derived from this organism is an allylic diphosphate. Then, the allylic diphosphate derivative used as an initiating substrate in the present invention originally functions as an inhibitor of the enzyme produced by the organism. Thus, the enzyme produced by the organism often has low enzymatic activity on the allylic diphosphate derivative (particularly, the compound represented by any of the formulas (G) to (Q)). Therefore, in the present invention, it is preferable to use a variant enzyme having enhanced enzymatic activity on the allylic diphosphate derivative.

In the case of using the variant enzyme, biological cells (transformant) transformed by a genetic engineering approach so as to express the variant enzyme can be prepared.

The present inventors have prepared variant enzymes of the *Micrococcus luteus* B-P 26-derived undecaprenyl diphosphate synthase and successfully enhanced the enzymatic activity on the allylic diphosphate derivative.

The three-dimensional structure of the *Micrococcus luteus* B-P 26-derived undecaprenyl diphosphate synthase has already been known in the art (database PDB (RCSB Protein Data Bank), ID: 1f75). Thus, the present inventors have conducted docking simulation based on this three-dimensional structure information and prepared variant enzymes on the basis of the design philosophy that the enzymatic activity on the allylic diphosphate derivative can be enhanced by mutation of an amino acid positioned in the vicinity of the hydrocarbon moiety around the diphosphate moiety of the allylic diphosphate so as to change the length of the side chain or the charge. Specifically, it is preferable to perform any of the following mutations (1) to (4):

(1) Substitution of asparagine at position 31 by alanine, glutamine, glycine, or aspartic acid;

(2) Substitution of leucine at position 91 by asparagine, aspartic acid, glycine, or lysine;

(3) Substitution of asparagine at position 77 by alanine, glutamine, glycine, or aspartic acid;

(4) Substitution of phenylalanine at position 95 by alanine, tryptophan, glycine, aspartic acid, or arginine.

Specifically, the following variant enzymes were prepared:

variant enzyme N31A: asparagine at position 31 was substituted by alanine (its base sequence and amino acid sequence are shown in SEQ ID NOs: 3 and 4, respectively, in the Sequence Listing);

variant enzyme N77A: asparagine at position 77 was substituted by alanine (its base sequence and amino acid sequence are shown in SEQ ID NOs: 5 and 6, respectively, in the Sequence Listing);

variant enzyme L91N: leucine at position 91 was substituted by asparagine (its base sequence and amino acid sequence are shown in SEQ ID NOs: 7 and 8, respectively, in the Sequence Listing);

variant enzyme L91D: leucine at position 91 was substituted by aspartic acid (its base sequence and amino acid sequence are shown in SEQ ID NOs: 9 and 10, respectively, in the Sequence Listing);

variant enzyme N31Q: asparagine at position 31 was substituted by glutamine (its base sequence and amino acid sequence are shown in SEQ ID NOs: 11 and 12, respectively, in the Sequence Listing);

variant enzyme N77Q: asparagine at position 77 was substituted by glutamine (its base sequence and amino acid sequence are shown in SEQ ID NOs: 13 and 14, respectively, in the Sequence Listing);

variant enzyme L91G: leucine at position 91 was substituted by glycine (its base sequence and amino acid sequence are shown in SEQ ID NOs: 15 and 16, respectively, in the Sequence Listing);

variant enzyme L91K: leucine at position 91 was substituted by lysine (its base sequence and amino acid sequence are shown in SEQ ID NOs: 17 and 18, respectively, in the Sequence Listing);

variant enzyme F95A: phenylalanine at position 95 was substituted by alanine (its base sequence and amino acid sequence are shown in SEQ ID NOs: 19 and 20, respectively, in the Sequence Listing);

variant enzyme F95W: phenylalanine at position 95 was substituted by tryptophan (its base sequence and amino acid sequence are shown in SEQ ID NOs: 21 and 22, respectively, in the Sequence Listing).

Among them, variant enzyme N77A, variant enzyme L91D, and variant enzyme L91K are preferred.

Although the use of the *Micrococcus luteus* B-P 26-derived undecaprenyl diphosphate synthase as a wild-type enzyme is described herein, variant enzymes can be prepared by similar approaches using other enzymes having prenyltransferase activity as wild-type enzymes.

Specific examples of the enzyme having prenyltransferase activity include the following protein [1]:

[1] a protein having an amino acid sequence represented by any of SEQ ID NOs: 2, 4, 6, 8, 10, 12, 14, 16, 18, 20, and 22.

It is also known that enzymes having an amino acid sequence derived from the original amino acid sequence by substitution, deletion, insertion, or addition of one or more amino acids may have enzymatic activity. Thus, specific examples of the enzyme having prenyltransferase activity also include the following protein [2]:

[2] a protein having an amino acid sequence derived from the amino acid sequence represented by any of SEQ ID NOs: 2, 4, 6, 8, 10, 12, 14, 16, 18, 20, and 22 by substitution, deletion, insertion, or addition of one or more amino acids, and having activity of catalyzing a reaction between an allylic diphosphate (allylic diphosphate derivative) and isopentenyl diphosphate, the allylic diphosphate being represented by the following formula (3), wherein at least one atom or group contained in isoprene units in the formula (3) is replaced by another atom or group:

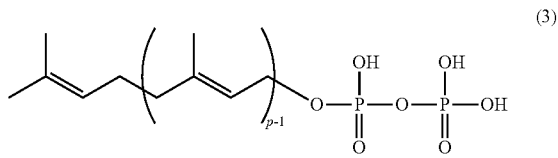

wherein p represents an integer of 1 to 10.

For maintaining the activity of catalyzing the reaction between the allylic diphosphate derivative and isopentenyl diphosphate, it is preferable that the amino acid sequence should contain substitution, deletion, insertion, or addition of preferably one or more amino acids, more preferably 1 to 100 amino acids, even more preferably 1 to 75 amino acids, particularly preferably 1 to 50 amino acids, further preferably 1 to 25 amino acids, further preferably 1 to 12 amino acids, further preferably 1 to 5 amino acids, and most preferably 1 to 3 amino acids.

It is also known that proteins having an amino acid sequence having high sequence identity to the amino acid sequence of the enzyme having prenyltransferase activity may have similar activity. Thus, specific examples of the enzyme having prenyltransferase activity also include the following protein [3]:

[3] a protein having an amino acid sequence having 45% or higher sequence identity to the amino acid sequence represented by any of SEQ ID NOs: 2, 4, 6, 8, 10, 12, 14, 16, 18, 20, and 22, and having activity of catalyzing a reaction between the allylic diphosphate derivative and isopentenyl diphosphate.

For maintaining the activity of catalyzing the reaction between the allylic diphosphate derivative and isopentenyl diphosphate, the sequence identity to the amino acid sequence represented by any of SEQ ID NOs: 2, 4, 6, 8, 10, 12, 14, 16, 18, 20, and 22 is preferably 45% or higher, more preferably 60% or higher, even more preferably 70% or higher, particularly preferably 80% or higher, further preferably 90% or higher, further preferably 95% or higher, further preferably 98% or higher, and most preferably 99% or higher.

The amino acid sequence or base sequence identity can be determined using the algorithm BLAST by Karlin and Altschul [Pro. Natl. Acad. Sci. USA, 90, 5873 (1993)] or FASTA [Methods Enzymol., 183, 63 (1990)].

Examples of the method for confirming that a protein has activity of catalyzing the reaction between the allylic diphosphate derivative and isopentenyl diphosphate include a method involving preparing a transformant expressing the protein by a method conventionally known in the art, producing the protein using the transformant, and then quantitatively or qualitatively analyzing the substrate or product by HPLC (high-performance liquid chromatography), TLC (thin-layer chromatography), or the like to confirm whether or not the protein can catalyze the reaction between the allylic diphosphate derivative and isopentenyl diphosphate.

(DNA Encoding Enzyme Having Prenyltransferase Activity)

Examples of DNA encoding the enzyme having prenyltransferase activity include the following DNAs [1] to [3]:

[1] DNA encoding any of the proteins [1] to [3];
[2] DNA having a base sequence represented by any of SEQ ID NOs: 1, 3, 5, 7, 9, 11, 13, 15, 17, 19, and 21; and
[3] DNA hybridizing under stringent conditions to DNA having a base sequence complementary to the base sequence represented by any of SEQ ID NOs: 1, 3, 5, 7, 9, 11, 13, 15, 17, 19, and 21; and encoding a protein having activity of catalyzing a reaction between the allylic diphosphate derivative and isopentenyl diphosphate.

In this context, the term "hybridizing" means a step in which the DNA hybridizes to DNA having a specific base sequence or a portion of the DNA. Thus, the base sequence of the DNA having a specific base sequence or the portion of the DNA may be DNA of length that is useful as a probe in Northern or Southern blot analysis or can be used as an oligonucleotide primer in PCR (polymerase chain reaction) analysis. Examples of the DNA used as a probe include DNA of at least 100 bases or longer, preferably of 200 bases or longer, and more preferably of 500 bases or longer. DNA of at least 10 bases or longer, preferably of 15 bases or longer, may be used.

Methods for DNA hybridization experiment are well known. Hybridization conditions can be determined according to the description of, for example, Molecular Cloning, 2nd ed. and 3rd ed. (2001), Methods for General and Molecular Bacteriology, ASM Press (1994), or Immunology methods manual, Academic press (Molecular) as well as many other standard textbooks to conduct the experiment.

Examples of the stringent conditions include conditions involving, for example, incubating a DNA-immobilized filter and probe DNA overnight at 42° C. in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 μg/l denatured salmon sperm DNA, and then washing the filter in, for example, a 0.2×SSC solution at approximately 65° C. Lower stringent conditions may be used. The stringent conditions can be changed by adjustment of the concentration of formamide (lower concentration of formamide gives lower stringent conditions) and change in salt concentration and temperature conditions. Examples of low stringent conditions include conditions involving, for example, overnight incubation at 37° C. in a solution containing 6×SSCE (20×SSCE corresponds to 3 mol/l sodium chloride, 0.2 mol/l sodium dihydrogen phosphate, and 0.02 mol/l EDTA, pH 7.4), 0.5% SDS, 30% formamide, and 100 μg/l denatured salmon sperm DNA, followed by washing using a solution of 1×SSC and 0.1% SDS at 50° C. Also, examples of lower stringent conditions include conditions involving hybridization using a solution with a higher salt concentration (e.g., 5×SSC) under the low stringent conditions, followed by washing.

These various conditions may be set by the addition or change of a blocking reagent used for suppressing background in the hybridization experiment. The addition of the blocking reagent may be accompanied by change of the hybridization conditions in order to adapt the conditions to each experiment.

Examples of DNA capable of hybridization under the stringent conditions described above include DNA having a base sequence having at least 80% or higher, preferably 90% or higher, more preferably 95% or higher, even more preferably 98% or higher, particularly preferably 99% or higher sequence identity to the base sequence represented by any of SEQ ID NOs: 1, 3, 5, 7, 9, 11, 13, 15, 17, 19, and 21 when calculated on the basis of the parameters using a program such as BLAST and FASTA.

Examples of the method for confirming that the DNA hybridizing under stringent conditions to the DNA encodes a protein having activity of catalyzing the reaction between the allylic diphosphate derivative and isopentenyl diphosphate include a method involving preparing recombinant DNA containing the DNA by a method conventionally known in the art, introducing the recombinant DNA into host cells, culturing the obtained biological cells, purifying the protein from the obtained culture, and then quantitatively or qualitatively analyzing the substrate or product by HPLC, TLC, or the like to confirm whether or not the protein can catalyze the reaction between the allylic diphosphate derivative and isopentenyl diphosphate.

Each variant enzyme and DNA encoding the variant enzyme can be obtained by the site-directed mutagenesis of, for example, the base sequence represented by SEQ ID NO: 1 (base sequence of *Micrococcus luteus* B-P 26-derived undecaprenyl diphosphate synthase) using a site-directed mutagenesis method described in Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), etc.

(Transformant)

Next, the method for preparing biological cells (transformant) transformed so as to express the enzyme having prenyltransferase activity will be described briefly. Here, mainly, a method for preparing a transformant that has been transformed so as to express the variant enzyme will be described briefly. Such a transformant can be prepared by a method conventionally known in the art as long as the design philosophy is determined.

For the mutagenesis, first, primers are designed so that they allow mutagenesis at a site of interest. Examples of the base sequences of the primers include base sequences described in Examples (see SEQ ID NOs: 23 to 42 in the Sequence Listing). Next, for example, mutagenized linear DNA is amplified by the PCR method or the like using DNA containing the base sequence represented by SEQ ID NO: 1 (base sequence of *Micrococcus luteus* B-P 26-derived undecaprenyl diphosphate synthase) as template DNA with the primers described above. Then, the obtained linear DNA is inserted downstream of a promoter in an appropriate expression vector using appropriate restriction enzymes or the like to prepare recombinant DNA. Then, the recombinant DNA is introduced into host cells compatible with the expression vector, whereby a transformant can be obtained.

Alternatively, for example, DNA containing the base sequence represented by SEQ ID NO: 1 (base sequence of *Micrococcus luteus* B-P 26-derived undecaprenyl diphosphate synthase) is inserted downstream of a promoter in an appropriate expression vector using appropriate restriction enzymes or the like. Mutagenized DNA, which is obtained by the PCR method or the like using the expression vector as template DNA with the primers described above, is rendered cyclic by polymerase to prepare recombinant DNA. Then, the recombinant DNA is introduced into host cells compatible with the expression vector, whereby a transformant can be obtained.

When such mutagenesis is unnecessary, for example, DNA containing the base sequence represented by SEQ ID NO: 1 (base sequence of *Micrococcus luteus* B-P 26-derived undecaprenyl diphosphate synthase) is inserted downstream of a promoter in an appropriate expression vector using appropriate restriction enzymes or the like to prepare recombinant DNA. Then, the recombinant DNA is introduced into host cells compatible with the expression vector, whereby a transformant can be obtained.

Although the description above is about the case using the DNA containing the known base sequence represented by SEQ ID NO: 1 (base sequence of *Micrococcus luteus* B-P 26-derived undecaprenyl diphosphate synthase), DNA encoding any of other prenyltransferase activity-having enzymes derived from the organism or prenyltransferase activity-having enzymes derived from organisms other than the organism may be used. In this case, screening can be performed by a known approach using, for example, a portion of the base sequence represented by SEQ ID NO: 1 as a probe to identify DNA encoding the enzyme having prenyltransferase activity, followed by isolation. The method for isolating the DNA molecule of interest using the DNA molecule as a probe is described in, for example, Molecular Cloning, 2nd edition, Cold Spring Harbor Press (1989).

Alternatively, the following method may be used: the organism-derived enzyme having prenyltransferase activity is purified by the purification operation as described above, and the amino acid sequence of the purified enzyme is determined to identify DNA encoding the enzyme, followed by isolation.

Any of microorganisms, yeasts, animal cells, insect cells, plant cells, and the like can be used as host cells as long as they are capable of expressing the gene of interest.

Examples of usable expression vectors include those which are capable of autonomously replicating in the host cells or being incorporated into the chromosome and contain a promoter at a position that allows transcription of the recombinant DNA.

When a prokaryotic organism such as bacteria is used as host cells, it is preferable that the recombinant DNA should be recombinant DNA that is capable of autonomously replicating in the prokaryotic organism and is also composed of a promoter, a ribosomal binding sequence, DNA encoding the enzyme having prenyltransferase activity, and a transcription termination sequence. The recombinant DNA may further contain a gene controlling the promoter.

Examples of the expression vector include pCold I (manufactured by Takara Bio Inc.), pCDF-1b and pRSF-1b (all manufactured by Novagen), pMAL-c2x (manufactured by New England Biolabs Inc.), pGEX-4T-1 (manufactured by GE Healthcare Biosciences Inc.), pTrcHis (manufactured by Invitrogen Corp.), pSE280 (manufactured by Invitrogen Corp.), pGEMEX-1 (manufactured by Promega Corp.), pQE-30 (manufactured by Qiagen), pET-3 to pET-52 (manufactured by Novagen), pKYP10 (JP 58-110600 A), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK(+) and pBluescript II KS(−) (manufactured by Stratagene Corp.), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (manufactured by Takara Bio Inc.), pUC118 (manufactured by Takara Bio Inc.), and pPA1 (JP 63-233798 A).

Any promoter that functions in host cells such as *Escherichia coli* can be used. Examples thereof include: promoters derived from *E. coli*, phages, etc., such as trp promoter ($P_{trp}$), T7 promoter, lac promoter ($P_{lac}$), $P_L$ promoter, $P_R$ promoter, and $P_{SE}$ promoter; and SPO1 promoter, SPO2 promoter, and penP promoter. Also, for example, artificially designed or modified promoters such as a promoter having two $P_{trp}$ sequences arranged in series, tac promoter, lacT7 promoter, and let I promoter, may be used.

Furthermore, xylA promoter for expression in microorganisms belonging to the genus *Bacillus* [Appl. Microbiol. Biotechnol., 35, 594-599 (1991)], P54-6 promoter for expression in microorganisms belonging to the genus *Corynebacterium* [Appl. Microbiol. Biotechnol., 53, 674-679 (2000)], and the like may be used.

It is preferable to use a plasmid having an appropriately adjusted distance (e.g., 6 to 18 bases) between a Shine-Dalgarno sequence (ribosomal binding sequence) and an initiation codon.

Examples of the prokaryotic organism include microorganisms belonging to the genera *Escherichia*, *Serratia*, *Bacillus*, *Brevibacterium*, *Corynebacterium*, *Microbacterium*, *Pseudomonas*, *Agrobacterium*, *Alicyclobacillus*, *Anabaena*, *Anacystis*, *Arthrobacter*, *Azotobacter*, *Chromatium*, *Erwinia*, *Methylobacterium*, *Phormidium*, *Rhodobacter*, *Rhodopseudomonas*, *Rhodospirillum*, *Scenedesmus*, *Streptomyces*, *Synechoccus*, and *Zymomonas*, for example, *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* BL21, *Bacillus subtilis* ATCC33712, *Bacillus megaterium*, *Brevibacterium ammoniagenes*, *Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Microbacterium ammoniaphilum* ATCC15354, *Serratia ficaria*, *Serratia fonticola*, *Serratia liquefaciens*, *Serratia marcescens*, *Pseudomonas* sp. D-0110, *Agrobacterium radiobacter*, *Agrobacterium rhizogenes*, *Agrobacterium rubi*, *Anabaena cylindrica*, *Anabaena doliolum*, *Anabaena flos-aquae*, *Arthrobacter aurescens*, *Arthrobacter citreus*, *Arthrobacter globiformis*, *Arthrobacter hydrocarboglutamicus*, *Arthrobacter mysorens*, *Arthrobacter nicotianae*, *Arthrobacter paraffineus*, *Arthrobacter protophormiae*, *Arthrobacter roseoparaffinus*, *Arthrobacter sulfureus*, *Arthrobacter ureafaciens*, *Chromatium buderi*, *Chromatium tepidum*, *Chromatium vinosum*, *Chromatium warmingii*, *Chromatium fluviatile*, *Erwinia uredovora*, *Erwinia carotovora*, *Erwinia ananas*, *Erwinia herbicola*, *Erwinia punctata*, *Erwinia terreus*, *Methylobacterium rhodesianum*, *Methylobacterium extorquens*, *Phormidium* sp. ATCC29409, *Rhodobacter capsulatus*, *Rhodobacter sphaeroides*, *Rhodopseudomonas blastica*, *Rhodopseudomonas marina*, *Rhodopseudomonas palustris*, *Rhodospirillum rubrum*, *Rhodospirillum salexigens*, *Rhodospirillum salinarum*, *Streptomyces ambofaciens*, *Streptomyces aureofaciens*, *Streptomyces aureus*, *Streptomyces fungicidicus*, *Streptomyces griseochromogenes*, *Streptomyces griseus*, *Streptomyces lividans*, *Streptomyces olivogriseus*, *Streptomyces rameus*, *Streptomyces tanashiensis*, *Streptomyces vinaceus*, and *Zymomonas mobilis*.

The recombinant DNA can be introduced by any method for introducing DNA into such host cells. Examples thereof include a method using calcium ions [Proc. Natl. Acad. Sci., USA, 69, 2110 (1972)], a protoplast method (JP 63-248394 A), an electroporation method [Nucleic Acids Res., 16, 6127 (1988)], and a heat shock method.

When a yeast strain is used as host cells, YEp13 (ATCC37115), YEp24 (ATCC37051), YCp50 (ATCC37419), pHS19, or pHS15, for example, can be used as an expression vector.

In this case, any promoter that functions in the yeast strain can be used. Examples thereof include promoters such as PHO5 promoter, PGK promoter, GAP promoter, ADH promoter, gal 1 promoter, gal 10 promoter, heat-shock polypeptide promoter, MFα1 promoter, and CUP 1 promoter.

Examples of the host cells include yeast strains belonging to the genera *Saccharomyces, Schizosaccharomyces, Kluyveromyces, Trichosporon, Schwanniomyces, Pichia, Candida* and the like and specifically include *Saccharomyces cerevisiae, Schizosaccharomyces pombe, Kluyveromyces lactis, Trichosporon pullulans, Schwanniomyces alluvius, Pichia pastoris*, and *Candida utilis*.

The recombinant DNA can be introduced by any method for introducing DNA into yeast. Examples thereof include an electroporation method [Methods Enzymol., 194, 182 (1990)], a spheroplast method [Proc. Natl. Acad. Sci., USA, 81, 4889 (1984)], and a lithium acetate method [J. Bacteriol., 153, 163 (1983)].

When animal cells are used as a host, pcDNAI, pcDM8 (commercially available from Funakoshi Corp.), pAGE107 (JP 3-22979 A), pAS3-3 (JP 2-227075 A), pCDM8 [Nature, 329, 840 (1987)], pcDNAI/Amp (manufactured by Invitrogen Corp.), pREP4 (manufactured by Invitrogen Corp.), pAGE103 [J. Biochem, 101, 1307 (1987)], pAGE210, pAMo, or pAMoA, for example, can be used as an expression vector.

In this case, any promoter that functions in the animal cells can be used. Examples thereof include cytomegalovirus (CMV) IE (immediate early) gene promoter, SV40 early promoter, metallothionein promoter, retrovirus promoter, heat-shock promoter, and SRα promoter. These promoters may be used in combination with human CMV IE gene enhancer.

Examples of the host cells include mouse myeloma cells, rat myeloma cells, mouse hybridoma cells, human Namalwa cells or Namalwa KJM-1 cells, human embryonic kidney cells, human leukemia cells, African green monkey kidney cells, Chinese hamster ovary (CHO) cells, and HBT5637 (JP 63-299 A).

Specific examples thereof include: mouse myeloma cells such as SP2/0 and NSO; rat myeloma cells such as YB2/0; human embryonic kidney cells such as HEK293 (ATCC CRL-1573); human leukemia cells such as BALL-1; and African green monkey kidney cells such as COS-1 and COS-7.

The recombinant DNA can be introduced by any method for introducing DNA into animal cells. Examples thereof include an electroporation method [Cytotechnology, 3, 133 (1990)], a calcium phosphate method (JP 2-227075 A), a lipofection method [Proc. Natl. Acad. Sci., USA, 84, 7413 (1987)], and a method described in Virology, 52, 456 (1973).

When insect cells are used as a host, the protein can be produced by a method described in, for example, Baculovirus Expression Vectors, A Laboratory Manual, W. H. Freeman and Company, New York (1992), Current Protocols in Molecular Biology, or Molecular Biology, A Laboratory Manual, Bio/Technology, 6, 47 (1988).

Specifically, insect cells are cotransfected with a vector for transferring the recombinant gene and baculovirus, so that recombinant virus is obtained in the culture supernatant of the insect cells. Then, insect cells are further infected with the recombinant virus, whereby the protein can be produced.

Examples of the gene transfer vector used in this method include pVL1392, pVL1393, and pBlueBac III (all manufactured by Invitrogen Corp.).

Examples of the baculovirus include *Autographa californica* nuclear polyhedrosis virus, which infects insects of the family Noctuidae.

Examples of the insect cells include *Spodoptera frugiperda* ovary cells, *Trichoplusia ni* ovary cells, and silkworm ovary-derived cultured cells.

Specific examples thereof include: *Spodoptera frugiperda* ovary cells such as Sf9 and Sf21 (Baculovirus Expression Vectors: A Laboratory Manual); *Trichoplusia ni* ovary cells such as High 5 and BTI-TN-5B1-4 (manufactured by Invitrogen Corp.); and silkworm ovary-derived cultured cells such as *Bombyx mori* N4.

Examples of the method for cotransfecting insect cells with the vector for transferring the recombinant gene and the baculovirus to prepare the recombinant virus include a calcium phosphate method (JP 2-227075 A) and a lipofection method [Proc. Natl. Acad. Sci., USA, 84, 7413 (1987)].

When plant cells are used as host cells, a Ti plasmid or tobacco mosaic virus vector, for example, can be used as an expression vector.

In this case, any promoter that functions in the plant cells can be used. Examples thereof include cauliflower mosaic virus (CaMV) 35S promoter and rice actin-1 promoter.

Examples of the host cells include cells of plants such as tobacco, potato, tomato, carrot, soybean, oilseed rape, alfalfa, rice, wheat, and barley.

The recombinant vector can be introduced by any method for introducing DNA into plant cells. Examples thereof include a method using *Agrobacterium* (JP 59-140885 A, JP 60-70080 A, and WO94/00977), an electroporation method (JP 60-251887 A), and a method using a particle gun (gene gun) (Japanese Patent Nos. 2606856 and 2517813).

The host may be any of microorganisms, yeasts, animal cells, insect cells, plant cells, and the like and may be preferably any of microorganisms, more preferably microorganisms belonging to the genus *Escherichia*, and even more preferably microorganisms belonging to *Escherichia coli*.

When expressed by yeasts, animal cells, insect cells, and plant cells, sugar- or sugar chain-added proteins can be obtained.

The obtained transformant is cultured in a medium and the enzyme having prenyltransferase activity is then generated and accumulated in the culture, whereby the enzyme having prenyltransferase activity can be produced. If necessary, the enzyme may be purified by the purification operation described above.

The transformant can be cultured in a medium according to a usual method used for culturing host cells. For example, the culture can be performed in the composition of the medium and the culture conditions described above.

(Polyisoprene)

Next, the polyisoprene of the present invention will be described. The polyisoprene of the present invention contains a trans structural moiety and a cis structural moiety as represented by the formula (4) shown below, wherein at least one atom or group contained in the trans structural moiety is replaced by another atom or group. In this context, the trans structural moiety means a moiety of repeated isoprene units with a trans structure (moiety C in the formula (4) shown below). Also, the cis structural moiety means a moiety of repeated isoprene units with a cis structure (moiety $(\ )_q$ (moiety D) in the formula (4) shown below).

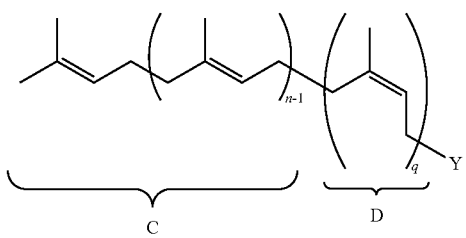

(4)

wherein n represents an integer of 1 to 10; q represents an integer of 30 to 40000; and Y represents a hydroxy group, a formyl group, a carboxy group, an ester group, a carbonyl group, or a group represented by the following formula (2).

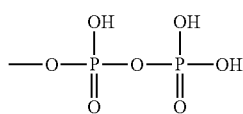

(2)

The polyisoprene of the present invention is structurally similar to natural rubber and is highly compatible with rubber molecules. Moreover, the polyisoprene of the present invention has been modified substantially only at a terminal site of the molecule. Specifically, the polyisoprene of the present invention contains a hydroxy group, a formyl group, a carboxy group, an ester group, a carbonyl group, or a group represented by the formula (2), positioned at the end of the cis structural moiety, and at least one atom or group contained in the trans structural moiety is replaced by another atom or group. Thus, the polyisoprene of the present invention strongly interacts with filler such as silica while the original properties of polyisoprene are not impaired. Since the polyisoprene of the present invention is highly compatible with rubber and strongly interacts with filler such as silica as described above, a rubber composition containing this polyisoprene is obtained as a rubber composition in which rubber molecules are combined with filler in a level higher than ever. The resulting rubber composition can have, for example, improved low-heat-build-up properties, wet grip performance, and abrasion resistance.

The polyisoprene of the present invention contains a polar group or the like only at the terminal site of the cis structural moiety and a site close to the end of the trans structural moiety. The polyisoprene therefore offers high dispersibility of filler such as silica and has a large effect of improving, for example, low-heat-build-up properties, wet grip performance, and abrasion resistance while the original properties of polyisoprene are not impaired, compared with polyisoprenes containing a polar group or the like in the main chain moiety or only at the terminal site of the cis structural moiety.

In the formula (4), n is as defined for n in the formula (1).

In the formula (4), q represents an integer of 30 to 40000 (preferably 15000 to 30000, more preferably 15000 to 20000).

In the formula (4), Y is as defined for Y in the formula (1). Here, Y is preferably a hydroxy group or a carboxy group, because the resulting polyisoprene strongly interacts with filler such as silica.

Examples of the atom or group (atom or group before replacement) contained in the trans structural moiety include the same as those exemplified as the atom or group (atom or group before replacement) contained in the trans structural moiety in the formula (1).

Examples of the another atom or group include the same as those exemplified as the another atom or the another group described about the formula (1).

As described above, at least one atom or group contained in the trans structural moiety is replaced by another atom or group. For the replacement, it is preferable, as described for the isoprene oligomer, that at least one atom or group contained in moiety VI in the following formula (4-1) should be replaced while no atom or group contained in moiety VII in the formula (4-1) should be replaced:

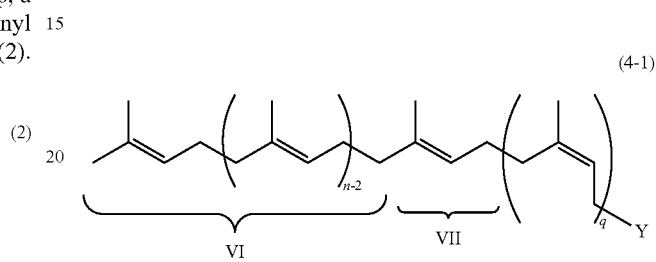

(4-1)

wherein n, q, and Y are as defined for n, q, and Y in the formula (4).

Specific examples of the trans structural moiety in the formula (4) include structures represented by the formulas (a) to (s) mentioned above. Among them, structures represented by the formulas (c), (d), (e), (f), (k), (l), and (r) are preferred because the resulting polyisoprene more strongly interacts with filler such as silica and has a large effect of improving low-heat-build-up properties, wet grip performance, and abrasion resistance.

(Process for Producing Polyisoprene)

Examples of the process for producing the polyisoprene of the present invention include a process including performing biosynthesis from the isoprene oligomer of the present invention and isopentenyl diphosphate.

The polyisoprene of the present invention is obtained by biosynthesis except for the organic synthesis of the allylic diphosphate derivative as an initiating substrate, and can thus take into account the exhaustion of petroleum resources or environmental issues.

It has heretofore been known that natural rubber latex contains an enzyme, a rubber elongation factor, and the like having activity of catalyzing the condensation reaction between an isoprene oligomer and isopentenyl diphosphate and catalyzing a reaction as shown below through which isopentenyl diphosphate is sequentially linked in a Z form (newly added isoprene unit has a cis structure) starting from the isoprene oligomer to produce a polyisoprene.

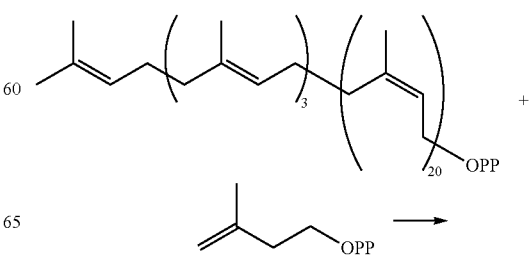

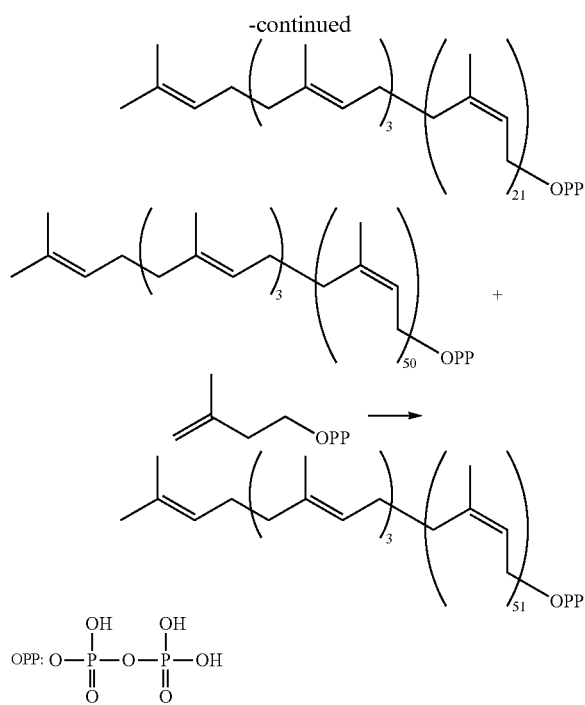

In the present invention, the polyisoprene can be produced using this enzyme, rubber elongation factor, or the like.

Specifically, examples of the method for biosynthesizing the polyisoprene of the present invention from the isoprene oligomer of the present invention and isopentenyl diphosphate include a method using the enzyme, the rubber elongation factor, or the like contained in natural rubber latex. Alternatively, the enzyme, the rubber elongation factor, or the like cloned from natural rubber latex may be used.

Specifically, the isoprene oligomer of the present invention and isopentenyl diphosphate can be allowed to react with each other in the presence of the enzyme and/or the rubber elongation factor. More specifically, for example, natural rubber latex or the enzyme, the rubber elongation factor, or the like separated from the natural rubber latex can be added into a solution containing the isoprene oligomer of the present invention and isopentenyl diphosphate to perform the reaction. The reaction temperature can be set to, for example, 20 to 40° C.; the reaction time can be set to, for example, 1 to 72 hours; and the pH can be set to, for example, 6 to 8. If necessary, magnesium chloride, a surfactant, 2-mercaptoethanol, and the like may further be added thereto.

The polyisoprene of the present invention obtained by the reaction is usually represented by the formula (4) wherein Y is a group represented by the formula (2) or a hydroxy group. This hydroxy group is formed through the hydrolysis of the group represented by the formula (2).

Further, the polyisoprene represented by the formula (4) wherein Y is a formyl group can be obtained, for example, by the oxidation of the polyisoprene of the formula (4) wherein Y is a group represented by the formula (2).

Further, the polyisoprene represented by the formula (4) wherein Y is a carboxy group can be obtained, for example, by the oxidation of the polyisoprene of the formula (4) wherein Y is a group represented by the formula (2).

Further, the polyisoprene represented by the formula (4) wherein Y is an ester group can be obtained, for example, by the oxidation and esterification of the polyisoprene of the formula (4) wherein Y is a group represented by the formula (2).

Further, the polyisoprene represented by the formula (4) wherein Y is a carbonyl group can be obtained, for example, by the oxidation and esterification of the polyisoprene of the formula (4) wherein Y is a group represented by the formula (2).

The natural rubber latex is not particularly limited in its origin. Examples thereof include *Hevea brasiliensis*, *Ficus elastica*, *Ficus lyrata*, *Ficus benjamina*, *Ficus religiosa*, *Ficus benghalensis*, and *Lactarius chrysorrheus*. Among them, *Hevea brasiliensis* is preferred because it produces rubber having a large molecular weight and its latex contains a large quantity of rubber.

The trunk of, for example, *Hevea brasiliensis* is cut in grooves (tapped) using a knife or the like, and natural rubber latex flowing out from the cleaved latex vessels is collected, whereby natural rubber latex can be obtained.

Examples of the enzyme and the rubber elongation factor separated from the natural rubber latex include a serum, a bottom fraction, and a rubber fraction separated by centrifugation of natural rubber latex. The serum, the bottom fraction, and the rubber fraction contain the enzyme, the rubber elongation factor, or the like.

(Rubber Composition)

The rubber composition of the present invention includes the isoprene oligomer of the present invention and/or the polyisoprene of the present invention. Accordingly, the rubber composition of the present invention is excellent in low-heat-build-up properties, wet grip performance, and abrasion resistance. In this context, the polyisoprene of the present invention can be used as a rubber component.

The content of the polyisoprene of the present invention is preferably 20% by mass or higher, more preferably 40% by mass or higher, and even more preferably 60% by mass or higher, with respect to 100% by mass of rubber components, and may be 100% by mass.

Examples of rubber components that can be used in addition to the polyisoprene of the present invention include diene rubbers such as isoprene rubber (IR), natural rubber (NR), butadiene rubber (BR), styrene-butadiene rubber (SBR), styrene-isoprene-butadiene rubber (SIBR), chloroprene rubber (CR), and acrylonitrile-butadiene rubber (NBR). These rubber components may be used alone or in combination of two or more thereof. Among them, NR and BR are preferred.

For allowing a rubber composition to contain the isoprene oligomer of the present invention, it is preferable to use NR as a rubber component because it is highly compatible with isoprene oligomers. The combined use of the isoprene oligomer of the present invention and NR is more favorable for the effects of the addition of the isoprene oligomer of the present invention.

When the rubber composition contains the isoprene oligomer of the present invention, the content of NR is preferably 20% by mass or higher, more preferably 40% by mass or higher, and even more preferably 60% by mass or higher, with respect to 100% by mass of rubber components, and may be 100% by mass.

The content of the isoprene oligomer of the present invention is preferably 1 part by mass or higher, and more preferably 2 parts by mass or higher, with respect to 100 parts by mass of rubber components. If the content is less than 1 part by mass, the effects of the addition of the isoprene oligomer of the present invention might be achieved insufficiently. Also, the content of the isoprene oligomer is preferably 20 parts by mass or lower, and more preferably 15 parts by mass or lower. If the content exceeds 20 parts by mass, the strength and, by extension, abrasion resistance of the resulting rubber composition may be reduced.

Examples of filler that can be used in the present invention include silica, carbon black, clay, and calcium carbonate.

In the present invention, it is preferable to use silica as filler. The rubber composition further containing silica ensures sufficient achievement of the effects of the addition of the isoprene oligomer of the present invention and/or the polyisoprene of the present invention. Examples of the silica include, but not particularly limited to, dry silica (silicic anhydride) and wet silica (hydrous silicic acid). Wet silica is preferred because of being rich in silanol groups.

For the present invention, it is also preferable to use carbon black as filler. In this case as well, the effects of the addition of the isoprene oligomer of the present invention and/or the polyisoprene of the present invention can be achieved sufficiently.

The rubber composition of the present invention may appropriately contain, in addition to the components described above, compounding ingredients generally used in the production of rubber compositions, for example, a silane coupling agent, zinc oxide, stearic acid, various antioxidants, a softener (e.g., oil), wax, a vulcanizing agent (e.g., sulfur), and a vulcanization accelerator.

The rubber composition of the present invention can be produced using a process known in the art and can be produced, for example, by a process involving kneading the components using a rubber kneading apparatus such as an open roll mill or a Banbury mixer, followed by vulcanization.

The rubber composition of the present invention can be used suitably in various tire components (e.g., treads, sidewalls, undertread, plies, breakers, and carcass) and the like.

(Pneumatic Tire)

The pneumatic tire of the present invention can be produced by a usual process using the rubber composition. Specifically, the unvulcanized rubber composition is extruded and processed into a shape appropriate for a tire component (e.g., treads and sidewalls), arranged by a usual method in a tire building machine, and assembled with other tire components to form an unvulcanized tire. This unvulcanized tire is heated and pressurized in a vulcanizer, whereby a tire can be produced.

EXAMPLES

The present invention will be described more specifically with reference to Examples. However, the present invention is not intended to be limited to these Examples.

Preparation of Initiating Substrate

Production Example 1

Synthesis of 10-acetyl-3,7-dimethyl-dodeca-(2E, 6E)-dienyl diphosphate (compound represented by the formula (S))

Synthesis was carried out with farnesol as a starting material. The hydroxy group of farnesol was protected using imidazole and tert-butylphenylchlorosilane (TBDPS) in anhydrous dichloromethane to obtain a TBDPS-protected form (compound represented by (ai) below) (yield: 92%).

The olefin at position 10 was oxidized using m-chloroperbenzoic acid in anhydrous dichloromethane to obtain an epoxy form (compound represented by (aii) below) (yield: 9%). Next, the epoxy was oxidized with orthoperiodic acid in anhydrous tetrahydrofuran to obtain an aldehyde form (compound represented by (aiii) below) (yield: 28%). Next, a Grignard reagent was prepared from magnesium and butane bromide in anhydrous methanol, and the aldehyde form was added to the Grignard reagent to obtain a secondary alcohol form (compound represented by (aiv) below) (yield: 68%). The secondary hydroxy group was protected by acetylation with acetic anhydride in the presence of dimethylaminopyridine in an anhydrous dichloromethane solvent to obtain an ester form (compound represented by (av) below) (yield: 81%). The TBDPS protective group was deprotected using tetra-n-butylammonium hydrate in anhydrous tetrahydrofuran to obtain a primary alcohol form (compound represented by (avi) below) (yield: 82%). Next, the primary hydroxy group was replaced by chlorine using N-chlorosuccinimide and dimethyl sulfide in an anhydrous dichloromethane solvent at −40° C. or lower to obtain a chloride (compound represented by (avii) below) (yield: 82%). Next, the chloride was diphosphorylated using tris-tetra-n-butylammonium hydrogen pyrophosphate in anhydrous acetonitrile to obtain a compound represented by (aviii) below (compound represented by the formula (S)) as the substance of interest (yield: 42%).

The intermediate in each synthesis step and the final product were confirmed by TLC and instrumental analysis (IR, NMR).

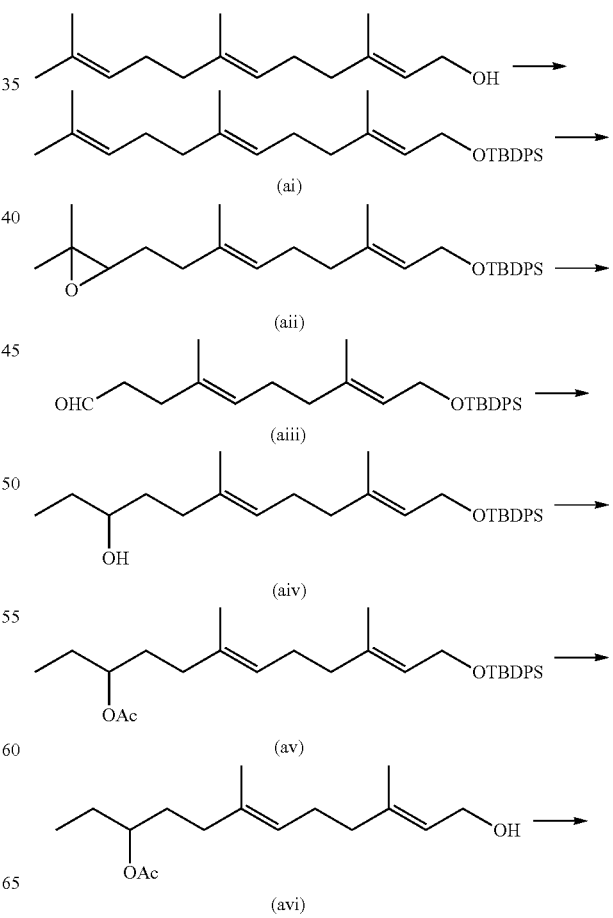

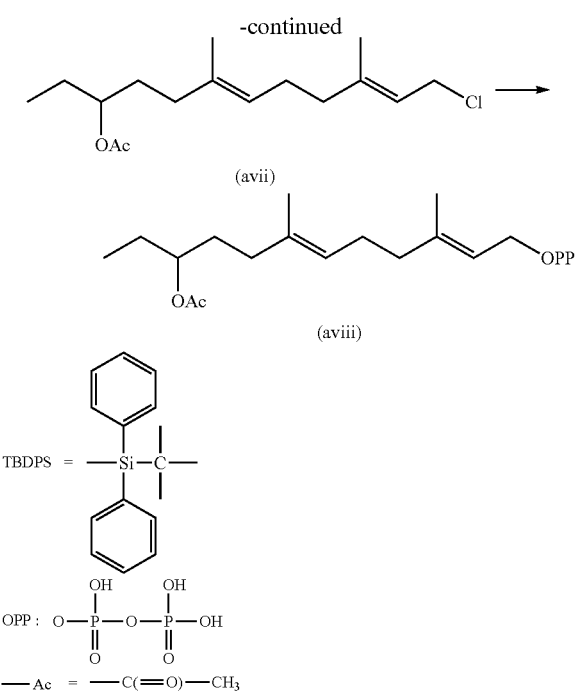

Production Example 2

Synthesis of 8-methoxy-3,7-dimethyl-dodeca-(2E, 6E)-dienyl diphosphate (compound represented by the formula (B))

Synthesis was carried out with geraniol as a starting material. Geraniol was acetylated using pyridine and acetic anhydride in anhydrous dichloromethane to obtain an acetate (compound represented by (bi) below) (yield: 95%). Next, the carbon atom at position 8 was subjected to selenium oxidation in ethanol to obtain an aldehyde form (compound represented by (bii) below) (yield: 24%). Next, the aldehyde was alkaline-hydrolyzed using potassium hydroxide to obtain an alcohol form (compound represented by (biii) below) (yield: 38%). Next, the alcohol was treated with imidazole and tert-butyldiphenylsilyl chloride (TB-DPS) in anhydrous dichloromethane to obtain a compound represented by (biv) below) (yield: 80%). Then, the compound was reacted with butyllithium in anhydrous ether to obtain a butyl alcohol form (compound represented by (bv) below) (yield: 73%). Next, the alcohol was converted to a sodium salt with sodium hydroxide in anhydrous tetrahydrofuran, and methyl iodide was then added thereto, followed by Williamson synthesis to obtain an ether form (compound represented by (bvi) below) (yield: 95%). Next, deprotection was carried out using tetra-n-butylammonium fluoride in anhydrous tetrahydrofuran to obtain an alcohol form (compound represented by (bvii) below) (yield: 87%). Next, the primary hydroxy group was replaced by chlorine using N-chlorosuccinimide and dimethyl sulfide in an anhydrous dichloromethane solvent at −40° C. or lower to obtain a chloride (compound represented by (bviii) below) (yield: 92%). Next, the chloride was diphosphorylated using tris-tetra-n-butylammonium hydrogen pyrophosphate in anhydrous acetonitrile to obtain a compound represented by (bix) below (compound represented by the formula (B)) as the substance of interest (yield: 26%).

The intermediate in each synthesis step and the final product were confirmed by TLC and instrumental analysis (IR, NMR).

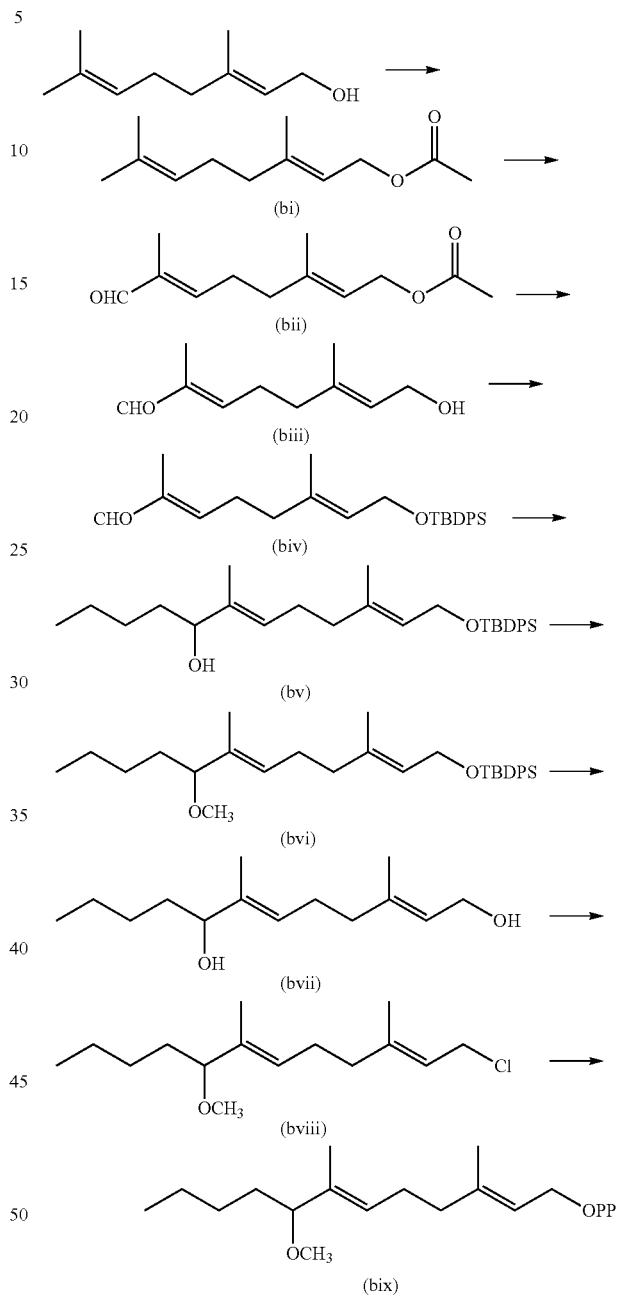

Production Example 3

Synthesis of 8-hydroxy-3,7-dimethyl-dodeca-(2E, 6E)-dienyl diphosphate (compound represented by the formula (C))

Synthesis was carried out with geraniol as a starting material. Geraniol was acetylated using pyridine and acetic anhydride in anhydrous dichloromethane to obtain an acetate (compound represented by (ci) below) (yield: 97%). Next, the carbon atom at position 8 was subjected to selenium oxidation in ethanol to obtain an aldehyde form (compound represented by (cii) below) (yield: 20%). Next, the aldehyde was alkaline-hydrolyzed using potassium hydroxide to obtain an alcohol form (compound represented by (ciii) below) (yield: 42%). Next, the alcohol was treated with imidazole and tert-butyldiphenylsilyl chloride (TBDPS) in anhydrous dichloromethane to obtain a compound represented by (civ) below (yield: 80%). Then, the compound was reacted with butyllithium in anhydrous ether to obtain a butyl alcohol form (yield: 62%). Next, deprotection was carried out using tetra-n-butylammonium fluoride in anhydrous tetrahydrofuran to obtain a diol form (compound represented by (cvi) below) (yield: 94%). Next, the primary hydroxy group was replaced by chlorine using N-chlorosuccinimide and dimethyl sulfide in an anhydrous dichloromethane solvent at −40° C. or lower to obtain a chloride (compound represented by (cvii) below) (yield: 90%). Next, the chloride was diphosphorylated using tris-tetra-n-butylammonium hydrogen pyrophosphate in anhydrous acetonitrile to obtain a compound represented by (cviii) below (compound represented by the formula (C)) as the substance of interest (yield: 46%).

The intermediate in each synthesis step and the final product were confirmed by TLC and instrumental analysis (IR, NMR).

Production Example 4

Synthesis of (10S)-hydroxy-3,7-dimethyl-dodeca-(2E,6E)-dienyl diphosphate (compound represented by the formula (D))

Synthesis was carried out with farnesol as a starting material. A protective group was bonded to the hydroxy group of farnesol using imidazole, anhydrous dimethylformamide, anhydrous dichloromethane, and tert-butyldiphenylsilyl chloride (TBDPS) to obtain a TBDPS-protected form (compound represented by (di) below) (yield: 99%). Next, this compound was reacted with m-chloroperbenzoic acid in an anhydrous dichloromethane solvent to obtain an epoxy form (compound represented by (dii) (below) (yield: 29%). Next, the epoxy was subjected to periodic acid oxidation using orthoperiodic acid in a mixed solvent of ether and tetrahydrofuran to obtain an aldehyde form (compound represented by (diii) below) (yield: 73%). A Grignard reagent was prepared from ethyl iodide and magnesium in an anhydrous ether solvent and then reacted with the aldehyde to form an alcohol form (compound represented by (div) below) (yield: 80%). The secondary hydroxy group of the racemic alcohol form and (S)-MaNP acid were subjected to reaction in the presence of N,N-dicyclohexylcarbodiimide, 4-dimethylaminopyridine, and (+)-10-camphorsulfonic acid in an anhydrous dichloromethane solvent to obtain diastereomers. Then, the diastereomers were optically resolved by HPLC, and the absolute configuration was determined by NMR to optically obtain a compound represented by (dv) below (yield: 80%). The TBDPS protective group was then deprotected using tetra-n-butylammonium hydrate in anhydrous tetrahydrofuran to obtain a diol form (compound represented by (dvi) below) (yield: 80%). Next, the primary hydroxy group was replaced by chlorine using N-chlorosuccinimide and dimethyl sulfide in an anhydrous dichloromethane solvent at −40° C. or lower to obtain a chloride (compound represented by (dvii) below) (yield: 80%). Next, the chloride was diphosphorylated using tris-tetra-n-butylammonium hydrogen pyrophosphate in anhydrous acetonitrile to obtain a compound represented by (dviii) below (compound represented by the formula (D)) as the substance of interest (yield: 46%).

The intermediate in each synthesis step and the final product were confirmed by TLC and instrumental analysis (IR, NMR).

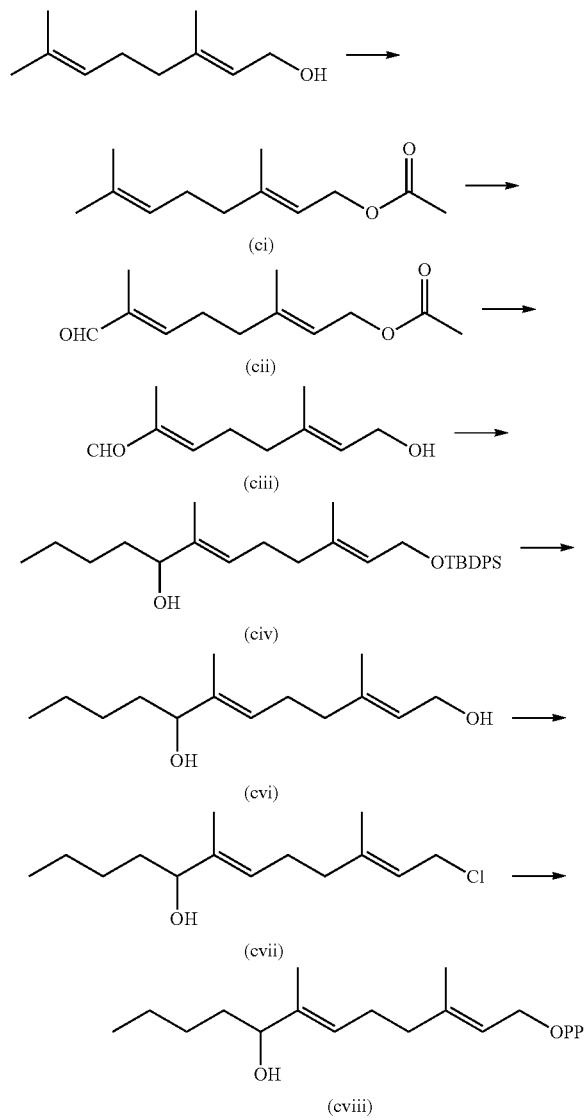

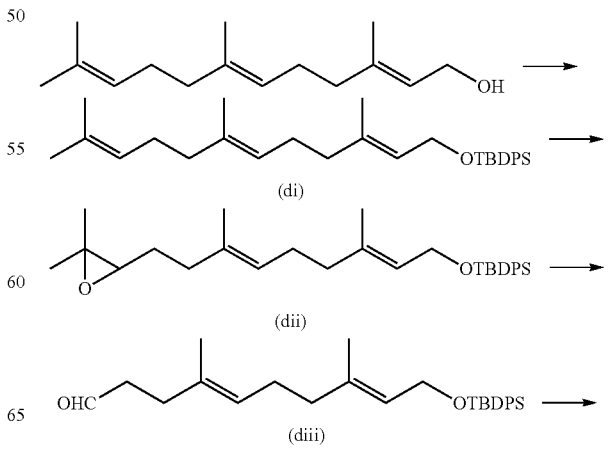

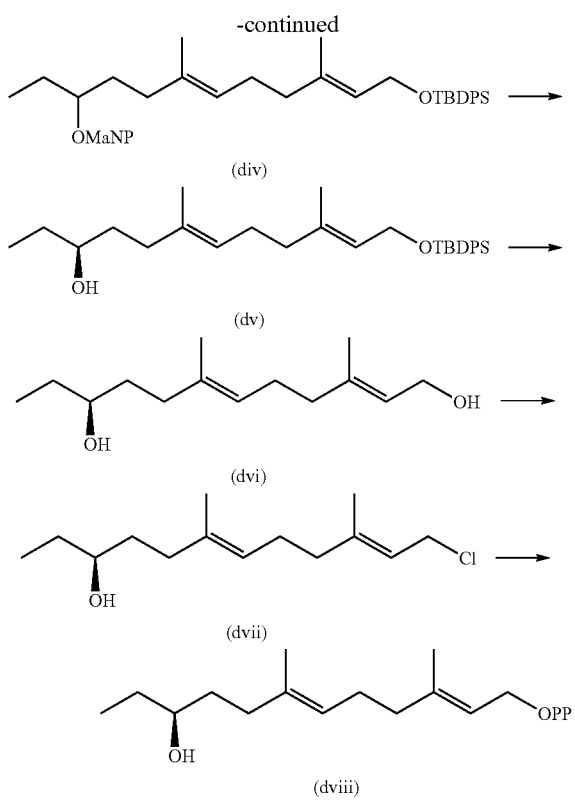

Production Example 5

Synthesis of (10R)-hydroxy-3,7-dimethyl-dodeca-(2E,6E)-dienyl diphosphate (compound represented by the formula (E))

Synthesis was carried out with farnesol as a starting material. A protective group was bonded to the hydroxy group of farnesol using imidazole, anhydrous dimethylformamide, anhydrous dichloromethane, and tert-butyldiphenylsilyl chloride (TBDPS) to obtain a TBDPS-protected form (compound represented by (ei) below) (yield: 99%). Next, this compound was reacted with m-chloroperbenzoic acid in an anhydrous dichloromethane solvent to obtain an epoxy form (compound represented by (eii) below) (yield: 29%). Next, the epoxy was subjected to periodic acid oxidation using orthoperiodic acid in a mixed solvent of ether and tetrahydrofuran to obtain an aldehyde form (compound represented by (eiii) below) (yield: 73%). A Grignard reagent was prepared from ethyl iodide and magnesium in an anhydrous ether solvent and then reacted with the aldehyde to form an alcohol form (compound represented by (eiv) below) (yield: 80%). The secondary hydroxy group of the racemic alcohol form and (S)-MaNP acid were subjected to reaction in the presence of N,N-dicyclohexylcarbodiimide, 4-dimethylaminopyridine, and (+)-10-camphorsulfonic acid in an anhydrous dichloromethane solvent to obtain diastereomers. Then, the diastereomers were optically resolved by HPLC, and the absolute configuration was determined by NMR to optically obtain a compound represented by (ev) below (yield: 84%). The TBDPS protective group was then deprotected using tetra-n-butylammonium hydrate in anhydrous tetrahydrofuran to obtain a diol form (compound represented by (evi) below) (yield: 91%). Next, the primary hydroxy group was replaced by chlorine using N-chlorosuccinimide and dimethyl sulfide in an anhydrous dichloromethane solvent at −40° C. or lower to obtain a chloride (compound represented by (evii) below) (yield: 70%). Next, the chloride was diphosphorylated using tris-tetra-n-butylammonium hydrogen pyrophosphate in anhydrous acetonitrile to obtain a compound represented by (eviii) below (compound represented by the formula (E)) as the substance of interest (yield: 59%).

The intermediate in each synthesis step and the final product were confirmed by TLC and instrumental analysis (IR, NMR).

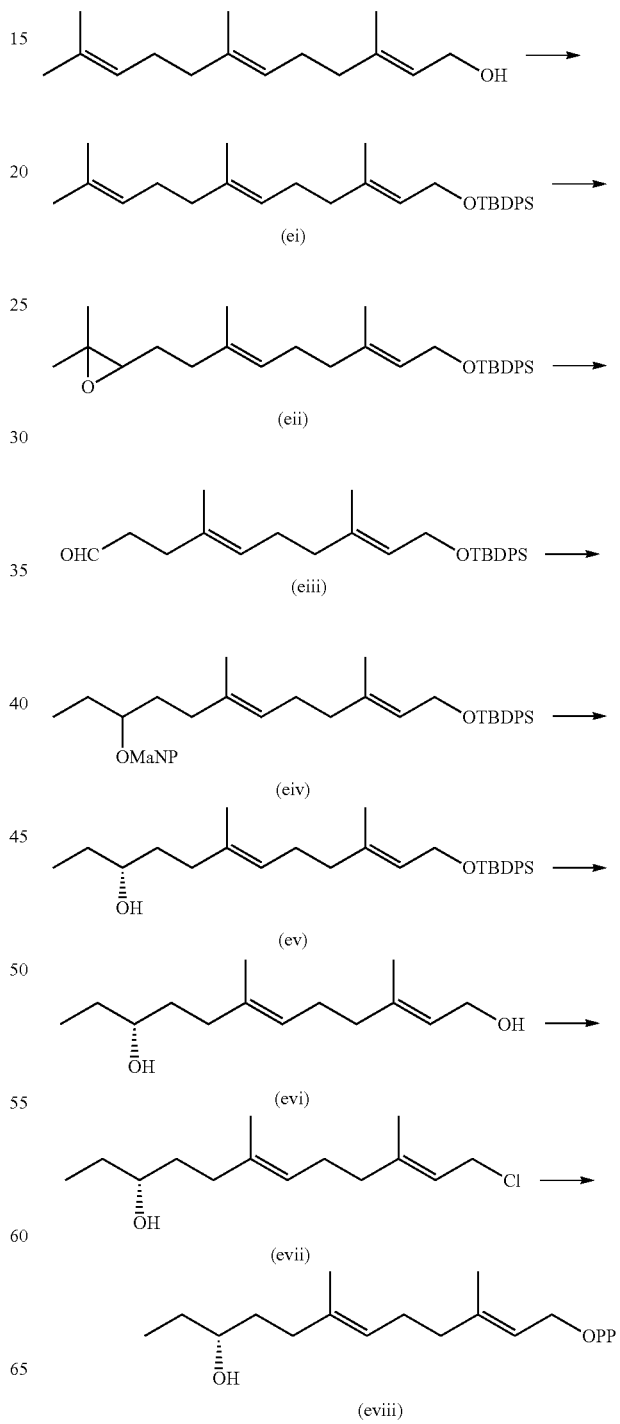

Production Example 6

Synthesis of 10-hydroxy-3,7-dimethyl-dodeca-(2E,6E)-dienyl diphosphate (compound represented by the formula (R))

Synthesis was carried out with farnesol as a starting material. A protective group was bonded to the hydroxy group of farnesol using imidazole, anhydrous dimethylformamide, anhydrous dichloromethane, and tert-butyldiphenylsilyl chloride (TBDPS) to obtain a TBDPS-protected form (fi) (yield: 99%). Next, this compound was reacted with m-chloroperbenzoic acid in an anhydrous dichloromethane solvent to obtain an epoxy form (fii) (yield: 29%). The epoxy was subjected to periodic acid oxidation using orthoperiodic acid in a mixed solvent of ether and tetrahydrofuran to obtain an aldehyde form (fiii) (yield: 73%). A Grignard reagent was prepared from ethyl iodide and magnesium in an anhydrous ether solvent and then reacted with the aldehyde to form an alcohol form (fiv) (yield: 80%). The TBDPS group in the compound (fiv) was removed using tetrabutylammonium fluoride in an anhydrous tetrahydrofuran solvent to form a diol form (fv) (yield: 93%).

The hydroxy group present at an allylic position in the diol form (fv) was chlorinated using N-chlorosuccinimide and dimethyl sulfide in an anhydrous dichloromethane solvent at −40° C. or lower to form a chloride (fvi) (yield: 69%). The chloride (fvi) was diphosphorylated using tris(tetra-N-butyl)ammonium hydrogen pyrophosphate in an anhydrous acetonitrile solvent and applied to an ion-exchange column to synthesize a compound (fvii) (compound represented by the formula (R)) as the substance of interest (yield: 28%).

The intermediate in each synthesis step and the final product were confirmed by TLC and instrumental analysis (IR, NMR).

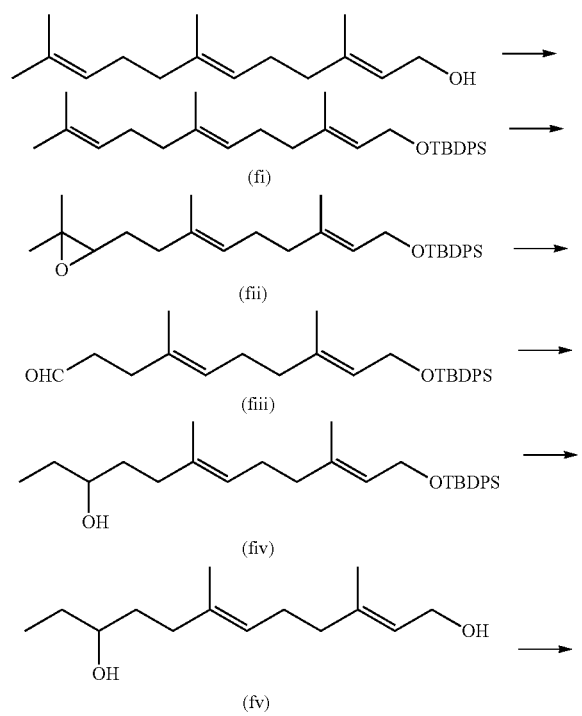

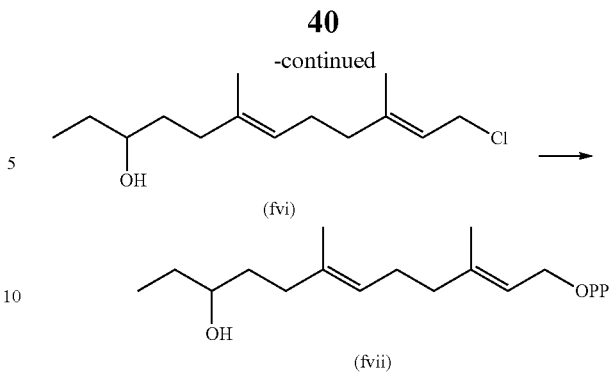

Production Example 7

Synthesis of 8-[(tert-butyldimethylsilyl)oxy]-3,7-dimethyl-octa-(2E,6E)-dienyl diphosphate (compound represented by the formula (P))

Synthesis was carried out with geraniol as a starting material. Geraniol was acetylated using pyridine and acetic anhydride in anhydrous dichloromethane to obtain an acetate (compound represented by (gi) below) (yield: 97%). Next, the carbon atom at position 8 was subjected to selenium oxidation in ethanol to obtain an alcohol form (compound represented by (gii) below) (yield: 20%). The alcohol was reacted with tert-butyldimethylsilyl chloride in the presence of a basic catalyst using imidazole to obtain a compound represented by (giii) below (yield: 87%). Next, the compound was hydrolyzed with potassium hydroxide to obtain an alcohol form (compound represented by (giv) below) (yield: 78%). The alcohol form was chlorinated by the N-chlorosuccinimide method to obtain a chloride (compound represented by (gv) below) (yield: 40%). Next, the chloride was mixed with n-butylammonium hydrogen diphosphate in anhydrous acetonitrile to obtain a compound represented by (gvi) below (compound represented by the formula (P)) as the substance of interest (yield: 26%).

The intermediate in each synthesis step and the final product were confirmed by TLC and instrumental analysis (IR, NMR).

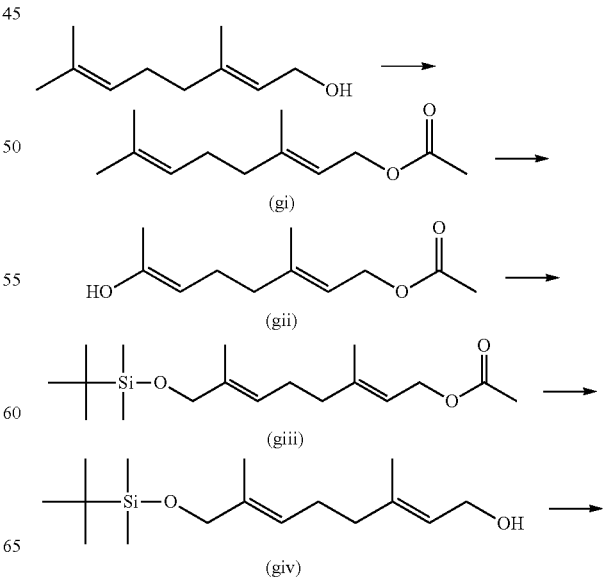

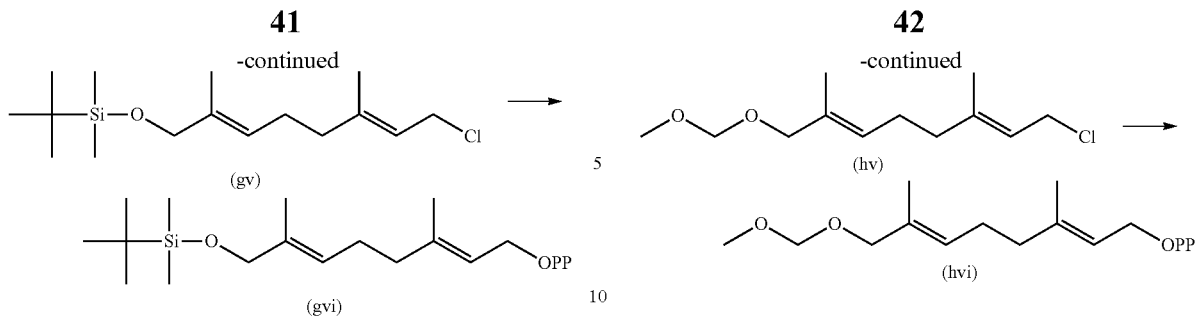

Production Example 8

Synthesis of 8-methoxymethoxy-3,7-dimethyl-octa-(2E,6E)-dienyl diphosphate (compound represented by the formula (H))

Synthesis was carried out with geraniol as a starting material. Geraniol was stirred together with acetic anhydride in pyridine to acetylate the hydroxy group, so that a compound represented by (hi) below was obtained (yield: 12%). Next, the compound was subjected to oxidation reaction with selenium dioxide and tert-butyl hydroperoxide to obtain a trans alcohol form (compound represented by (hii) below) (yield: 38%). The alcohol form was subjected to reaction using chloromethyl ethyl ether and diisopropylethylamine in dichloromethane to obtain a compound represented by (hiii) below in which a methoxymethyl ether group was introduced in the hydroxy group at position 8 (yield: 76%). Next, the acetyl group was converted to a hydroxy group using potassium hydroxide to obtain an alcohol form (compound represented by (hiv) below) (yield: 95%). The hydroxy group in the alcohol form was chlorinated using N-chlorosuccinimide to obtain a chloride (compound represented by (hv) below) (yield: 30%). Then, the chloride was diphosphorylated with tris(tetra-n-butyl)ammonium hydrogen diphosphate and applied to a cellulose column to obtain a compound represented by (hvi) below (compound represented by the formula (H)) as the substance of interest (yield: 77%).

The intermediate in each synthesis step and the final product were confirmed by TLC and instrumental analysis (IR, NMR).

Production Example 9

Synthesis of 8-n-propylthio-3,7-dimethyl-octa-(2E, 6E)-dienyl diphosphate (compound represented by the formula (M))

Synthesis was carried out with geraniol as a starting material. Geraniol and dihydropyran were condensed in the presence of a pyridinium p-toluenesulfonate catalyst to obtain a compound represented by (ii) below in which the hydroxy group in geraniol was protected with a tetrahydropyran ring (yield: 85%). Next, the compound was subjected to oxidation reaction with selenium dioxide and tert-butyl hydroperoxide to obtain a trans alcohol form (compound represented by (iii) below) (yield: 47%). The alcohol form was chlorinated using N-chlorosuccinimide in dichloromethane to obtain a compound represented by (iiii) below (yield: 92%). Next, n-propanethiol was added to a solution of metallic sodium dissolved in ethanol and the resulting solution was reacted with the compound to obtain a thioether (compound represented by (iiv) below) (yield: 28%). Next, p-toluenesulfonic acid was allowed to act thereon in methanol to obtain an alcohol form (compound represented by (iv) below) (yield: 75%). The alcohol form was chlorinated by the N-chlorosuccinimide method to obtain a chloride (compound represented by (ivi) below) (yield: 40%). Next, the chloride was mixed with n-butylammonium hydrogen diphosphate in anhydrous acetonitrile to obtain a compound represented by (ivii) below (compound represented by the formula (M)) as the substance of interest (yield: 32%).

The intermediate in each synthesis step and the final product were confirmed by TLC and instrumental analysis (IR, NMR).

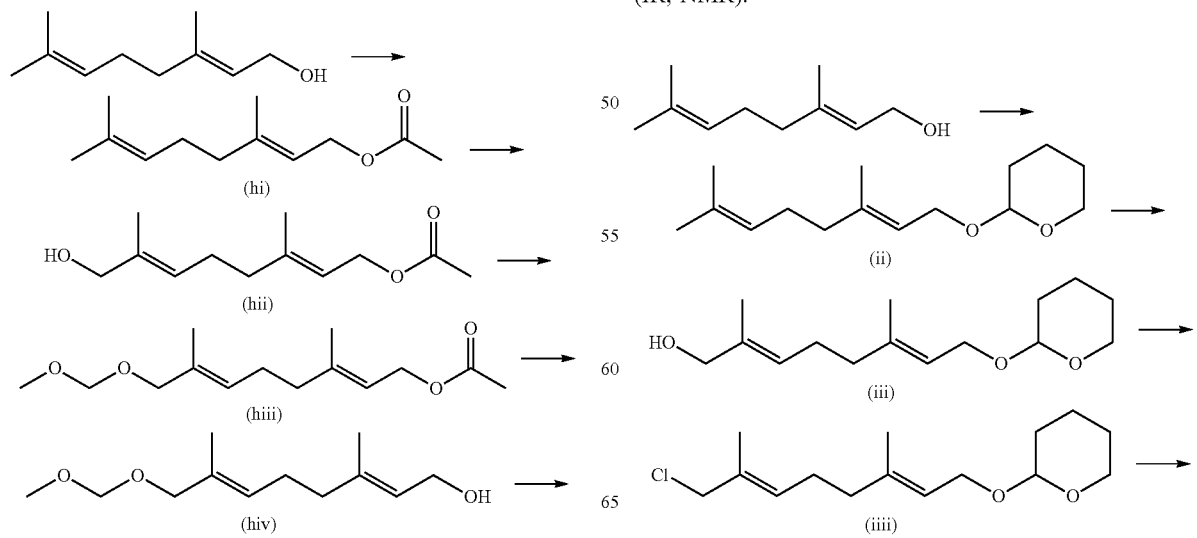

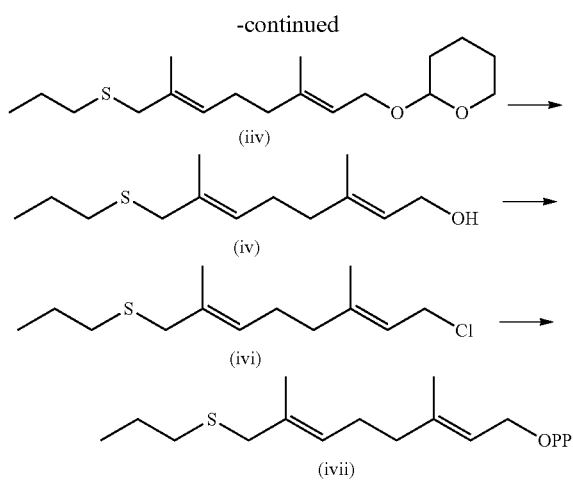
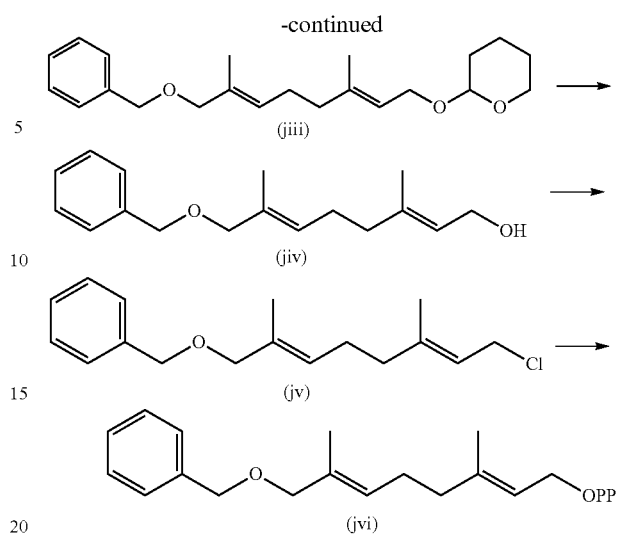

Production Example 10

Synthesis of 8-benzyloxy-3,7-dimethyl-octa-(2E, 6E)-dienyl diphosphate (compound represented by the formula (N))

Synthesis was carried out with geraniol as a starting material. Geraniol and dihydropyran were condensed in the presence of a pyridinium p-toluenesulfonate catalyst to obtain a compound represented by (ji) below in which the hydroxy group in geraniol was protected with a tetrahydropyran ring (yield: 85%). Next, the compound was subjected to oxidation reaction with selenium dioxide and tert-butyl hydroperoxide to obtain a trans alcohol form (compound represented by (jii) below) (yield: 47%). Next, thereto were added benzyl bromide and sodium hydroxide in anhydrous tetrahydrofuran to obtain an ether (compound represented by (jiii) below) (yield: 87%). Next, p-toluenesulfonic acid was allowed to act thereon in methanol to obtain an alcohol form (compound represented by (jiv) below) (yield: 69%). The alcohol form was chlorinated by the N-chlorosuccinimide method to obtain a chloride (compound represented by (jv) below) (yield: 40%). Next, the chloride was mixed with n-butylammonium hydrogen diphosphate in anhydrous acetonitrile to obtain a compound represented by (jvi) below (compound represented by the formula (N)) as the substance of interest (yield: 26%).

The intermediate in each synthesis step and the final product were confirmed by TLC and instrumental analysis (IR, NMR).

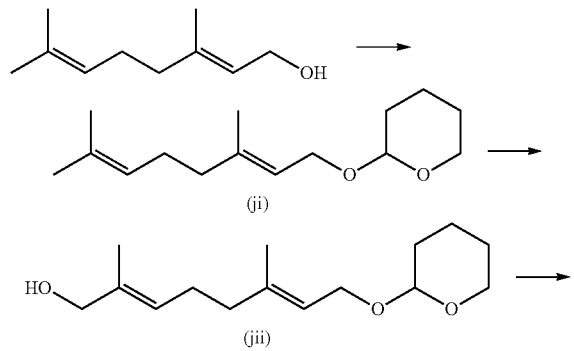

Production Example 11

Synthesis of 7-acetyl-7-aza-3-methyl-dodeca-(2E)-dienyl diphosphate (compound represented by the formula (K))

Synthesis was carried out with geraniol as a starting material. Geraniol was acetylated with acetic anhydride in the presence of dimethylaminopyridine in anhydrous dichloromethane to obtain an ester form (compound represented by (ki) below) (yield: 96%). The olefin at position 6 was oxidized using m-chloroperbenzoic acid in anhydrous dichloromethane to obtain an epoxy form (compound represented by (kii) below) (yield: 92%). Next, the epoxy was oxidized with orthoperiodic acid in anhydrous tetrahydrofuran to obtain an aldehyde form (compound represented by (kiii) below) (yield: 66%). Next, the aldehyde was reductively aminated using n-butylamine and sodium cyanoborohydride in anhydrous methanol to obtain a secondary amine (compound represented by (kiv) below) (yield: 66%). The amine was acetylated with acetic anhydride in the presence of dimethylaminopyridine in an anhydrous dichloromethane solvent to obtain a secondary amide (compound represented by (kv) below) (yield: 38%). The ester site was irreversibly hydrolyzed with potassium hydroxide in anhydrous methanol to obtain a primary alcohol form (compound represented by (kvi) below) (yield: 76%). Next, the primary hydroxy group was replaced by chlorine using N-chlorosuccinimide and dimethyl sulfide in an anhydrous dichloromethane solvent at −40° C. or lower to obtain a chloride (compound represented by (kvii) below) (yield: 67%). Next, the chloride was diphosphorylated using tris-tetra-n-butylammonium hydrogen pyrophosphate in anhydrous acetonitrile to obtain the substance of interest (compound represented by (kviii) below (compound represented by the formula (K))) (yield: 50%).

The intermediate in each synthesis step and the final product were confirmed by TLC and instrumental analysis (IR, NMR).

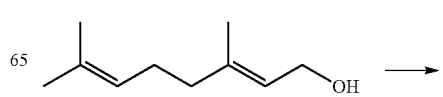

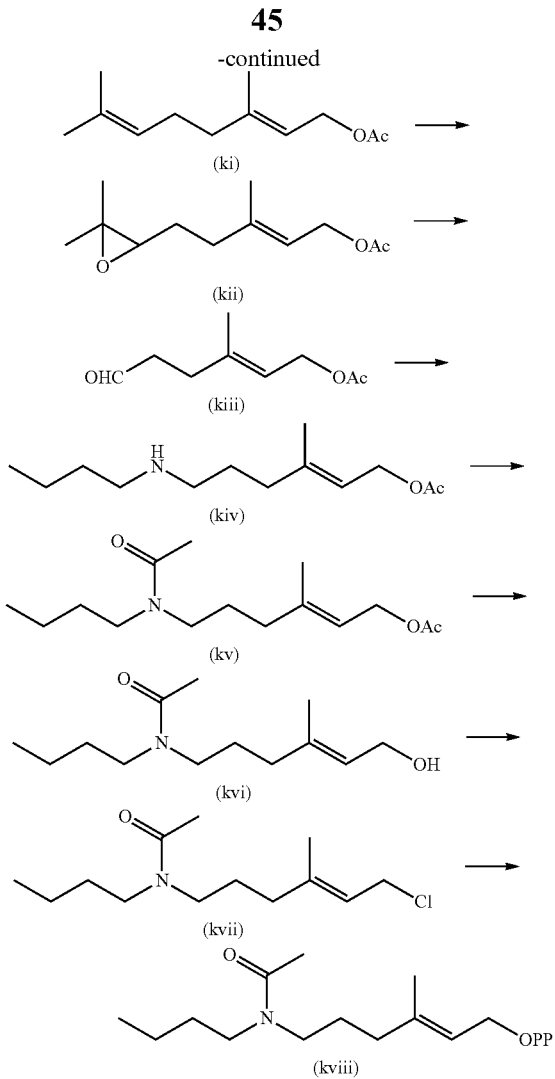

Production Example 12

Preparation of Mutagenized Enzyme

The reagent used was QuikChange Site-Directed Mutagenesis Kit from Stratagene Corp. Primers were designed so that they allowed mutagenesis at a site of interest. Primers for mutagenesis were purchased from Medical & Biological Laboratories, Co., Ltd. (manufacturer: XX IDT). The designed primers are as follows.

Primers for preparation of variant enzyme N31A:
Sense primer 5'-gac gga gca ggc cga tgg gca aaa-3' (SEQ ID NO: 23),
Antisense primer 5'-cat cgg cct gct ccg tcc ata atg a-3' (SEQ ID NO: 24);
Primers for preparation of variant enzyme N77A:
Sense primer 5'-act gaa gca tgg tct cgt cct aaa g-3' (SEQ ID NO: 25),
Antisense primer 5'-gag acc atg ctt cag ttg aaa atg c-3' (SEQ ID NO: 26);
Primers for preparation of variant enzyme L91N:
Sense primer 5'-gat gaa aaa ccc ggg tga ttt ttt aa-3' (SEQ ID NO: 27),
Antisense primer 5'-cac ccg ggt ttt tca tca agt aat ta-3' (SEQ ID NO: 28);
Primers for preparation of variant enzyme L91D:
Sense primer 5'-gat gaa aga tcc ggg tga ttt ttt aa-3' (SEQ ID NO: 29),
Antisense primer 5'-cac ccg gat ctt tca tca agt aat ta-3' (SEQ ID NO: 30);
Primers for preparation of variant enzyme N31Q:
Sense primer 5'-gac gga caa ggc cga tgg gca aaa-3' (SEQ ID NO: 31),
Antisense primer 5'-cca tcg gcc ttg tcc gtc cat aat-3' (SEQ ID NO: 32);
Primers for preparation of variant enzyme N77Q:
Sense primer 5'-act gaa caa tgg tct cgt cct aaa g-3' (SEQ ID NO: 33),
Antisense primer 5'-cga gac cat gct tca gtt gaa aat gc-3' (SEQ ID NO: 34);
Primers for preparation of variant enzyme L91G:
Sense primer 5'-gat gaa agg acc ggg tga ttt ttt aa-3' (SEQ ID NO: 35),
Antisense primer 5'-acc cgg tcc ttt cat caa gta att aac-3' (SEQ ID NO: 36);
Primers for preparation of variant enzyme L91K:
Sense primer 5'-gat gaa aaa acc ggg tga ttt ttt aa-3' (SEQ ID NO: 37),
Antisense primer 5'-acc cgg ttt ttt cat caa gta att aa-3' (SEQ ID NO: 38);
Primers for preparation of variant enzyme F95A:
Sense primer 5'-ggg tga tgc gtt aaa cac att ttt ac-3' (SEQ ID NO: 39),
Antisense primer 5'-gtt taa tgc atc acc cgg tag ttt ca-3' (SEQ ID NO: 40);
Primers for preparation of variant enzyme F95W:
Sense primer 5'-ggg tga ttg gtt aaa cac att ttt ac-3' (SEQ ID NO: 41),
Antisense primer 5'-gtt taa cca atc acc cgg tag ttt ca-3' (SEQ ID NO: 42).

The dsDNA template used was pET22b containing the base sequence of *Micrococcus luteus* B-P 26-derived undecaprenyl diphosphate synthase (hereinafter, also referred to as the wild-type enzyme) (this template is referred to as pET22b/MLU-UPS). This pET22b/MLU-UPS was kindly provided by Professor Tanetoshi Koyama (Institute of Multidisciplinary Research for Advanced Materials Tohoku University). 2 µl of 10×Pfu polymerase buffer was mixed with 2-20 ng of the dsDNA template, 50 ng of the sense primer, 50 ng of the antisense primer, 0.4 µl of dNTPs (2.5 mM each), ddH$_2$O up to 20 µl, 0.4 ml of Pfu polymerase (2.5 U/µl) and PCR reaction was then performed. The PCR reaction was performed under the following conditions: 1 cycle of 95° C. for 30 sec; 15 cycles of 95° C. for 30 sec, 55° C. for 1 min, 68° C. for 8 min. After PCR, 0.4 µl of DpnI was added to the PCR reaction solution and DpnI treatment was performed at 37° C. for 1 hour. *E. coli* DH5α was transformed by the heat shock method using 1-10 µl of the DpnI-treated solution, and the transformant was applied to an LB agar medium containing 50 µg/mL ampicillin and then cultured overnight at 37° C., and then the transformed strain was selected. The transformant was cultured all night in an LB medium containing 50 µg/ml ampicillin. A plasmid was prepared by the alkali-SDS method from the obtained culture solution. Mutagenesis in the plasmid was confirmed using a sequencer.

Production Example 13

Production of Protein Having Prenyltransferase Activity

E. coli BL21 (DE3) was transformed with each plasmid pET22b/MLU-UPS (wild-type and variant). The obtained E. coli BL21(DE3)/pET22b/MLU-UPS (wild-type and variant) was inoculated into a test tube containing 3 mL of an LB medium containing 50 μg/mL ampicillin and shake-cultured at 37° C. for 5 hours. A 1 mL aliquot of the obtained culture solution was inoculated into a 500-mL Erlenmeyer flask containing 100 mL of an LB medium containing 50 μg/mL ampicillin and shake-cultured at 37° C. for 3 hours. Then, IPTG was added thereto at a concentration of 0.1 mmol/L, and the bacterial cells were shake-cultured at 30° C. for 18 hours. The culture solution was centrifuged to obtain wet bacterial cells.

The wet bacterial cells thus obtained were disrupted by sonication and then centrifuged. A protein having prenyltransferase activity was purified from the obtained supernatant using HisTrap (manufactured by Amersham Biosciences Corp.). The purification of the purified protein was confirmed by SDS-PAGE.

Examples and Comparative Examples

Preparation of Isoprene Oligomer

A reaction solution containing 10 mg of each purified protein, 50 mM Tris-HCl buffer (pH 7.5), 40 mM magnesium chloride, 40 mM Triton X-100, 25 mM 2-mercaptoethanol, 1 mM of an initiating substrate (farnesyl diphosphate or each of the initiating substrates prepared in Production Examples 1 to 11), and 1 mM isopentenyl diphosphate was prepared and reacted for 1 hour in a water bath at 37° C.

After the completion of reaction, 100 ml of saturated saline and 500 ml of 1-butanol were added thereto, and the mixture was stirred and then left at rest. Then, the supernatant (1-butanol layer) was concentrated to dryness by evaporation. A portion of the residue was structurally confirmed by NMR to obtain an isoprene oligomer.

The details (n and m in the formula (1)) of the thus obtained isoprene oligomers are as shown in Tables 1 and 2. Here, Y was a hydroxy group or a group represented by the formula (2).

In these examples, n and m in the formula (1) were calculated on the basis of information about the initiating substrate used and the length of the isoprene chain determined by TLC. Also, Y was structurally identified by NMR or IR.

TABLE 1

| | | Initiating substrate | | | | | | |
|---|---|---|---|---|---|---|---|---|
| n | | Farnesyl diphosphate | Compound of formula (S) | Compound of formula (B) | Compound of formula (C) | Compound of formula (D) | Compound of formula (E) | Compound of formula (R) |
| Wild-type enzyme | | 3 | 2 | 2 | 2 | 2 | 2 | 2 |
| Variant enzyme | N31A | 3 | 2 | 2 | 2 | 2 | 2 | 2 |
| | N77A | 3 | 2 | 2 | 2 | 2 | 2 | 2 |
| | L91N | 3 | 2 | 2 | 2 | 2 | 2 | 2 |
| | L91D | 3 | 2 | 2 | 2 | 2 | 2 | 2 |
| | N31Q | 3 | 2 | 2 | 2 | 2 | 2 | 2 |
| | N77Q | 3 | 2 | 2 | 2 | 2 | 2 | 2 |
| | L91G | 3 | 2 | 2 | 2 | 2 | 2 | 2 |
| | L91K | 3 | 2 | 2 | 2 | 2 | 2 | 2 |
| | F95A | 3 | 2 | 2 | 2 | 2 | 2 | 2 |
| | F95W | 3 | 2 | 2 | 2 | 2 | 2 | 2 |

| | | Initiating substrate | | | | |
|---|---|---|---|---|---|---|
| n | | Compound of formula (P) | Compound of formula (H) | Compound of formula (M) | Compound of formula (N) | Compound of formula (K) |
| Wild-type enzyme | | 2 | 2 | 2 | 2 | 1 |
| Variant enzyme | N31A | 2 | 2 | 2 | 2 | 1 |
| | N77A | 2 | 2 | 2 | 2 | 1 |
| | L91N | 2 | 2 | 2 | 2 | 1 |
| | L91D | 2 | 2 | 2 | 2 | 1 |
| | N31Q | 2 | 2 | 2 | 2 | 1 |
| | N77Q | 2 | 2 | 2 | 2 | 1 |
| | L91G | 2 | 2 | 2 | 2 | 1 |
| | L91K | 2 | 2 | 2 | 2 | 1 |

TABLE 1-continued

| | | | | | | |
|---|---|---|---|---|---|---|
| | F95A | 2 | 2 | 2 | 2 | 1 |
| | F95W | 2 | 2 | 2 | 2 | 1 |

TABLE 2

| | | Initiating substrate | | | | | | |
|---|---|---|---|---|---|---|---|---|
| | m | Farnesyl diphosphate | Compound of formula (S) | Compound of formula (B) | Compound of formula (C) | Compound of formula (D) | Compound of formula (E) | Compound of formula (R) |
| Wild-type enzyme | | 7, 8, 9 | 3, 4, 5, 6, 7 | 5, 6, 7, 8, 9 | 4, 5, 6, 7 | 4, 5, 6, 7 | 4, 5, 6, 7 | 4, 5, 6, 7 |
| Variant enzyme | N31A | 7, 8, 9 | 4, 5, 6, 7 | 4, 5, 6, 7, 8, 9 | 4, 5, 6, 7 | 4, 5, 6, 7 | 4, 5, 6, 7 | 4, 5, 6, 7 |
| | N77A | 8, 9 | 1, 4, 5, 6 | 6, 7, 8, | 1, 4, 5, 6 | 5, 6 | 5, 6 | 5, 6 |
| | L91N | 8, 9 | 3, 4, 5 | 6, 7, 8, | 3, 4, 5, 6 | 3, 4, 5 | 3, 4, 5 | 3, 4, 5 |
| | L91D | 8, 9 | 3, 4, 5 | 5, 6, 7, 8 | 4, 5, 6 | 4, 5, 6 | 4, 5 | 4, 5, 6 |
| | N31Q | 7, 8, 9 | 4, 5, 6, 7 | 4, 5, 6, 7, 8, 9 | 4, 5, 6, 7 | 4, 5, 6, 7 | 4, 5 | 4, 5, 6, 7 |
| | N77Q | 8, 9 | 3, 4, 5 | 4, 5, 6, 7, 8, 9 | 4, 5, 6, 7, 8 | 4, 5, 6 | 4, 5 | 4, 5, 6, 7 |
| | L91G | 7, 8, 9 | 3, 4, 5 | 6, 7, 8, | 3, 4, 5, 6 | 3, 4, 5 | 4, 5, 6, 7 | 4, 5, 6, 7 |
| | L91K | 8, 9 | 3, 4, 5 | 6, 7, 8, | 3, 4, 5, 6 | 4, 5, 6, 7 | 4, 5 | 4, 5, 6, 7 |
| | F95A | 8, 9, 10 | 3, 4, 5 | 5, 6, 7, 8 | 3, 4, 5, 6, 7 | 5, 6, 7, 8 | 4, 5, 6, 7, 8 | 3, 4, 5 |
| | F95W | 8, 9, 10 | 3, 4, 5 | 5, 6, 7, 8 | 3, 4, 5, 6, 7 | 5, 6, 7, 8 | 4, 5, 6, 7, 8 | 3, 4, 5 |

| | | Initiating substrate | | | | |
|---|---|---|---|---|---|---|
| | m | Compound of formula (P) | Compound of formula (H) | Compound of formula (M) | Compound of formula (N) | Compound of formula (K) |
| Wild-type enzyme | | 3, 4, 5, 6 | 7, 8, 9 | 4, 5, 6, 7 | 3, 4, 5, 6 | 3, 4, 5, 6 |
| Variant enzyme | N31A | 3, 4, 5, 6 | 7, 8, 9 | 4, 5, 6 | 4, 5, 6, 7 | 5, 6, 7 |
| | N77A | 2, 3, 4, 5, 6 | 7, 8, 9 | 4, 5, 6 | 4, 5, 6 | 4, 5, 6 |
| | L91N | 2, 3, 4, 5, 6 | 8, 9 | 3, 4, 5, 6 | 3, 4, 5 | 3, 4, 5 |
| | L91D | 3, 4, 5, 6 | 8, 9 | 4, 5, 6 | 3, 4, 5 | 3, 4, 5 |
| | N31Q | 2, 3, 4, 5, 6 | 7, 8, 9 | 4, 5, 6, 7 | 5, 6, 7 | 5, 6, 7 |
| | N77Q | 2, 3, 4, 5, 6 | 8, 9 | 4, 5, 6 | 3, 4, 5 | 3, 4, 5 |
| | L91G | 4, 5, 6 | 7, 8, 9 | 3, 4, 5, 6 | 3, 4, 5, 6 | 4, 5, 6 |
| | L91K | 4, 5 | 8, 9 | 3, 4, 5, 6 | 3, 4, 5 | 3, 4, 5 |
| | F95A | 4, 5 | 7, 8, 9 | 3, 4, 5, 6, 7 | 3, 4, 5 | 3, 4, 5, 6 |
| | F95W | 4, 5 | 7, 8, 9 | 3, 4, 5, 6, 7 | 3, 4, 5 | 3, 4, 5, 6 |

Examples and Comparative Examples

Comparison of Activity Between Wild-Type Enzyme and Variant Enzyme (Initiating Substrate-Based Relative Activity)

Reaction was performed under conditions shown below using each of the initiating substrates prepared in Production Examples 1 to 11 or farnesyl diphosphate. The activity of each variant enzyme on each initiating substrate was indicated by index with the activity of the wild-type enzyme (*Micrococcus luteus* B-P 26-derived undecaprenyl diphosphate synthase) as 100.

A reaction solution containing 500 ng of each purified protein, 50 mM Tris-HCl buffer (pH 7.5), 40 mM magnesium chloride, 40 mM Triton X-100, 25 mM 2-mercaptoethanol, 12.5 μM of an initiating substrate, and 50 μM [1-$^{14}$C] isopentenyl diphosphate was prepared and reacted for 1 hour in a water bath at 37° C. After the reaction, liquid scintillation counting and TLC quantification were performed to measure the activity of each enzyme.

TABLE 3

| | | Initiating substrate | | | | | | |
|---|---|---|---|---|---|---|---|---|
| Relative activity | | Farnesyl diphosphate | Compound of formula (S) | Compound of formula (B) | Compound of formula (C) | Compound of formula (D) | Compound of formula (E) | Compound of formula (R) |
| Wild-type enzyme | | 100 | 100 | 100 | 100 | 100 | 100 | 100 |
| Variant enzyme | N31A | 123 | 116 | 116 | 111 | 179 | 222 | 200 |
| | N77A | 213 | — | 319 | 234 | 208 | 396 | 254 |
| | L91N | 156 | — | — | 108 | 103 | 271 | 137 |
| | L91D | 231 | 227 | 231 | 155 | 125 | 320 | 230 |
| | N31Q | — | — | — | — | 104 | 210 | 146 |
| | N77Q | 121 | — | — | — | 124 | 194 | 156 |
| | L91G | — | 130 | 149 | 146 | 134 | 170 | 110 |
| | L91K | 133 | 147 | 156 | 130 | 101 | 163 | 165 |
| | F95A | — | 163 | 128 | — | — | 120 | 140 |
| | F95W | — | 130 | 140 | — | 120 | 114 | 121 |

TABLE 3-continued

|  |  | Initiating substrate | | | | |
|---|---|---|---|---|---|---|
| Relative activity | | Compound of formula (P) | Compound of formula (H) | Compound of formula (M) | Compound of formula (N) | Compound of formula (K) |
| Wild-type enzyme | | 100 | 100 | 100 | 100 | 100 |
| Variant enzyme | N31A | — | 152 | 149 | — | — |
| | N77A | — | 162 | 127 | 112 | — |
| | L91N | — | — | 139 | — | — |
| | L91D | 112 | — | 123 | — | — |
| | N31Q | — | 110 | 101 | — | — |
| | N77Q | — | — | — | 133 | — |
| | L91G | 104 | — | — | — | — |
| | L91K | — | — | 112 | — | 112 |
| | F95A | 104 | — | — | 132 | 136 |
| | F95W | 130 | — | — | 147 | 148 |

Examples and Comparative Examples

Preparation of Polyisoprene

A reaction solution containing 10 µl of a latex component, 50 mM Tris-HCl buffer (pH 7.5), 25 mM magnesium chloride, 40 mM 2-mercaptoethanol, 40 mM potassium fluoride, 50 µM of an isoprene oligomer, and 1 mM isopentenyl diphosphate was prepared and reacted for 3 days in a water bath at 30° C. After the reaction, the molecular weight was measured by GPC. Then, n and q in the formula (4) were calculated on the basis of the measured molecular weight and information about the initiating substrate used. The details (n and q in the formula (4)) of the thus obtained polyisoprenes are as shown in Tables 4 and 5. Here, Y was a hydroxy group or a group represented by the formula (2). Also, Y was identified in the same way as in Examples (Preparation of isoprene oligomer).

The latex component used was a serum prepared by the ultracentrifugation of latex taken from *Hevea brasiliensis.*

Each isoprene oligomer used was an isoprene oligomer obtained using the variant enzyme N31A or the like and each initiating substrate (farnesyl diphosphate or each of the initiating substrates prepared in Production Examples 1 to 11) under the same conditions as in Examples (Preparation of isoprene oligomer). In the description below, the isoprene oligomers obtained using the variant enzyme N31A or the like together with farnesyl diphosphate, the compound represented by the formula (S), the compound represented by the formula (B), the compound represented by the formula (C), the compound represented by the formula (D), the compound represented by the formula (E), the compound represented by the formula (R), the compound represented by the formula (P), the compound represented by the formula (H), the compound represented by the formula (M), the compound represented by the formula (N), and the compound represented by the formula (K) as initiating substrates under the same conditions as in Examples (Preparation of isoprene oligomer) are referred to as isoprene oligomer (O), isoprene oligomer (S), isoprene oligomer (B), isoprene oligomer (C), isoprene oligomer (D), isoprene oligomer (E), isoprene oligomer (R), isoprene oligomer (P), isoprene oligomer (H), isoprene oligomer (M), isoprene oligomer (N), and isoprene oligomer (K), respectively.

TABLE 4

|  |  | Isoprene oligomer | | | | | | |
|---|---|---|---|---|---|---|---|---|
| | n | Isoprene oligomer (O) | Isoprene oligomer (S) | Isoprene oligomer (B) | Isoprene oligomer (C) | Isoprene oligomer (D) | Isoprene oligomer (E) | Isoprene oligomer (R) |
| Wild-type enzyme | | 3 | 2 | 2 | 2 | 2 | 2 | 2 |
| Variant enzyme N31A | | 3 | 2 | 2 | 2 | 2 | 2 | 2 |
| | N77A | 3 | 2 | 2 | 2 | 2 | 2 | 2 |
| | L91N | 3 | 2 | 2 | 2 | 2 | 2 | 2 |
| | L91D | 3 | 2 | 2 | 2 | 2 | 2 | 2 |
| | N31Q | 3 | 2 | 2 | 2 | 2 | 2 | 2 |
| | N77Q | 3 | 2 | 2 | 2 | 2 | 2 | 2 |
| | L91G | 3 | 2 | 2 | 2 | 2 | 2 | 2 |
| | L91K | 3 | 2 | 2 | 2 | 2 | 2 | 2 |
| | F95A | 3 | 2 | 2 | 2 | 2 | 2 | 2 |
| | F95W | 3 | 2 | 2 | 2 | 2 | 2 | 2 |
|  |  | Isoprene oligomer | | | | | | |
| | n | Isoprene oligomer (P) | Isoprene oligomer (H) | Isoprene oligomer (M) | Isoprene oligomer (N) | Isoprene oligomer (K) | | |
| Wild-type enzyme | | 2 | 2 | 2 | 2 | 1 | | |
| Variant enzyme N31A | | 2 | 2 | 2 | 2 | 1 | | |
| | N77A | 2 | 2 | 2 | 2 | 1 | | |
| | L91N | 2 | 2 | 2 | 2 | 1 | | |
| | L91D | 2 | 2 | 2 | 2 | 1 | | |

TABLE 4-continued

|   |   |   |   |   |   |
|---|---|---|---|---|---|
| N31Q | 2 | 2 | 2 | 2 | 1 |
| N77Q | 2 | 2 | 2 | 2 | 1 |
| L91G | 2 | 2 | 2 | 2 | 1 |
| L91K | 2 | 2 | 2 | 2 | 1 |
| F95A | 2 | 2 | 2 | 2 | 1 |
| F95W | 2 | 2 | 2 | 2 | 1 |

TABLE 5

| q | | Isoprene oligomer (O) | Isoprene oligomer (S) | Isoprene oligomer (B) | Isoprene oligomer (C) | Isoprene oligomer (D) | Isoprene oligomer (E) | Isoprene oligomer (R) |
|---|---|---|---|---|---|---|---|---|
| Wild-type enzyme | | 5000-30000 | 3000-10000 | 3000-15000 | 5000-30000 | 4500-15000 | 3000-12000 | 3000-12000 |
| Variant enzyme | N31A | 3000-15000 | 1000-7350 | 3000-15000 | 3000-10000 | 3000-10000 | 3000-12000 | 3000-12000 |
| | N77A | 3000-10000 | 1000-7350 | 4000-12000 | 3000-10000 | 5000-20000 | 5000-10000 | 5000-10000 |
| | L91N | 1000-12000 | 1000-6500 | 4000-12000 | 1000-12000 | 5000-20000 | 5000-8000 | 5000-8000 |
| | L91D | 10000-30000 | 1000-6500 | 3000-10000 | 1000-12000 | 1000-12000 | 1500-7000 | 1500-7000 |
| | N31Q | 3000-15000 | 2000-10000 | 3000-15000 | 3500-30000 | 1000-12000 | 2000-7500 | 2000-7500 |
| | N77Q | 3000-15000 | 1000-7350 | 3000-15000 | 3000-15000 | 3500-10000 | 1500-6500 | 1500-6500 |
| | L91G | 3000-15000 | 1000-7350 | 3000-10000 | 3000-20000 | 3000-15000 | 1500-7500 | 2000-7500 |
| | L91K | 3000-15000 | 1500-7350 | 3000-10000 | 3000-15000 | 1500-8000 | 3000-12000 | 1500-6500 |
| | F95A | 700-1000 | 3000-7350 | 5000-20000 | 2000-10000 | 1700-7500 | 1500-10000 | 1500-8000 |
| | F95W | 700-1000 | 3000-7350 | 5000-20000 | 1500-8000 | 1500-7500 | 1500-10000 | 1000-8000 |

| q | | Isoprene oligomer (P) | Isoprene oligomer (H) | Isoprene oligomer (M) | Isoprene oligomer (N) | Isoprene oligomer (K) |
|---|---|---|---|---|---|---|
| Wild-type enzyme | | 1000-3500 | 1000-12000 | 4000-10000 | 1500-7000 | 100-1500 |
| Variant enzyme | N31A | 800-5000 | 3000-12000 | 3000-10000 | 1500-5000 | 150-1500 |
| | N77A | 800-5000 | 1500-7000 | 2000-7000 | 3000-6000 | 200-1500 |
| | L91N | 1000-2000 | 2000-7500 | 2000-7500 | 3000-6000 | 200-1500 |
| | L91D | 1000-3000 | 1500-6500 | 1500-6500 | 1000-7500 | 150-2500 |
| | N31Q | 1500-4000 | 1500-7000 | 1000-7000 | 1500-6000 | 100-1500 |
| | N77Q | 1000-3000 | 2000-7500 | 2000-7500 | 2000-5000 | 250-2000 |
| | L91G | 1000-2500 | 1500-6500 | 1500-10000 | 1500-5000 | 250-1500 |
| | L91K | 1000-4500 | 2000-7500 | 2000-7500 | 2500-8000 | 100-1500 |
| | F95A | 450-1500 | 2000-7000 | 2000-6500 | 3000-8000 | 250-2500 |
| | F95W | 450-2000 | 1500-6500 | 1500-6500 | 3000-8000 | 250-2500 |

(Antimicrobial Test)

An antimicrobial test was conducted using isoprene oligomers obtained using the variant enzyme N31A under the same conditions as in Examples (Preparation of isoprene oligomer). The isoprene oligomers used were the isoprene oligomer (O), the isoprene oligomer (S), the isoprene oligomer (B), the isoprene oligomer (C), the isoprene oligomer (D), the isoprene oligomer (E), the isoprene oligomer (R), the isoprene oligomer (P), the isoprene oligomer (H), the isoprene oligomer (M), the isoprene oligomer (N), and the isoprene oligomer (K).

The following microbial strains were used in the antimicrobial test:
Gram-positive bacteria: *Staphylococcus aureus* (13276) and *Bacillus subtilis* (3134)
Gram-negative bacteria: *Echerichia coli* (3972), *Salmonella enteric* (100797), *Peudomonas aeruginosa* (13275), and *Klebsiella pneumonia* (3512)
Fungi: *Candida albicans* (1594)
The number in the parentheses represents NBRC No. from National Institute of Technology and Evaluation, Biological Resource Center. All the microbial strains used were purchased from NBRC.

Next, the recovery and culture conditions of the microbial strains used are shown in Table 6.

TABLE 6

| NBRC No. | Liquid culture | Solid medium | Culture temperature (° C.) |
|---|---|---|---|
| 1594 | 703 | 108 | 24 |
| 3134 | 702 | 802 | 30 |
| 3512 | 702 | 802 | 30 |
| 3972 | 702 | 802 | 30 |
| 13275 | 702 | 802 | 30 |
| 13276 | 702 | 802 | 30 |
| 100797 | 702 | 802 | 30 |

Composition of each medium (1 L solution each)
108: 10 g of glucose, 5 g of peptone, 3 g of yeast extract, 3 g of malt extract, and 15 g of agar, pH 5.6;
702: 10 g of polypeptone, 2 g of yeast extract, and 1 g of $MgSO_4 \cdot 7H_2O$, pH 7.0;
703: 10 g of glucose, 5 g of peptone, 3 g of yeast extract, and 3 g of malt extract, pH 6.0;
802: 10 g of polypeptone, 2 g of yeast extract, 1 g of $MgSO_4 \cdot 7H_2O$, and 15 g of agar, pH 7.0.

The *Staphylococcus aureus* strain was inoculated into a test tube containing 2 ml of a liquid medium (10 g/L polypeptone, 2 g/L yeast extract, and 1 g/L $MgSO_4 \cdot 7H_2O$, pH 7.0) and cultured at 150 rpm at 30° C. for 5 hours. The microbial strain was inoculated into a solid medium (10 g/L polypeptone, 2 g of yeast extract, 1 g/L MgSO$_4$.7H$_2$O, and 15 g/L agar, pH 7.0) and cultured overnight at 30° C. On the next day, colonies were confirmed. One of the colonies on the solid medium was inoculated into a test tube containing 4 ml of the liquid medium and cultured (i.e., precultured) overnight at 30° C. Next, 100 µl of the preculture solution was added to a new test tube containing 4 ml of the liquid medium and cultured at 150 rpm at 30° C. During the culture, the turbidity was measured using a spectrophotometer, and the culture was continued until O.D.600=0.1 to 0.3. The culture solution was adjusted to 10$^5$ cfu/ml by the dilution method and used in the antimicrobial test.

The minimum inhibitory concentration (MIC) was measured by the MIC method, which is a general experimental approach for examining the activity of anti-microorganism substances. The microbial culture solution thus adjusted to 10$^5$ cfu/ml and each isoprene oligomer adjusted to 0.5-5 mM were added into a 1.5-ml tube, mixed with each other, and cultured overnight at 150 rpm at 30° C. After the culture, each concentration of the culture solution was applied to the solid medium using a spreader and cultured at 30° C. for 1-4 days. After the culture, the presence or absence of growth of the microbe was examined by visual observation, and the minimum addition concentration of the terminally modified isoprene oligomer at which the microbe did not survive was defined as MIC.

MIC was determined for the other microbes in the same way as above.

The isoprene oligomers used and their MICs are shown in Table 7.

structural moiety was not replaced by another atom or group did not exhibit antimicrobial activity (antimicrobial activity was not observed at 800 ppm or lower). In contrast, the isoprene oligomers of Examples in which at least one atom or group contained in the trans structural moiety was replaced by another atom or group exhibited antimicrobial activity.

(Rubber Composition)

Next, a rubber composition containing the isoprene oligomer and/or the polyisoprene of the present invention was evaluated for its performance. First, the compound represented by the formula (F) was synthesized in the same way as in Production Examples 1 to 11.

Next, farnesyl diphosphate and the synthesized initiating substrates (the compound represented by the formula (K) and the compound represented by the formula (F)) were used to prepare isoprene oligomers. The details (n, m, and Y in the formula (1)) of the obtained isoprene oligomers were determined in the same way as in Examples (Preparation of isoprene oligomer).

Production Example 14

Preparation of Isoprene Oligomer (F)

The isoprene oligomer (F) was prepared from the compound represented by the formula (F) as an initiating substrate. This reaction was performed by adjusting the conditions described above in (Preparation of isoprene oligomer) in order to adjust the molecular weight of the isoprene oligomer to be obtained.

TABLE 7

| MIC(µg/ml) | | Comparative Example 1 Isoprene oligomer (O) | Example 1 Isoprene oligomer (S) | Example 2 Isoprene oligomer (B) | Example 3 Isoprene oligomer (C) | Example 4 Isoprene oligomer (D) | Example 5 Isoprene oligomer (E) | Example 6 Isoprene oligomer (R) |
|---|---|---|---|---|---|---|---|---|
| Staphylococcus aureus | 13276 | * | — | 260 | 160 | 560 | 460 | 58 |
| Bacillus subtilis | 3134 | * | — | 260 | 160 | 560 | 320 | 58 |
| Echerichia coli | 3972 | * | — | 180 | — | 240 | — | 130 |
| Salmonella enteric | 100797 | * | — | — | — | — | — | — |
| Peudomonas aeruginosa | 13275 | * | 93 | — | — | — | — | — |
| Klebsiella pneumonia | 3512 | * | 93 | 58 | — | — | — | — |
| Candida albicans | 1594 | * | 93 | — | — | 240 | 90 | 130 |

| MIC(µg/ml) | | Example 7 Isoprene oligomer (P) | Example 8 Isoprene oligomer (H) | Example 9 Isoprene oligomer (M) | Example 10 Isoprene oligomer (N) | Example 11 Isoprene oligomer (K) |
|---|---|---|---|---|---|---|
| Staphylococcus aureus | 13276 | 140 | — | 190 | 560 | 45 |
| Bacillus subtilis | 3134 | 140 | — | 760 | 560 | 30 |
| Echerichia coli | 3972 | — | — | 420 | 240 | 30 |
| Salmonella enteric | 100797 | — | — | 240 | 37 | 50 |
| Peudomonas aeruginosa | 13275 | — | — | — | 37 | 56 |
| Klebsiella pneumonia | 3512 | — | — | — | 130 | 75 |
| Candida albicans | 1594 | — | 88 | — | 20 | 35 |

* Antimicrobial activity was not observed at 800 ppm or lower.

(Discussion about Results of Table 7)

The isoprene oligomer (O) of Comparative Example (isoprene oligomer obtained from farnesyl diphosphate) in which at least one atom or group contained in the trans The details (n and m in the formula (1)) of the obtained isoprene oligomer (F) were n=2 and m=5 to 8. Here, Y was a hydroxy group or a group represented by the formula (2).

Production Example 15

Preparation of Isoprene Oligomer (K)

The isoprene oligomer (K) was prepared from the compound represented by the formula (K) as an initiating substrate. This reaction was performed by adjusting the conditions described above in (Preparation of isoprene oligomer) in order to adjust the molecular weight of the isoprene oligomer to be obtained.

The details (n and m in the formula (1)) of the obtained isoprene oligomer (K) were n=1 and m=5 to 7. Here, Y was a hydroxy group or a group represented by the formula (2).

Production Example 16

Preparation of Isoprene Oligomer (O)

The isoprene oligomer (O) was prepared from farnesyl diphosphate as an initiating substrate. This reaction was performed by adjusting the conditions described above in (Preparation of isoprene oligomer) in order to adjust the molecular weight of the isoprene oligomer to be obtained.

The details (n and m in the formula (1)) of the obtained isoprene oligomer (O) were n=3 and m=5 to 7. Here, Y was a hydroxy group or a group represented by the formula (2).

Next, polyisoprenes were prepared from the isoprene oligomers obtained in Production Examples 14 to 16 (the isoprene oligomer (F), the isoprene oligomer (K), and the isoprene oligomer (O)). The details (n, q, and Y in the formula (4)) of the obtained polyisoprenes were determined in the same way as in Examples (Preparation of polyisoprene).

Production Example 17

Preparation of Polyisoprene (F)

The polyisoprene (F) was prepared from the isoprene oligomer (F) prepared in Production Example 14. This reaction was performed by adjusting the conditions described above in (Preparation of polyisoprene) in order to adjust the molecular weight of the polyisoprene to be obtained.

The details (n and q in the formula (4)) of the obtained polyisoprene (F) were n=2 and q=7000 to 12000. Here, Y was a hydroxy group or a group represented by the formula (2).

Production Example 18

Preparation of Polyisoprene (K-1)

The polyisoprene (K-1) was prepared from the isoprene oligomer (K) prepared in Production Example 15. This reaction was performed by adjusting the conditions described above in (Preparation of polyisoprene) in order to adjust the molecular weight of the polyisoprene to be obtained.

The details (n and q in the formula (4)) of the obtained polyisoprene (K-1) were n=1 and q=3500 to 7000. Here, Y was a hydroxy group or a group represented by the formula (2).

Production Example 19

Preparation of Polyisoprene (K-2)

The polyisoprene (K-2) was prepared from the isoprene oligomer (K) prepared in Production Example 15. This reaction was performed by adjusting the conditions described above in (Preparation of polyisoprene) in order to adjust the molecular weight of the polyisoprene to be obtained.

The details (n and q in the formula (4)) of the obtained polyisoprene (K-2) were n=1 and q=7000 to 12000. Here, Y was a hydroxy group or a group represented by the formula (2).

Production Example 20

Preparation of Polyisoprene (O)

The polyisoprene (O) was prepared from the isoprene oligomer (O) prepared in Production Example 16. This reaction was performed by adjusting the conditions described above in (Preparation of polyisoprene) in order to adjust the molecular weight of the polyisoprene to be obtained.

The details (n and q in the formula (4)) of the obtained polyisoprene (O) were n=3 and q=7000 to 12000. Here, Y was a hydroxy group or a group represented by the formula (2).

Hereinafter, various agents used in Examples 12 to 21 and Comparative Examples 2 to 6 will be summarized.
NR: TSR20
BR: BR01 manufactured by JSR Corp.
Carbon black: Diablack (N220) manufactured by Mitsubishi Chemical Corp.
Isoprene oligomer (F), isoprene oligomer (K), and isoprene oligomer (O): isoprene oligomers obtained in Production Examples 14 to 16
Polyisoprene (F), polyisoprene (K-1), polyisoprene (K-2), and polyisoprene (O): polyisoprenes obtained in Production Examples 17 to 20
Zinc oxide: zinc oxide No. 1 manufactured by Mitsui Mining & Smelting Co., Ltd.
Stearic acid: stearic acid manufactured by NOF Corp.
Antioxidant: Nocrac 6C (N-(1,3-dimethylbutyl)-N'-phenyl-p-phenylenediamine) manufactured by Ouchi Shinko Chemical Industrial Co., Ltd.
Wax: Sannoc wax manufactured by Ouchi Shinko Chemical Industrial Co., Ltd.
Sulfur: sulfur powder manufactured by Tsurumi Chemical Industry Co., Ltd.
Vulcanization accelerator NS: Nocceler NS (N-tert-butyl-2-benzothiazolesulfenamide) manufactured by Ouchi Shinko Chemical Industrial Co., Ltd.
Silica: Nipsil AQ (wet silica) manufactured by Nippon Silica Industrial Co., Ltd.
Silane coupling agent: Si266 (bis(3-triethoxysilylpropyl) disulfide) manufactured by Degussa
Vulcanization accelerator DPG: Nocceler D (N,N-diphenylguanidine) manufactured by Ouchi Shinko Chemical Industrial Co., Ltd.

Examples 12 to 21 and Comparative Examples 2 to 6

The materials other than sulfur and vulcanization accelerators were kneaded using a 1.7-L Banbury mixer according to the formulation shown in Table 8 or 9 to obtain a kneaded mixture. Next, sulfur and vulcanization accelerator (s) were added to the obtained kneaded mixture and kneaded thereinto using an open roll mill to obtain an unvulcanized rubber composition. The obtained unvulcanized rubber composition was vulcanized at a pressure of 80 kgf/cm² at 150°

C. for 30 minutes using a steam vulcanization press to obtain a vulcanized rubber composition.

The thus obtained vulcanized rubber compositions were evaluated as shown below. The results are shown in Tables 8 and 9. The formulations of Comparative Examples 4 and 5 were used as reference formulations in Tables 8 and 9, respectively.

(Viscoelasticity Test)

The tan δ was measured under conditions of 70° C. and 2% strain (initial elongation) using a viscoelasticity spectrometer manufactured by Iwamoto Seisakusho Co., Ltd. and indicated by index with the tan δ of the reference formulation as 100. A larger index represents larger heat build-up. A rubber composition having an index of 100 or less was regarded as having improved in resistance to heat build-up (low-heat-build-up properties). This means that a rubber composition having a smaller index is more excellent in low-heat-build-up properties.

(Lambourn Abrasion Test)

An abrasion test was carried out for 5 minutes under conditions of 3 kg load, 40% slip ratio, and sand falling at a rate of 15 g/min using a Lambourn abrasion tester manufactured by Iwamoto Seisakusho Co., Ltd. The shape of each sample was set to a thickness of 5 mm and a diameter of 50 mm, and the grindstone used was GC-type abrasive grains having a particle size of #80. The test results were converted to an index with the value of the reference formulation as 100 (reference). A larger index represents more excellent abrasion resistance. A rubber composition having an index exceeding 100 was regarded as having improved in abrasion resistance.

(Tensile Test)

A tensile test was carried out according to JIS K6251 "Rubber, vulcanized or thermoplastic—Determination of tensile stress-strain properties" using No. 3 dumbbell test pieces from the vulcanized rubber sheet, and the tensile strength at break (TB) (MPa) and elongation at break (EB) (%) were measured. Elongation at break less than 480% tends to cause rubber separation during use in large tires and thus requires improvement. Also as for tensile strength at break, its reduction is responsible for the destruction of tires and thus it is necessary to prevent a reduction due to the change in materials.

TABLE 8

| | | Example 12 | Example 13 | Example 14 | Example 15 | Comparative Example 2 | Comparative Example 3 | Comparative Example 4 |
|---|---|---|---|---|---|---|---|---|
| Formulation (Part(s) by mass) | NR | 80 | 80 | 80 | 80 | 80 | 80 | 80 |
| | BR | 20 | 20 | 20 | 20 | 20 | 20 | 20 |
| | Carbon black | 50 | 50 | 50 | 50 | 50 | 50 | 50 |
| | Isoprene oligomer (F) | 3 | 10 | — | — | — | — | — |
| | Isoprene oligomer (K) | — | — | 3 | 10 | — | — | — |
| | Isoprene oligomer (O) | — | — | — | — | 3 | 10 | — |
| | Zinc oxide | 3 | 3 | 3 | 3 | 3 | 3 | 3 |
| | Stearic acid | 2 | 2 | 2 | 2 | 2 | 2 | 2 |
| | Antioxidant | 2 | 2 | 2 | 2 | 2 | 2 | 2 |
| | Wax | 1.5 | 1.5 | 1.5 | 1.5 | 1.5 | 1.5 | 1.5 |
| | Sulfur | 1.5 | 1.5 | 1.5 | 1.5 | 1.5 | 1.5 | 1.5 |
| | Vulcanization accelerator NS | 1 | 1 | 1 | 1 | 1 | 1 | 1 |
| Performance evaluation | Viscoelasticity tan δ (index) | 97 | 94 | 96 | 93 | 102 | 104 | 100 |
| | Lambourn abrasion (index) | 104 | 106 | 103 | 106 | 98 | 96 | 100 |
| | Elongation at break (%) | 520 | 570 | 520 | 580 | 530 | 570 | 510 |

TABLE 9

| | | Example 16 | Example 17 | Example 18 | Example 19 | Example 20 | Example 21 | Comparative Example 5 | Comparative Example 6 |
|---|---|---|---|---|---|---|---|---|---|
| Formulation (Part(s) by mass) | Polyisoprene (F) | 100 | — | — | 80 | 60 | — | — | — |
| | Polyisoprene (K-1) | — | 100 | — | — | — | 60 | — | — |
| | Polyisoprene (K-2) | — | — | 100 | — | — | — | — | — |
| | Polyisoprene (O) | — | — | — | — | — | — | 60 | — |
| | NR | — | — | — | 20 | 40 | 40 | 40 | 100 |
| | Silica | 50 | 50 | 50 | 50 | 50 | 50 | 50 | 50 |
| | Silane coupling agent | 4 | 4 | 4 | 4 | 4 | 4 | 4 | 4 |
| | Stearic acid | 2 | 2 | 2 | 2 | 2 | 2 | 2 | 2 |
| | Antioxidant | 2 | 2 | 2 | 2 | 2 | 2 | 2 | 2 |
| | Zinc oxide | 3 | 3 | 3 | 3 | 3 | 3 | 3 | 3 |
| | Sulfur | 1.5 | 1.5 | 1.5 | 1.5 | 1.5 | 1.5 | 1.5 | 1.5 |
| | Vulcanization accelerator NS | 1 | 1 | 1 | 1 | 1 | 1 | 1 | 1 |
| | Vulcanization accelerator DPG | 1 | 1 | 1 | 1 | 1 | 1 | 1 | 1 |
| Performance evaluation | Viscoelasticity tan δ (index) | 89 | 93 | 88 | 91 | 94 | 93 | 100 | 101 |
| | Lambourn abrasion (index) | 112 | 106 | 111 | 108 | 105 | 106 | 100 | 102 |
| | Tensile strength at break (MPa) | 25.8 | 25.5 | 25.2 | 25.5 | 25.2 | 25.3 | 25.6 | 24.8 |

As is evident from Table 8, the rubber compositions of Examples including the isoprene oligomers in which at least one atom or group contained in the trans structural moiety was replaced by another atom or group were excellent in low-heat-build-up properties, abrasion resistance, and elongation at break.

As is evident from Table 9, the rubber compositions of Examples including the polyisoprenes in which at least one atom or group contained in the trans structural moiety was replaced by another atom or group were excellent in low-heat-build-up properties, abrasion resistance, and tensile strength at break.

Next, the following experiment was conducted in order to demonstrate the fact that by maintaining the structure of moiety I in the formula (I) in the naturally occurring initiating substrate farnesyl diphosphate or the like, even when a desired structure is introduced in a moiety other than moiety I, it is possible to produce isoprene oligomers in the presence of the naturally occurring oligomer-producing enzyme prenyltransferase or any enzyme obtained by partial mutation thereof, whereas this enzymatic reaction does not proceed in the case of using initiating substrates not maintaining the structure of moiety I in the formula (I).

First, the following initiating substrates 1 to 4 not maintaining the structure of moiety I in the formula (I) were synthesized.

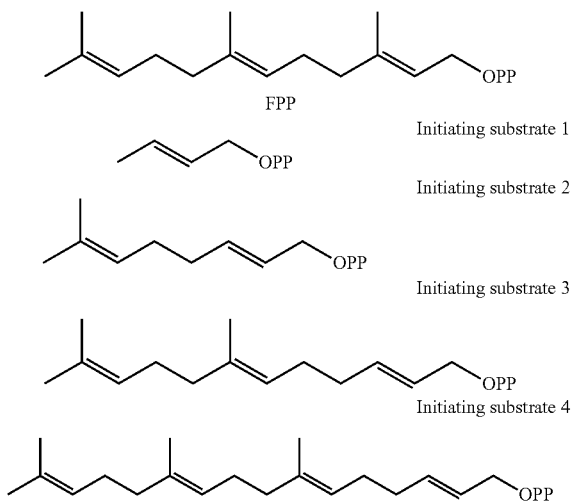

Synthesis of initiating substrate 1 (2E-butenyl diphosphate)

Synthesis was carried out with crotyl alcohol as a starting material. The primary hydroxy group was replaced by chlorine using N-chlorosuccinimide and dimethyl sulfide in an anhydrous dichloromethane solvent to obtain a chloride (compound represented by (i) below) (yield: 78%). Next, the chloride was diphosphorylated using tris-tetra-n-butylammonium hydrogen pyrophosphate in anhydrous acetonitrile to obtain a compound represented by (ii) below (initiating substrate 1) as the substance of interest (yield: 50%). The intermediate in each synthesis step and the final product were confirmed by TLC and instrumental analysis (IR, NMR).

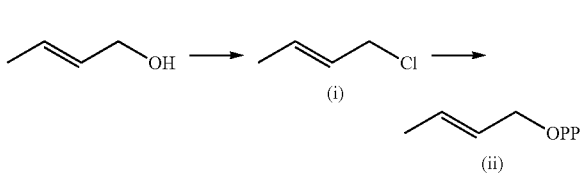

Synthesis of initiating substrate 2
(7-methyl-octa-2E,6E-dienyl diphosphate)

Synthesis was carried out with 3-methyl-2-buten-1-ol as a starting material. The hydroxy group of 3-methyl-2-buten-1-ol was chlorinated using N-chlorosuccinimide (NCS) and dimethyl sulfide (DMS) in anhydrous dichloromethane in a nitrogen atmosphere to obtain a chloride (compound represented by (i) below) (yield: 90%). Next, the chloride was reacted with ethyl cyanoacetate in the presence of lithium hydroxide in anhydrous N,N-dimethylformamide to obtain an ester form (compound represented by (ii) below) (yield: 44%). Next, the ester was hydrolyzed with potassium hydroxide and methanol to obtain a carboxylic acid (compound represented by (iii) below) (yield: 92%). Next, the carboxylic acid was decarboxylated with dimethyl sulfoxide and common salt to obtain a nitrile form (compound represented by (iv) below) (yield: 40%). The nitrile was reduced with lithium diisobutyl hydride and saturated ammonium chloride in anhydrous dichloromethane to obtain an aldehyde form (compound represented by (v) below) (yield: 89%). The aldehyde was treated with sodium hydride and ethyl diethylphosphonoacetate in anhydrous tetrahydrofuran to obtain a trans ester form (compound represented by (vi) below) (yield: 84%). Next, the ester was reduced using lithium diisobutyl hydride and methanol in anhydrous dichloromethane and anhydrous hexane to obtain an alcohol form (compound represented by (vii) below) (yield: 19%). Next, the primary hydroxy group was replaced by chlorine using N-chlorosuccinimide and dimethyl sulfide in an anhydrous dichloromethane solvent at −40° C. or lower to obtain a chloride (compound represented by (viii) below) (yield: 82%). Next, the chloride was diphosphorylated using tris-tetra-n-butylammonium hydrogen pyrophosphate in anhydrous acetonitrile to obtain a compound represented by (ix) below (initiating substrate 2) as the substance of interest (yield: 50%). The intermediate in each synthesis step and the final product were confirmed by TLC and instrumental analysis (IR, NMR).

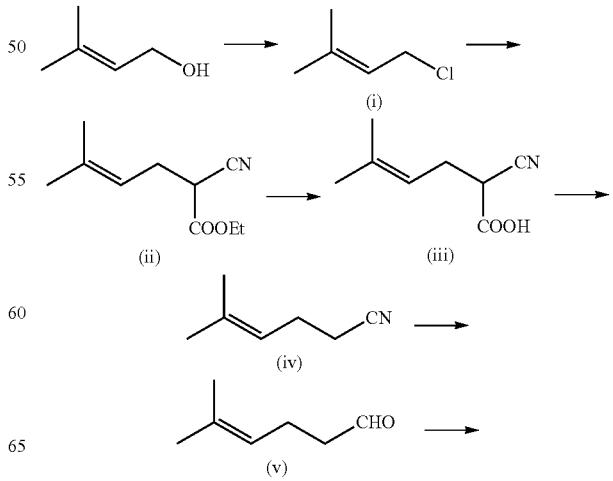

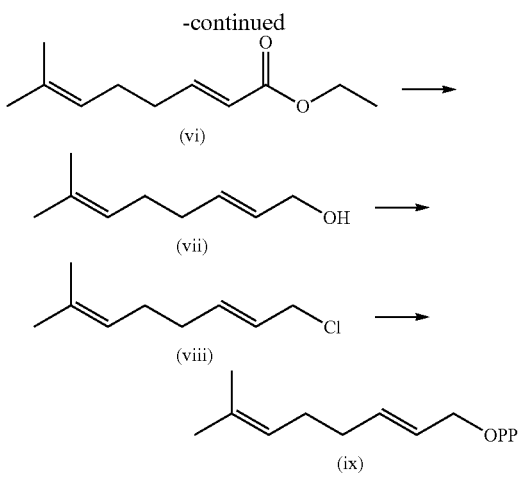

Synthesis of initiating substrate 3 (7,11-dimethyl-dodeca-2E,6E,10E-trienyl diphosphate)

Synthesis was carried out with geraniol as a starting material. The hydroxy group of geraniol was chlorinated using N-chlorosuccinimide (NCS) and dimethyl sulfide (DMS) in anhydrous dichloromethane in a nitrogen atmosphere to obtain a chloride (compound represented by (i) below) (yield: 94%). Next, the chloride was reacted with ethyl cyanoacetate in the presence of lithium hydroxide in anhydrous N,N-dimethylformamide to obtain an ester form (compound represented by (ii) below) (yield: 34%). Next, the ester was hydrolyzed with potassium hydroxide and methanol to obtain a carboxylic acid (compound represented by (iii) below) (yield: 95%). Next, the carboxylic acid was decarboxylated with dimethyl sulfoxide and common salt to obtain a nitrile form (compound represented by (iv) below) (yield: 40%). The nitrile was reduced with lithium diisobutyl hydride and saturated ammonium chloride in anhydrous dichloromethane to obtain an aldehyde form (compound represented by (v) below) (yield: 91%). The aldehyde was treated with sodium hydride and ethyl diethylphosphonoacetate in anhydrous tetrahydrofuran to obtain a trans ester form (compound represented by (vi) below) (yield: 82%). Next, the ester was reduced using lithium diisobutyl hydride and methanol in anhydrous dichloromethane and anhydrous hexane to obtain an alcohol form (compound represented by (vii) below) (yield: 19%). Next, the primary hydroxy group was replaced by chlorine using N-chlorosuccinimide and dimethyl sulfide in an anhydrous dichloromethane solvent to obtain a chloride (compound represented by (viii) below) (yield: 82%). Next, the chloride was diphosphorylated using tris-tetra-n-butylammonium hydrogen pyrophosphate in anhydrous acetonitrile to obtain a compound represented by (ix) below (initiating substrate 3) as the substance of interest (yield: 42%). The intermediate in each synthesis step and the final product were confirmed by TLC and instrumental analysis (IR, NMR).

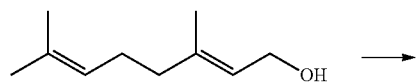

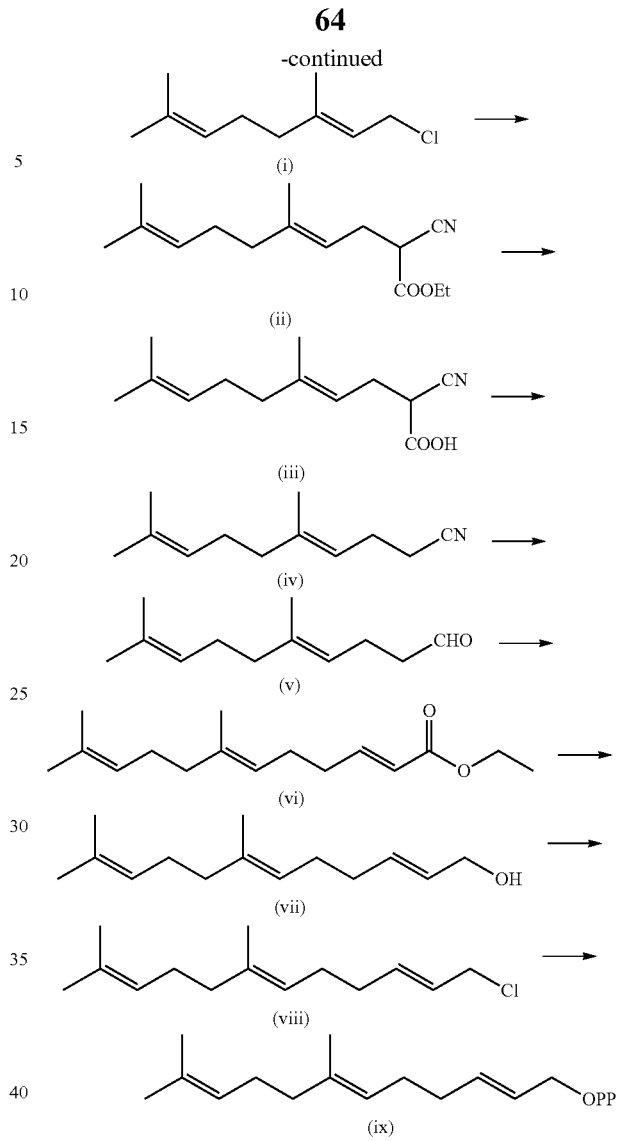

Synthesis of initiating substrate 4 (7,11,15-trimethyl-hexadeca-2E,6E,10E,14E-tetraenyl diphosphate)

Synthesis was carried out with farnesol as a starting material. The hydroxy group of farnesol was chlorinated using N-chlorosuccinimide (NCS) and dimethyl sulfide (DMS) in anhydrous dichloromethane in a nitrogen atmosphere to obtain a chloride (compound represented by (i) below) (yield: 91%). Next, the chloride was reacted with ethyl cyanoacetate in the presence of lithium hydroxide in anhydrous N,N-dimethylformamide to obtain an ester form (compound represented by (ii) below) (yield: 34%). Next, the ester was hydrolyzed with potassium hydroxide and methanol to obtain a carboxylic acid (compound represented by (iii) below) (yield: 88%). Next, the carboxylic acid was decarboxylated with dimethyl sulfoxide and common salt to obtain a nitrile form (compound represented by (iv) below) (yield: 40%). The nitrile was reduced with lithium diisobutyl hydride and saturated ammonium chloride in anhydrous dichloromethane to obtain an aldehyde form (compound represented by (v) below) (yield: 81%). The aldehyde was treated with sodium hydride and ethyl diethylphosphonoacetate in anhydrous tetrahydrofuran to obtain a trans ester form (compound represented by (vi) below) (yield: 84%). Next, the ester was reduced using lithium diisobutyl hydride and methanol in anhydrous dichloromethane and anhydrous hexane to obtain an alcohol form (compound represented by (vii) below) (yield: 30%). Next, the primary hydroxy group was replaced by chlorine using N-chlorosuccinimide and dimethyl sulfide in an anhydrous dichloromethane solvent to obtain a chloride (compound represented by (viii) below) (yield: 86%). Next, the chloride was diphosphorylated using tris-tetra-n-butylammonium hydrogen pyrophosphate in anhydrous acetonitrile to obtain a compound represented by (ix) below (initiating substrate 4) as the substance of interest (yield: 41%). The intermediate in each synthesis step and the final product were confirmed by TLC and instrumental analysis (IR, NMR).

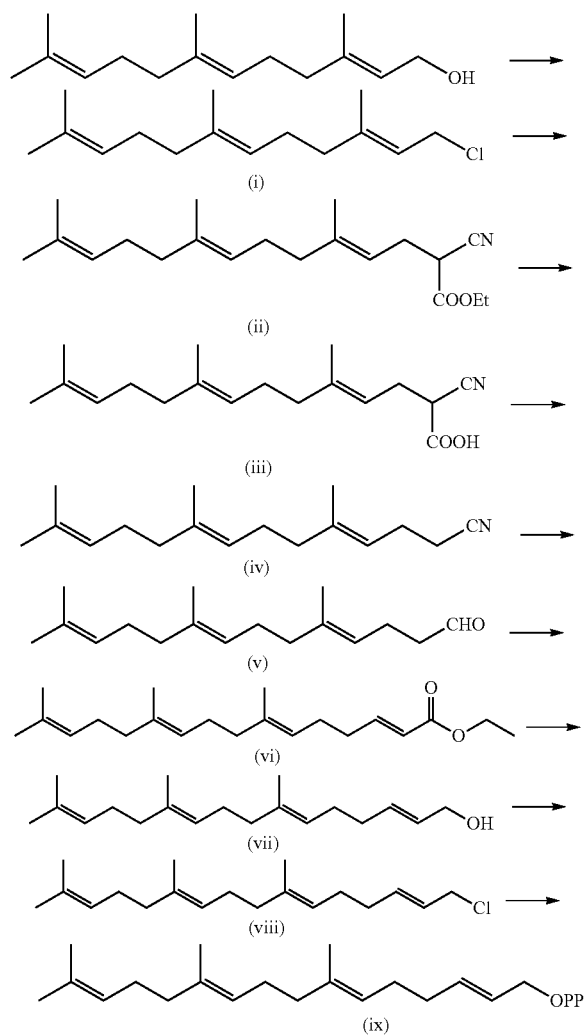

Next, the compound represented by the formula (G), the compound represented by the formula (I), and the compound represented by the formula (Q) were synthesized in the same way as in Production Examples 1 to 11.

Next, reaction was performed under conditions shown below using *Micrococcus luteus* B-P 26-derived undecaprenyl diphosphate synthase as an enzyme and each of the initiating substrates 1 to 4, the compound represented by the formula (B), the compound represented by the formula (C), the compound represented by the formula (G), the compound represented by the formula (K), and farnesyl diphosphate (FPP). The results were indicated in Table 10 by the relative activity of the enzyme on the initiating substrates 1 to 4, the compound represented by the formula (B), the compound represented by the formula (C), the compound represented by the formula (G), and the compound represented by the formula (K) with the activity of the enzyme on farnesyl diphosphate as 100.

A reaction solution containing 500 ng of the enzyme, 50 mM Tris-HCl buffer (pH 7.5), 40 mM magnesium chloride, 40 mM Triton X-100, 25 mM 2-mercaptoethanol, 12.5 µM of an initiating substrate, and 50 µM [1-$^{14}$C] isopentenyl diphosphate was prepared and reacted for 1 hour in a water bath at 37° C. After the reaction, liquid scintillation counting and TLC quantification were performed to measure the activity of the enzyme on each initiating substrate.

TABLE 10

| Initiating substrate | Relative activity (%) |
| --- | --- |
| Farnesyl diphosphate | 100 |
| Initiating substrate 1 | 0.3 |
| Initiating substrate 2 | 0.6 |
| Initiating substrate 3 | 1.2 |
| Initiating substrate 4 | 5.9 |
| Compound of formula (B) | 68.4 |
| Compound of formula (C) | 74.8 |
| Compound of formula (G) | 72.9 |
| Compound of formula (K) | 40.6 |

As is evident from the results of Table 10, the enzymatic reaction hardly proceeded in the case of using the initiating substrates 1 to 4 not maintaining the structure of moiety I in the formula (I). In contrast, the enzymatic reaction proceeded in the case of using the initiating substrates maintaining the structure of moiety I in the formula (I).

Next, the following experiment was conducted using *Bacillus stearothermophilus*-derived farnesyl diphosphate synthase and *Sulfolobus acidocaldarius*-derived geranylgeranyl diphosphate synthase in order to demonstrate the fact that even enzymes having prenyltransferase activity, derived from organisms other than *Micrococcus luteus* B-P 26 exhibit the same tendencies as described for *Micrococcus luteus* B-P 26-derived undecaprenyl diphosphate synthase, depending on whether or not the initiating substrate used has maintained the structure of moiety I in the formula (I).

First, *Bacillus stearothermophilus*-derived farnesyl diphosphate synthase was prepared.

*E. coli* BL21 (DE3) was transformed in the same way as above, with a plasmid pET22b containing the base sequence of *Bacillus stearothermophilus*-derived farnesyl diphosphate synthase (this plasmid is referred to as pET22b/BsFPS). This pET22b/BsFPS was kindly provided by Professor Koyama (Institute of Multidisciplinary Research for Advanced Materials Tohoku University).

The *E. coli* BL21(DE3)/pET22b/BsFPS was inoculated into a test tube containing 3 mL of an LB medium containing 50 µg/mL ampicillin and shake-cultured at 37° C. for 5 hours. A 1 mL aliquot of the obtained culture solution was inoculated into a 500-mL Erlenmeyer flask containing 100 mL of an LB medium containing 50 µg/mL ampicillin and shake-cultured at 37° C. for 3 hours. Then, IPTG was added thereto at a concentration of 0.1 mmol/L, and the bacterial cells were shake-cultured at 30° C. for 18 hours. The culture solution was centrifuged to obtain wet bacterial cells. The wet bacterial cells thus obtained were disrupted by sonication and then centrifuged. A protein having prenyltransferase activity (*Bacillus stearothermophilus*-derived farnesyl diphosphate synthase) was purified from the obtained supernatant using HisTrap (manufactured by Amersham Biosciences Corp.). The purification of the purified protein was confirmed by SDS-PAGE.

Next, *Sulfolobus acidocaldarius*-derived geranylgeranyl diphosphate synthase was prepared.

*E. coli* BL21 (DE3) was transformed in the same way as above, with a plasmid pET22b containing the base sequence of *Sulfolobus acidocaldarius*-derived geranylgeranyl diphosphate synthase (this plasmid is referred to as pET22b/SaGGPS). This pET22b/SaGGPS was kindly provided by Professor Tokuzo Nishino (School of Engineering, Tohoku University).

The *E. coli* BL21(DE3)/pET22b/SaGGPS was inoculated into a test tube containing 3 mL of an LB medium containing 50 μg/mL ampicillin and shake-cultured at 37° C. for 5 hours. A 1 mL aliquot of the obtained culture solution was inoculated into a 500-mL Erlenmeyer flask containing 100 mL of an LB medium containing 50 μg/mL ampicillin and shake-cultured at 37° C. for 3 hours. Then, IPTG was added thereto at a concentration of 0.1 mmol/L, and the bacterial cells were shake-cultured at 30° C. for 18 hours. The culture solution was centrifuged to obtain wet bacterial cells. The wet bacterial cells thus obtained were disrupted by sonication and then centrifuged. A protein having prenyltransferase activity (*Sulfolobus acidocaldarius*-derived geranylgeranyl diphosphate synthase) was purified from the obtained supernatant using HisTrap (manufactured by Amersham Biosciences Corp.). The purification of the purified protein was confirmed by SDS-PAGE.

Reaction was performed under conditions shown below using the obtained *Bacillus stearothermophilus*-derived farnesyl diphosphate synthase and each of the initiating substrates 1 to 4, the compound represented by the formula (F), the compound represented by the formula (I), the compound represented by the formula (Q), and geranyl diphosphate (GPP) whose structure is shown below. The results were indicated in Table 11 by the relative activity of the enzyme on the initiating substrates 1 to 4, the compound represented by the formula (F), the compound represented by the formula (I), and the compound represented by the formula (Q) with the activity of the enzyme on geranyl diphosphate as 100.

A reaction solution containing 500 ng of the purified enzyme, 50 mM Tris-HCl buffer (pH 8.5), 40 mM magnesium chloride, 50 mM ammonium chloride, 40 mM Triton X-100, 25 mM 2-mercaptoethanol, 12.5 μM of an initiating substrate, and 50 μM [1-$^{14}$C] isopentenyl diphosphate was prepared and reacted for 1 hour in a water bath at 55° C. After the reaction, liquid scintillation counting and TLC quantification were performed to measure the activity of the enzyme on each initiating substrate.

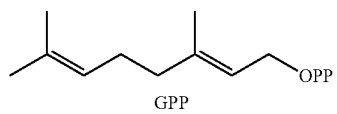

GPP

TABLE 11

| Initiating substrate | Relative activity (%) |
|---|---|
| Geranyl diphosphate | 100 |
| Initiating substrate 1 | 1.4 |

TABLE 11-continued

| Initiating substrate | Relative activity (%) |
|---|---|
| Initiating substrate 2 | 3.2 |
| Initiating substrate 3 | 2.1 |
| Initiating substrate 4 | 0.7 |
| Compound of formula (F) | 52.3 |
| Compound of formula (I) | 44.1 |
| Compound of formula (Q) | 54.3 |

Likewise, reaction was performed under conditions shown below using *Sulfolobus acidocaldarius*-derived geranylgeranyl diphosphate synthase and each of the initiating substrates 1 to 4, the compound represented by the formula (B), the compound represented by the formula (C), the compound represented by the formula (G), the compound represented by the formula (K), the compound represented by the formula (F), the compound represented by the formula (I), the compound represented by the formula (Q), farnesyl diphosphate (FPP), and geranyl diphosphate (GPP). The results were indicated in Tables 12 and 13 by the relative activity of the enzyme on the initiating substrates 1 to 4, the compound represented by the formula (B), the compound represented by the formula (C), the compound represented by the formula (G), the compound represented by the formula (K), the compound represented by the formula (F), the compound represented by the formula (I), and the compound represented by the formula (Q) with the activity of the enzyme on farnesyl diphosphate or geranyl diphosphate as 100.

A reaction solution containing 500 ng of the purified enzyme, 50 mM Tris-HCl buffer (pH 5.8), 40 mM magnesium chloride, 50 mM ammonium chloride, 40 mM Triton X-100, 25 mM 2-mercaptoethanol, 12.5 μM of an initiating substrate, and 50 μM [1-$^{14}$C] isopentenyl diphosphate was prepared and reacted for 1 hour in a water bath at 55° C. After the reaction, liquid scintillation counting and TLC quantification were performed to measure the activity of the enzyme on each initiating substrate.

TABLE 12

| Initiating substrate | Relative activity (%) |
|---|---|
| Geranyl diphosphate | 100 |
| Initiating substrate 1 | 0.4 |
| Initiating substrate 2 | 0.4 |
| Initiating substrate 3 | 0.6 |
| Initiating substrate 4 | 0.8 |
| Compound of formula (F) | 52.3 |
| Compound of formula (I) | 44.1 |
| Compound of formula (Q) | 54.3 |

TABLE 13

| Initiating substrate | Relative activity (%) |
|---|---|
| Farnesyl diphosphate | 100 |
| Initiating substrate 1 | 2.3 |
| Initiating substrate 2 | 2.5 |
| Initiating substrate 3 | 3.9 |
| Initiating substrate 4 | 1.4 |
| Compound of formula (B) | 70.6 |
| Compound of formula (C) | 37.3 |
| Compound of formula (G) | 70.4 |
| Compound of formula (K) | 38.6 |

As is evident from the results of Tables 11 to 13, the enzymatic reactions of *Bacillus stearothermophilus*-derived farnesyl diphosphate synthase and *Sulfolobus acidocaldarius*-derived geranylgeranyl diphosphate synthase hardly proceeded in the case of using the initiating substrates 1 to 4 not maintaining the structure of moiety I in the formula (I), as in use of *Micrococcus luteus* B-P 26-derived undecaprenyl diphosphate synthase. In contrast, the enzymatic reactions proceeded in the case of using the initiating substrates maintaining the structure of moiety I in the formula (I).

The results of Tables 1 to 3 and 10 to 13 have demonstrated that by maintaining the structure of moiety I in the formula (I) in the naturally occurring initiating substrate farnesyl diphosphate, geranyl diphosphate, or the like, even when a desired structure is introduced in a moiety other than moiety I, it is possible to produce isoprene oligomers in the presence of an enzyme having prenyltransferase activity, which is a naturally occurring oligomer-producing enzyme, or any enzyme obtained by partial mutation thereof.

SEQUENCE LISTING FREE TEXT

SEQ ID NO: 1: Base sequence of *Micrococcus luteus* B-P 26-derived undecaprenyl diphosphate synthase (wild-type enzyme)
SEQ ID NO: 2: Amino acid sequence of *Micrococcus luteus* B-P 26-derived undecaprenyl diphosphate synthase (wild-type enzyme)
SEQ ID NO: 3: Base sequence of variant enzyme N31A
SEQ ID NO: 4: Amino acid sequence of variant enzyme N31A
SEQ ID NO: 5: Base sequence of variant enzyme N77A
SEQ ID NO: 6: Amino acid sequence of variant enzyme N77A
SEQ ID NO: 7: Base sequence of variant enzyme L91N
SEQ ID NO: 8: Amino acid sequence of variant enzyme L91N
SEQ ID NO: 9: Base sequence of variant enzyme L91D
SEQ ID NO: 10: Amino acid sequence of variant enzyme L91D
SEQ ID NO: 11: Base sequence of variant enzyme N31Q
SEQ ID NO: 12: Amino acid sequence of variant enzyme N31Q
SEQ ID NO: 13: Base sequence of variant enzyme N77Q
SEQ ID NO: 14: Amino acid sequence of variant enzyme N77Q
SEQ ID NO: 15: Base sequence of variant enzyme L91G
SEQ ID NO: 16: Amino acid sequence of variant enzyme L91G
SEQ ID NO: 17: Base sequence of variant enzyme L91K
SEQ ID NO: 18: Amino acid sequence of variant enzyme L91K
SEQ ID NO: 19: Base sequence of variant enzyme F95A
SEQ ID NO: 20: Amino acid sequence of variant enzyme F95A
SEQ ID NO: 21: Base sequence of variant enzyme F95W
SEQ ID NO: 22: Amino acid sequence of variant enzyme F95W
SEQ ID NO: 23: Sense primer for preparation of variant enzyme N31A
SEQ ID NO: 24: Antisense primer for preparation of variant enzyme N31A
SEQ ID NO: 25: Sense primer for preparation of variant enzyme N77A
SEQ ID NO: 26: Antisense primer for preparation of variant enzyme N77A
SEQ ID NO: 27: Sense primer for preparation of variant enzyme L91N
SEQ ID NO: 28: Antisense primer for preparation of variant enzyme L91N
SEQ ID NO: 29: Sense primer for preparation of variant enzyme L91D
SEQ ID NO: 30: Antisense primer for preparation of variant enzyme L91D
SEQ ID NO: 31: Sense primer for preparation of variant enzyme N31Q
SEQ ID NO: 32: Antisense primer for preparation of variant enzyme N31Q
SEQ ID NO: 33: Sense primer for preparation of variant enzyme N77Q
SEQ ID NO: 34: Antisense primer for preparation of variant enzyme N77Q
SEQ ID NO: 35: Sense primer for preparation of variant enzyme L91G
SEQ ID NO: 36: Antisense primer for preparation of variant enzyme L91G
SEQ ID NO: 37: Sense primer for preparation of variant enzyme L91K
SEQ ID NO: 38: Antisense primer for preparation of variant enzyme L91K
SEQ ID NO: 39: Sense primer for preparation of variant enzyme F95A
SEQ ID NO: 40: Antisense primer for preparation of variant enzyme F95A
SEQ ID NO: 41: Sense primer for preparation of variant enzyme F95W
SEQ ID NO: 42: Antisense primer for preparation of variant enzyme F95W

The invention claimed is:

1. An isoprene oligomer comprising a substituted trans structural moiety and a cis structural moiety, wherein at least one atom or group of an unsubstituted trans structural moiety A of a preliminary isoprene oligomer having the following formula (1) selected from a hydrogen atom, a methyl group, a methylene group, a carbon atom, or a methine group is replaced by a different atom or group to provide the substituted trans structural moiety, and the different atom or group is selected from the group consisting of a nitrogen atom, an oxygen atom, a sulfur atom, a silicon atom, a carbon atom, an acetoxy group, an alkoxy group, a hydroxy group, an aryl group, an alkyl group, an acetyl group, an N-alkyl-acetamino group, and an azide group:

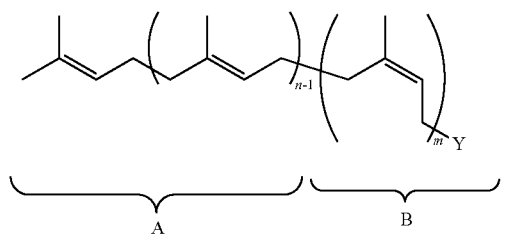

(1)

wherein n represents an integer from 1 to 10; m represents an integer from 1 to 30; the preliminary isoprene oligomer has a cis structural moiety B; and Y represents a hydroxy group, a formyl group, a carboxy group, an ester group, a carbonyl group, or a group having the following formula (2):

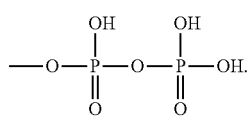

(2)

2. The isoprene oligomer according to claim 1, further comprising a substituted trans group-containing moiety II, an unsubstituted trans moiety III, and the remainder of the isoprene oligomer being a cis group-containing moiety,
wherein at least one atom or group of an unsubstituted trans group-containing moiety II in the following formula (1-1) selected from a hydrogen atom, a methyl group, a methylene group, a carbon atom, or a methine group is replaced by a different atom or group to provide the substituted trans group-containing moiety II; the different atom or group is selected from the group consisting of a nitrogen atom, an oxygen atom, a sulfur atom, a silicon atom, a carbon atom, an acetoxy group, an alkoxy group, a hydroxy group, an aryl group, an alkyl group, an acetyl group, an N-alkyl-acetamino group, and an azide group,

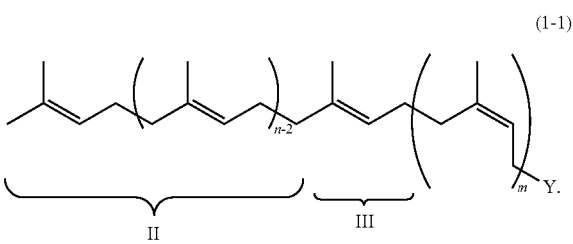

(1-1)

3. The isoprene oligomer according to claim 1 or 2, wherein the trans structural moiety A has any of the following formulas (a) to (s):

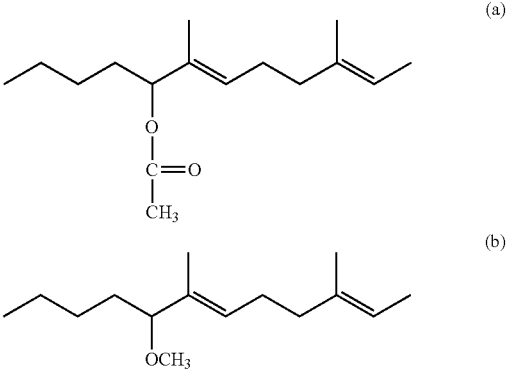

(a)

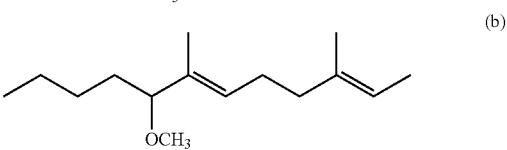

(b)

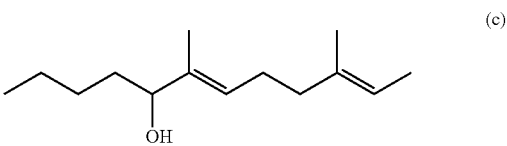

(c)

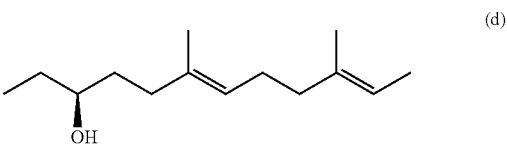

(d)

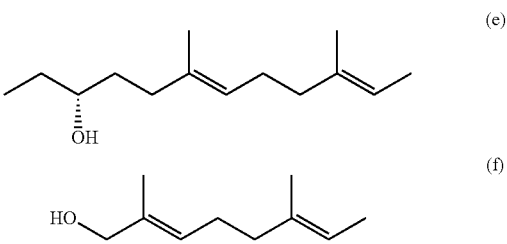

(e)

(f)

-continued

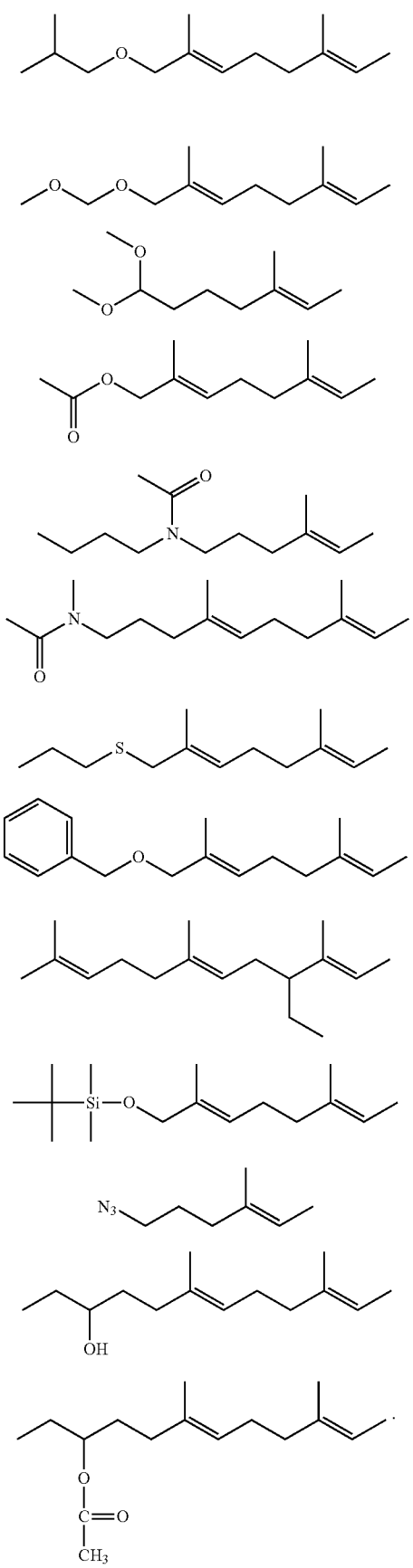

(g)
(h)
(i)
(j)
(k)
(l)
(m)
(n)
(o)
(p)
(q)
(r)
(s)

4. The isoprene oligomer according to claim 1, wherein the isoprene oligomer is biosynthesized using an allylic diphosphate and isopentenyl diphosphate; the allylic diphosphate has the following formula (3), wherein at least 1 atom or group in the isoprene units in formula (3) selected from a hydrogen atom, a methyl group, a methylene group, a carbon atom, or a methine group is replaced by a different atom or group, and the different atom or group is selected from the group consisting of a nitrogen atom, an oxygen atom, a sulfur atom, a silicon atom, a carbon atom, an acetoxy group, an alkoxy group, a hydroxy group, an aryl group, an alkyl group, an acetyl group, an N-alkyl-acetamino group, and an azide group:

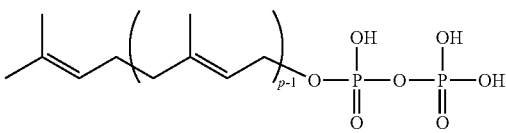

(3)

wherein p represents an integer from 1 to 10.

5. The isoprene oligomer according to claim 4, wherein the biosynthesis is carried out using an enzyme that shows prenyltransferase activity.

6. The isoprene oligomer according to claim 5, wherein the enzyme that shows prenyltransferase activity is any of the following proteins:

[1] a protein comprising an amino acid sequence having any of the following SEQ ID NOs: 2, 4, 6, 8, 10, 12, 14, 16, 18, 20, and 22;

[2] a protein comprising an amino acid sequence that is derived from the amino acid sequence having any of the following SEQ ID NOs: 2, 4, 6, 8, 10, 12, 14, 16, 18, 20, and 22 by substitution, deletion, insertion, or addition of 1 or more amino acids, and possessing the ability to catalyze a reaction between an allylic diphosphate and isopentenyl diphosphate, wherein the allylic diphosphate has the following formula (3), wherein at least 1 atom or group in the isoprene units in formula (3) is replaced by another atom or group; or

[3] a protein comprising an amino acid sequence that shows 45% or higher sequence identity to the amino acid sequence having any of the following SEQ ID NOs: 2, 4, 6, 8, 10, 12, 14, 16, 18, 20, and 22 and possessing the ability to catalyze a reaction between an allylic diphosphate and isopentenyl diphosphate, wherein the allylic diphosphate has the following formula (3), wherein at least 1 atom or group in the isoprene units in formula (3) is replaced by another atom or group:

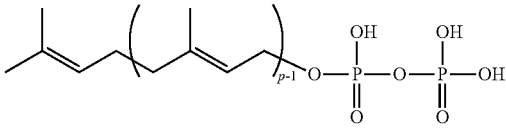

(3)

wherein p represents an integer from 1 to 10.

7. A process for producing the isoprene oligomer according to claim 1, comprising biosynthesis of the isoprene oligomer in presence of allylic diphosphate and isopentenyl diphosphate, wherein the allylic diphosphate has the following formula (3), wherein at least 1 atom or group in the isoprene units in formula (3) is replaced by another atom or group:
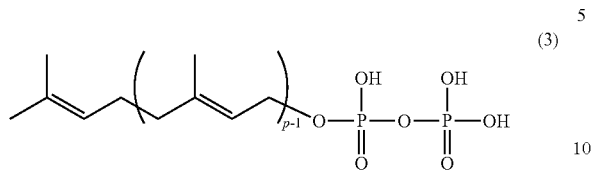
(3)
wherein p represents an integer from 1 to 10.
8. The process for producing the isoprene oligomer according to claim 7, wherein the biosynthesis is carried out in presence of an enzyme showing prenyltransferase activity.
* * * * *